United States Patent
Li et al.

(10) Patent No.: US 10,894,038 B2
(45) Date of Patent: Jan. 19, 2021

(54) INDOLIZINE DERIVATIVES, COMPOSITION AND METHODS OF USE

(71) Applicants: Shanghai Fochon Pharmaceutical Co., Ltd., Shanghai (CN); Fochon Pharmaceuticals, Ltd., Chongqing (CN)

(72) Inventors: Tongshuang Li, San Leandro, CA (US); Xingdong Zhao, Chongqing (CN); Chuiliang Yu, Chongqing (CN); Haohan Tan, Chongqing (CN); Xianlong Wang, Chongqing (CN); Rui Tan, Chongqing (CN); Bin Liu, Chongqing (CN); Weipeng Zhang, Chongqing (CN); Huajie Zhang, Chongqing (CN); Qihong Liu, Chongqing (CN); Zuwen Zhou, Chongqing (CN); Zhifu Li, Chongqing (CN); Yue Rong, Chongqing (CN); Jing Sun, Chongqing (CN); Weibo Wang, Moraga, CA (US)

(73) Assignees: SHANGHAI FOCHON PHARMACEUTICAL CO. LTD., Shanghai (CN); FOCHON PHARMACEUTICALS, LTD., Chongqing (CN)

( * ) Notice: Subject to any disclaimer, the term of this patent is extended or adjusted under 35 U.S.C. 154(b) by 185 days.

(21) Appl. No.: 16/066,599

(22) PCT Filed: Dec. 26, 2016

(86) PCT No.: PCT/CN2016/112071
§ 371 (c)(1),
(2) Date: Jun. 27, 2018

(87) PCT Pub. No.: WO2017/114352
PCT Pub. Date: Jul. 6, 2017

(65) Prior Publication Data
US 2020/0113876 A1  Apr. 16, 2020

Related U.S. Application Data

(60) Provisional application No. 62/272,067, filed on Dec. 28, 2015.

(51) Int. Cl.
| C07D 471/04 | (2006.01) |
| A61K 31/437 | (2006.01) |
| A61P 19/06  | (2006.01) |
| A61K 45/06  | (2006.01) |

(52) U.S. Cl.
CPC ............ *A61K 31/437* (2013.01); *A61K 45/06* (2013.01); *A61P 19/06* (2018.01); *C07D 471/04* (2013.01)

(58) Field of Classification Search
CPC ........................... A61K 31/437; C07D 471/04
See application file for complete search history.

(56) References Cited

FOREIGN PATENT DOCUMENTS

| CN | 105439946 A     | 3/2016  |
| EP | 3 181 557 A1    | 6/2017  |
| WO | WO2009/070740 A2 | 6/2009  |
| WO | WO2011/159839 A2 | 12/2011 |

OTHER PUBLICATIONS

European Extended Search Report, issued in corresponding European Pat. App. No. 16881141.2, 7 pages (dated May 23, 2019).
International Search Report and Written Opinion, dated Mar. 29, 2017, issued in corresponding International Application No. PCT/CN2016/112071.
European Office Action from EP 16881141.2 dated Jun. 2, 2020.

*Primary Examiner* — Paul V Ward
(74) *Attorney, Agent, or Firm* — Foley & Lardner LLP

(57) ABSTRACT

Provided are certain URAT1 inhibitors, pharmaceutical compositions thereof, and methods of use therefor.

20 Claims, No Drawings

INDOLIZINE DERIVATIVES, COMPOSITION AND METHODS OF USE

This application is a national phase of International Application No. PCT/CN2016/112071 filed on Dec. 26, 2016, which claims priority to U.S. Provisional Application No. 62/272,067 filed Dec. 28, 2015, each of which is incorporated herein by reference in its entirety.

FIELD OF THE INVENTION

Provided are certain novel indolizine derivatives or pharmaceutically acceptable salts thereof which can inhibit activity of urate anion transporter 1 (URAT1) and may be useful in reducing uric acid levels and treatment of disorders, particularly hyperuricemia and gout.

BACKGROUND OF THE INVENTION

Uric acid is the final metabolite of endogenous and dietary purine metabolism. The main route of uric acid excretion is the kidney. Approximately two-thirds of uric acid is excreted in the urine and the remaining is excreted in feces. Urate functions as an antioxidant in the blood, but elevated levels of uric acid (a condition known as hyperuricemia) can precipitate gout. Hyperuricemia may result from the overproduction of uric acid or from insufficient renal elimination, or a combination of the both.

Gout is a painful, debilitating and progressive disease caused by abnormally elevated levels of serum uric acid. Gout is associated with elevated levels of uric acid that crystallize and deposit in joints, tendons, and surrounding tissues. This leads to the deposition of painful, needle-like uric acid crystals in and around the connective tissue of the joints and in the kidneys, resulting in inflammation, the formation of disfiguring nodules, intermittent attacks of severe pain and kidney damage. In addition, recent studies suggest that elevated urate levels play a pivotal role in other important diseases such as chronic renal disease, cardiovascular disease, diabetes and hypertension.

Agents that decrease serum uric acid levels may be used to treat the cause of gout. These include agents that: inhibit the enzymes that result in uric acid production, such as xanthine oxidase inhibitors (e.g. allopurinol, febuxostat or thiopurine), or purine nucleoside phosphorylase (PNP) inhibitors (e.g. ulodesine); metabolize uric acid, such as urate oxidases, also known as uricase (e.g. pegloticase); or increase the excretion of uric acid in the urine (uricosurics). Uricosurics include agents that inhibit the transporters responsible for renal reabsorption of uric acid back into the blood, such as benziodarone, isobromindione, probenecid and sulfinpyrazone, and URAT1 inhibitors (e.g. lesinurad).

Urate anion transporter 1 (URAT1) is an organic anion transporter, which primarily found in kidney, and it is also known as solute carrier family 22, member 12, and is encoded by the gene SLC22A12. Human genetic analysis has demonstrated that polymorphisms in the SLC22A12 gene are directly associated with changes in serum uric acid. URAT1-mediated uric acid uptake has been shown by experiments using the *Xenopus* oocyte expression system. Inhibitors of urate transporter, such as URAT1, can prevent reuptake of uric acid at the proximal renal tubule and thus increase renal excretion of uric acid, and are therefore effective in the prevention and treatment of gout.

Although URAT1 inhibitors were disclosed in the arts, e.g. WO 2009070740, WO 2011159839 and WO 2009145456, many suffer from low potency, short half-life or toxicity. Therefore, there is a need for new URAT1 inhibitors that have at least one advantageous property selected from potency, stability, selectivity, toxicity, pharmacokinetics and pharmacodynamics properties as an alternative for the treatment of diseases such as hyperuricemia and gout. In this regard, a novel class of URAT1 inhibitors is provided herein.

DISCLOSURE OF THE INVENTION

Disclosed herein are certain novel indolizine derivatives, pharmaceutically acceptable salts thereof, and pharmaceutical compositions thereof, and their use as pharmaceuticals.

In one aspect, disclosed herein is a compound of formula (I):

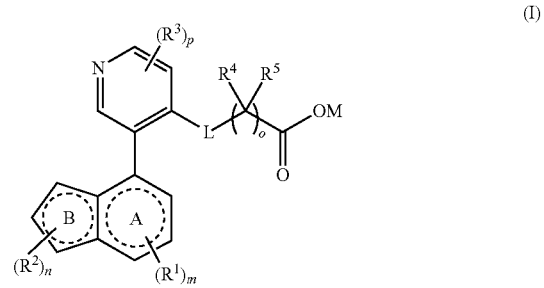

(I)

or a pharmaceutically acceptable salt thereof, wherein:

A-B is an indolizine system, which is selected from:

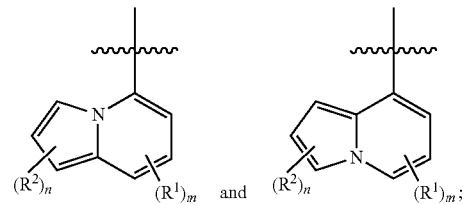

L is selected from $NR^X$, O and S;

each $R^1$ is independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, —CN, —NO$_2$, —NR$^{A1}$R$^{B1}$, —OR$^{A1}$, —S(O)$_r$R$^{A1}$, —S(O)$_2$OR$^{A1}$, —OS(O)$_2$R$^{A1}$, —P(O)R$^{A1}$R$^{B1}$, —P(O)(OR$^{A1}$)(OR$^{B1}$), —C(O)R$^{A1}$, —C(O)OR$^{A1}$, —OC(O)R$^{A1}$, —C(O)NR$^{A1}$R$^{B1}$, —NR$^{A1}$C(O)R$^{B1}$, —OC(O)NR$^{A1}$R$^{B1}$, —NR$^{A1}$C(O)OR$^{B1}$, —NR$^{A1}$C(O)NR$^{A1}$R$^{B1}$, —NR$^{A1}$C(S)NR$^{A1}$R$^{B1}$, —S(O)$_r$NR$^{A1}$R$^{B1}$, —NR$^{A1}$S(O)$_r$R$^{B1}$, —NR$^{A1}$S(O)$_2$R$^{A1}$R$^{B1}$, —S(O)(=NR$^{E1}$)R$^{B1}$, —N=S(O)R$^{A1}$R$^{B1}$, —NR$^{A1}$S(O)(=NR$^{E1}$)R$^{B1}$, —S(O)(=NR$^{E1}$)NR$^{A1}$R$^{B1}$, —R$^{A1}$S(O)(=NR$^{E1}$)NR$^{A1}$R$^{B1}$, —C(=NR$^{E1}$)R$^{A1}$, —C(=N—OR$^{B1}$)R$^{A1}$, C(=NR$^{E1}$)NR$^{A1}$R$^{B1}$, —R$^{A1}$C(=NR$^{E1}$)R$^{B1}$, and —NR$^{A1}$C(=NR$^{E}$)NR$^{A1}$R$^{B1}$, wherein alkyl, alkenyl, alkynyl, cycloalkyl, heterocyclyl, aryl and heteroaryl are each unsubstituted or substituted with at least one substituent, such as one, two, three, or four substituents, independently selected from $R^X$;

each $R^2$ is independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, —CN, —NO$_2$, —NR$^{A2}$R$^{B2}$, —OR$^{A2}$, —S(O)$_r$R$^{A2}$, —S(O)$_2$OR$^{A2}$, —OS(O)$_2$R$^{A2}$, —P(O)R$^{A2}$R$^{B2}$, —P(O)(OR$^{A2}$)(OR$^{B2}$), —C(O)R$^{A2}$, —C(O)OR$^{A2}$, —OC(O)R$^{A2}$, —C(O)NR$^{A2}$R$^{B2}$, NR$^{A2}$C(O)R$^{B2}$, —OC(O)NR$^{A2}$R$^{B2}$, —NR$^{A2}$C(O)OR$^{B2}$, —NR$^{A2}$C(O)NR$^{A2}$R$^{B2}$, —NR$^{A2}$C(S)NR$^{A2}$R$^{B2}$, —S(O)$_r$NR$^{A2}$R$^{B2}$, NR$^{A2}$S(O)$_r$R$^{B2}$, —NR$^{A2}$S(O)$_2$NR$^{A2}$R$^{B2}$, S(O)(=NR$^{E2}$)R$^{B2}$, —N=S(O)R$^{A2}$R$^{B2}$, —NR$^{A2}$S(O)(=NR$^{E2}$)R$^{B2}$, S(O)(=NR$^{E2}$)NR$^{A2}$R$^{B2}$, —NR$^{A2}$S(O)(=NR$^{E2}$)NR$^{A2}$R$^{B2}$, —C(=NR$^{E2}$)R$^{A2}$, —C(=N—OR$^{B2}$)R$^{A2}$, —C(=NR$^{E2}$)NR$^{A2}$R$^{B2}$, —NR$^{A2}$C(=NR$^{E2}$)R$^{B2}$, and —NR$^{A2}$C(=NR$^{E2}$)NR$^{A2}$R$^{B2}$, wherein alkyl, alkenyl, alkynyl, cycloalkyl, heterocyclyl, aryl and heteroaryl are each unsubstituted or substituted with at least one substituent, such as one, two, three, or four substituents, independently selected from R$^X$;

each R$^3$ is independently selected from hydrogen, halogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, heteroaryl-C$_{1-4}$ alkyl, —CN, —NO$_2$, —NR$^{A3}$R$^{B3}$, —OR$^{A3}$, —S(O)$_r$R$^{A3}$, —S(O)$_2$OR$^{A3}$, —OS(O)$_2$R$^{A3}$, —P(O)R$^{A3}$R$^{B3}$, —P(O)(OR$^{A3}$)(OR$^{B3}$), —C(O)R$^{A3}$, —C(O)OR$^{A3}$, —OC(O)R$^{A3}$, —C(O)NR$^{A3}$R$^{B3}$, NR$^{A3}$C(O)R$^{B3}$, —OC(O)NR$^{A3}$R$^{B3}$, NR$^{A3}$C(O)OR$^{B3}$, NR$^{A3}$C(O)NR$^{A3}$R$^{B3}$, —NR$^{A3}$C(S)NR$^{A3}$R$^{B3}$, —S(O)$_r$NR$^{A3}$R$^{B3}$, NR$^{A3}$ S(O)$_r$R$^{B3}$, NR$^{A3}$ S(O)$_2$NR$^{A3}$R$^{B3}$, —S(O)(=NR$^{E3}$)R$^{B3}$, —N=S(O)R$^{A3}$R$^{B3}$, —NR$^{A3}$S(O)(=NR$^{E3}$)R$^{B3}$, S(O)(=NR$^{E3}$)NR$^{A3}$R$^{B3}$, —NR$^{A3}$S(O)(=NR$^{E3}$)NR$^{A3}$R$^{B3}$, —C(=NR$^{E3}$)R$^{A3}$, —C(=N—OR$^{B3}$)R$^{A3}$, C(=NR$^{E3}$)NR$^{A3}$R$^{B3}$, —NR$^{A3}$C(=NR$^{E3}$)R$^{B3}$, and —NR$^{A3}$C(=NR$^{E3}$)NR$^{A3}$R$^{B3}$, wherein alkyl, alkenyl, alkynyl, cycloalkyl, heterocyclyl, aryl and heteroaryl are each unsubstituted or substituted with at least one substituent, such as one, two, three, or four substituents, independently selected from R$^X$;

each R$^4$ and R$^5$ are independently selected from hydrogen, halogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, heteroaryl-C$_{1-4}$ alkyl, wherein the said alkyl, cycloalkyl and heterocyclyl is unsubstituted or substituted with at least one substituent, such as one, two, three, or four substituents, independently selected from R$^X$;

or R$^4$ and R$^5$ together with the carbon atom to which they are attached form a ring of 3 to 7 members containing 0, 1, or 2 heteroatoms independently selected from oxygen, sulfur, nitrogen and phosphorus, and optionally substituted with 1, 2 or 3 R$^X$ groups;

each R$^{A1}$, R$^{A2}$, R$^{A3}$, R$^{B1}$, R$^{B2}$ and R$^{B3}$ are independently selected from hydrogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, and heteroaryl-C$_{1-4}$ alkyl, wherein alkyl, alkenyl, alkynyl, cycloalkyl, heterocyclyl, aryl and heteroaryl are each unsubstituted or substituted with at least one substituent, such as one, two, three, or four substituents, independently selected from R$^X$;

or each "R$^{A1}$ and R$^{B1}$", "R$^{A2}$ and R$^{B2}$", or "R$^{A3}$ and R$^{B3}$" together with the atom(s) to which they are attached form a heterocyclic ring of 4 to 12 members containing 0, 1, or 2 additional heteroatoms independently selected from oxygen, sulfur and nitrogen, and optionally substituted with 1, 2 or 3 R$^X$ groups;

each R$^{E1}$, R$^{E2}$ and R$^{E3}$ are independently selected from hydrogen, C$_{1-10}$ alkyl, CN, NO$_2$, OR$^{a1}$, SR$^{a1}$, —S(O)$_r$R$^{a1}$, —S(O)$_r$NR$^{a1}$R$^{b1}$, —C(O)R$^{a1}$, —C(O)OR$^{a1}$, and —C(O)NR$^{a1}$R$^{b1}$;

each R$^X$ is independently selected from C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, heteroaryl-C$_{1-4}$ alkyl, halogen, —CN, —NO$_2$, —(CR$^{c1}$R$^{d1}$)$_t$NR$^{a1}$R$^{b1}$, —(CR$^{c1}$R$^{d1}$)$_t$OR$^{b1}$, —(CR$^{c1}$R$^{d1}$)$_t$S(O)$_r$R$^{b1}$, —(CR$^{c1}$R$^{d1}$)$_t$S(O)$_2$OR$^{b1}$, —(CR$^{c1}$R$^{d1}$)$_t$OS(O)$_2$R$^{b1}$, —(CR$^{c1}$R$^{d1}$)$_t$P(O)R$^{a1}$R$^{b1}$, —(CR$^{c1}$R$^{d1}$)$_t$P(O)(OR$^{a1}$)(OR$^{b1}$), —(CR$^{c1}$R$^{d1}$)$_t$C(O)R$^{a1}$, —(CR$^{c1}$R$^{d1}$)$_t$C(O)OR$^{b1}$, —(CR$^{c1}$R$^{d1}$)$_t$OC(O)R$^{b1}$, —(CR$^{c1}$R$^{d1}$)$_t$C(O)NR$^{a1}$R$^{b1}$, —(CR$^{c1}$R$^{d1}$)$_t$NR$^{a1}$C(O)R$^{b1}$, —(CR$^{c1}$R$^{d1}$)$_t$OC(O)NR$^{a1}$R$^{b1}$, —(CR$^{c1}$R$^{d1}$)$_t$NR$^{a1}$C(O)OR$^{b1}$, —(CR$^{c1}$R$^{d1}$)$_t$NR$^{a1}$C(O)NR$^{a1}$R$^{b1}$, —(CR$^{c1}$R$^{d1}$)$_t$NR$^{a1}$C(S)NR$^{a1}$R$^{b1}$, —(CR$^{c1}$R$^{d1}$)$_t$S(O)$_r$NR$^{a1}$R$^{b1}$, —(CR$^{c1}$R$^{d1}$)$_t$NR$^{a1}$S(O)$_r$R$^{b1}$, —(CR$^{c1}$R$^{d1}$)$_t$NR$^{a1}$ S(O)$_2$NR$^{a1}$R$^{b1}$, —(CR$^{c1}$R$^{d1}$)$_t$S(O)(=NR$^{e1}$)R$^{b1}$, —(CR$^{c1}$R$^{d1}$)$_t$N=S(O)R$^{a1}$R$^{b1}$, —(CR$^{c1}$R$^{d1}$)$_t$NR$^{a1}$S(O)(=NR$^{e1}$)R$^{b1}$, —(CR$^{c1}$R$^{d1}$)$_t$S(O)(=NR$^{e1}$)NR$^{a1}$R$^{b1}$, —(CR$^{c1}$R$^{d1}$)$_t$NR$^{a1}$S(O)(=NR$^{e1}$)NR$^{a1}$R$^{b1}$, —(CR$^{c1}$R$^{d1}$)$_t$C(=NR$^{e1}$)R$^{a1}$, —(CR$^{c1}$R$^{d1}$)$_t$C(=N—OR$^{b1}$)R$^{a1}$, —(CR$^{c1}$R$^{d1}$)$_t$C(=NR$^{e1}$)NR$^{a1}$R$^{b1}$, —(CR$^{c1}$R$^{d1}$)$_t$NR$^{a1}$C(=NR)R$^{b1}$, and —(CR$^{c1}$R$^{d1}$)$_t$NR$^{a1}$C(=NR)NR$^{a1}$R$^{b1}$, wherein alkyl, alkenyl, alkynyl, cycloalkyl, heterocyclyl, aryl and heteroaryl are each unsubstituted or substituted with at least one substituent, such as one, two, three, or four substituents, independently selected from R$^Y$;

each R$^{a1}$ and each R$^{b1}$ are independently selected from hydrogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, and heteroaryl-C$_{1-4}$ alkyl, wherein alkyl, alkenyl, alkynyl, cycloalkyl, heterocyclyl, aryl and heteroaryl are each unsubstituted or substituted with at least one substituent, such as one, two, three, or four substituents, independently selected from R$^Y$;

or R$^{a1}$ and R$^{b1}$ together with the atom(s) to which they are attached form a heterocyclic ring of 4 to 12 members containing 0, 1, or 2 additional heteroatoms independently selected from oxygen, sulfur, nitrogen and phosphorus, and optionally substituted with 1, 2, or 3 R$^Y$ groups;

each R$^{c1}$ and each R$^{d1}$ are independently selected from hydrogen, halogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, and heteroaryl-C$_{1-4}$ alkyl, wherein alkyl, alkenyl, alkynyl, cycloalkyl, heterocyclyl, aryl and heteroaryl are each unsubstituted or substituted with at least one substituent, such as one, two, three, or four substituents, independently selected from R$^Y$;

or R$^{c1}$ and R$^{d1}$ together with the carbon atom(s) to which they are attached form a ring of 3 to 12 members containing 0, 1, or 2 heteroatoms independently selected from oxygen, sulfur and nitrogen, and optionally substituted with 1, 2, or 3 R$^Y$ groups;

each R$^{e1}$ is independently selected from hydrogen, C$_{1-10}$ alkyl, C$_{3-10}$ cycloalkyl, C$_{3-10}$ cycloalkyl-C$_{1-4}$ alkyl, CN, NO$_2$, OR$^{a2}$, SR$^{a2}$, —S(O)$_r$R$^{a2}$, —S(O)$_r$NR$^{a2}$R$^{b2}$, —C(O)R$^{a2}$, —C(O)OR$^{a2}$, and —C(O)NR$^{a2}$R$^{b2}$;

R$^Y$ is independently selected from C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, heteroaryl-C$_{1-4}$ alkyl, halogen, —CN, —NO$_2$, —(CR$^{c2}$R$^{d2}$)$_t$NR$^{a2}$R$^{b2}$, —(CR$^{c2}$R$^{d2}$)$_t$OR$^{b2}$, —(CR$^{c2}$R$^{d2}$)$_t$S(O)$_r$R$^{b2}$, —(CR$^{c2}$R$^{d2}$)$_t$S(O)$_2$OR$^{b2}$, —(CR$^{c2}$R$^{d2}$)$_t$OS(O)$_2$R$^{b2}$, —(CR$^{c2}$R$^{d2}$)$_t$P(O)R$^{a2}$R$^{b2}$, —(CR$^{c2}$R$^{d2}$)$_t$P(O)(OR$^{a2}$)(OR$^{b2}$), —(CR$^{c2}$R$^{d2}$)$_t$C(O)R$^{a2}$, —(CR$^{c2}$R$^{d2}$)$_t$C(O)OR$^{b2}$, —(CR$^{c2}$R$^{d1}$)$_t$OC(O)R$^{a2}$, —(CR$^{c2}$R$^{d2}$)$_t$C(O)NR$^{a2}$R$^{b2}$, —(CR$^{c2}$R$^{d2}$)$_t$NR$^{a2}$C(O)R$^{b2}$, —(CR$^{c2}$R$^{d2}$)$_t$OC(O)NR$^{a2}$R$^{b2}$, —(CR$^{c2}$R$^{d2}$)$_t$NR$^{a2}$C(O)

$OR^{b2}$, —$(CR^{c2}R^{d2})_tNR^{a2}C(O)NR^{a2}R^{b2}$, —$(CR^{c2}R^{d2})_t$ $NR^{a2}C(S)NR^{a2}R^{b2}$, —$(CR^{c2}R^{d2})_tS(O)_rNR^{a2}R^{b2}$, —$(CR^{c2}R^{d2})_tNR^{a2}S(O)_rR^{b2}$, —$(CR^{c2}R^{d2})_tNR^{a2}S(O)_2$ $NR^{a2}R^{b2}$, —$(CR^{c2}R^{d2})_tS(O)(=NR^{e2})R^{b2}$, —$(CR^{c2}R^{d2})_t$ $N=S(O)R^{a2}R^{b2}$, —$(CR^{c2}R^{d2})_tNR^{a2}$ $S(O)(=NR^{e2})R^{b2}$, —$(CR^{c2}R^{d2})_tS(O)(=NR^{e2})NR^{a2}R^{b2}$, —$(CR^{c2}R^{d2})_tR^{a2}S(O)$ $(=NR^{e2})NR^{a2}R^{b2}$, —$(CR^{c2}R^{d2})_tC(=NR^{e2})R^{a2}$, —$(CR^{c2}R^{d2})_tC(=N-OR^{b2})R^{a2}$, —$(CR^{c2}R^{d2})_tC(=NR^{e2})$ $NR^{a2}R^{b2}$, —$(CR^{c2}R^{d2})_tNR^{a2}C(=NR^{e2})R^{b2}$, and —$(CR^{c2}R^{d2})_tNR^{a2}C(=NR^{e2})NR^{a2}R^{b2}$, wherein alkyl, alkenyl, alkynyl, cycloalkyl, heterocyclyl, aryl and heteroaryl are each unsubstituted or substituted with at least one substituent, such as one, two, three, or four substituents, independently selected from OH, CN, amino, halogen, $C_{1-10}$ alkyl, $C_{2-10}$ alkenyl, $C_{2-10}$ alkynyl, $C_{3-10}$ cycloalkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino and di($C_{1-10}$ alkyl)amino;

each $R^{a2}$ and each $R^{b2}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl)amino, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, such as one, two, three, or four substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

or $R^{a2}$ and $R^{b2}$ together with the atom(s) to which they are attached form a heterocyclic ring of 4 to 12 members containing 0, 1, or 2 additional heteroatoms independently selected from oxygen, sulfur, nitrogen and phosphorus, and optionally substituted with 1 or 2 substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl) amino;

each $R^{c2}$ and each $R^{d2}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl) amino, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, such as one, two, three, or four substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

or $R^{c2}$ and $R^{d2}$ together with the carbon atom(s) to which they are attached form a ring of 3 to 12 members containing 0, 1, or 2 heteroatoms independently selected from oxygen, sulfur and nitrogen, and optionally substituted with 1 or 2 substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{e2}$ is independently selected from hydrogen, CN, $NO_2$, $C_{1-10}$ alkyl, $C_{3-10}$ cycloalkyl, $C_{3-10}$ cycloalkyl-$C_{1-4}$ alkyl, $C_{1-10}$ alkoxy, $C_{3-10}$ cycloalkoxy, —$C(O)C_{1-4}$ alkyl, —$C(O)C_{3-10}$ cycloalkyl, —$C(O)OC_{1-4}$ alkyl, —$C(O)OC_{3-10}$ cycloalkyl, —$C(O)NH_2$, —$C(O)NH(C_{1-4}$ alkyl), —$C(O)N(C_{1-4}$ alkyl)$_2$, —$C(O)NH(C_{3-10}$ cycloalkyl), —$C(O)N(C_{3-10}$ cycloalkyl)$_2$, —$S(O)_2C_{1-4}$ alkyl, —$S(O)_2C_{3-10}$ cycloalkyl, —$S(O)_2NH_2$, —$S(O)_2NH(C_{1-4}$ alkyl), —$S(O)_2N(C_{1-4}$ alkyl)$_2$, —$S(O)_2NH(C_{3-10}$ cycloalkyl) and —$S(O)_2N(C_{3-10}$ cycloalkyl)$_2$;

M is hydrogen, $C_{1-4}$ alkyl or a pharmaceutically acceptable cation;

m is independently selected from 0, 1, 2 and 3;

n is independently selected from 0, 1, 2, and 3;

o is selected from 1, 2 and 3.

p is independently selected from 0, 1, 2 and 3;

each r is independently selected from 0, 1 and 2;

each t is independently selected from 0, 1, 2, 3 and 4.

In another aspect, disclosed is a pharmaceutical composition comprising a compound of formula (I) or a pharmaceutically acceptable salt thereof and a pharmaceutically acceptable excipient.

In yet another aspect, disclosed is a method for decreasing uric acid levels in one or more tissues or organs of a subject in need of decreasing uric acid levels by modulating URAT1, comprising administering to a system or a subject in need thereof, a therapeutically effective amount of a compound of formula (I) or a pharmaceutically acceptable salt thereof or a pharmaceutical composition thereof.

In yet another aspect, disclosed is a method to treat, ameliorate or prevent a condition which responds to inhibition of URAT1 comprising administering to a system or subject in need of such treatment an effective amount of a compound of formula (I) or a pharmaceutically acceptable salt thereof or a pharmaceutical composition thereof, and optionally in combination with a second therapeutic agent, thereby treating said condition. In some embodiments, the subject in need of decreased uric acid levels has a disorder characterized by abnormally high content of uric acid in one or more tissues or organs of the subject. In some embodiments, the disorder is characterized by over production of uric acid, low excretion of uric acid, tumor lysis, a blood disorder or a combination thereof. In some embodiments, the disorder is gout.

Alternatively, disclosed is the use of a compound of formula (I) or a pharmaceutically acceptable salt thereof in the manufacture of a medicament for treating a condition mediated by URAT1. In particular embodiments, the compounds of the disclosure may be used alone or in combination with a second therapeutic agent to treat a condition mediated by URAT1.

Alternatively, disclosed is a compound of formula (I) or a pharmaceutically acceptable salt thereof for treating a condition mediated by URAT1.

Specifically, the condition disclosed herein includes but not limited to, hyperuricaemia, gout, a recurrent gout attach, tophaceous gout, arthritis, gouty arthritis, inflammatory arthritis, joint inflammation, deposition of urate crystals in the joint, kidney disease, kidney stones, kidney failure, urolithiasis, hypertension, a cardiovascular disease, coronary heart disease, Lesch-Nyhan syndrome, Kelley-Seegmiller syndrome, urolithiasis, plumbism, hyperparathyroidism, psoriasis, sarcoidosis, and hypoxanthine-guanine phosphoribosyltransferase (HPRT) deficiency or a combination thereof.

More specifically, the condition disclosed herein is gout.

Alternatively, a compound of formula (I) or a pharmaceutically acceptable salt thereof disclosed herein may be used in the treatment of hyperuricemia where this is present together with one or more other diseases, such as kidney failure, type 2 diabetes, cardiovascular disease (e.g. hypertension, myocardial infarction, heart failure, coronary artery disease, cerebrovascular disease, atherosclerosis, angina, aneurism, hyperlipidemia and stroke), obesity, metabolic syndrome, myeloproliferative disorders, lymphoproliferative disorders and disorders associated with certain medications, such as a diuretic (e.g. a thiazide), an immunosuppressant (e.g. a cyclosporine therapy), a chemotherapeutic agent (e.g. cisplatin) or aspirin.

Furthermore, disclosed is a method for treating a condition characterized by abnormal tissue or organ levels of uric acid, comprising administering to a system or subject in need of such treatment an effective amount of a compound of formula (I) or a pharmaceutically acceptable salt thereof or a pharmaceutical composition thereof, and optionally in combination with a second therapeutic agent, thereby treating said condition.

Alternatively, disclosed is the use of a compound of formula (I) or a pharmaceutically acceptable salt thereof in the manufacture of a medicament for treating a condition characterized by abnormal tissue or organ levels of uric acid. In particular examples, the compounds of the disclosure may be used alone or in combination with a chemotherapeutic agent to treat a condition characterized by abnormal tissue or organ levels of uric acid.

Specifically, the condition disclosed herein includes but not limited to, hyperuricaemia, gout, a recurrent gout attach, tophaceous gout, arthritis, gouty arthritis, inflammatory arthritis, joint inflammation, deposition of urate crystals in the joint, kidney disease, kidney stones, kidney failure, urolithiasis, hypertension, a cardiovascular disease, coronary heart disease, Lesch-Nyhan syndrome, Kelley-Seegmiller syndrome, urolithiasis, plumbism, hyperparathyroidism, psoriasis, sarcoidosis, and hypoxanthine-guanine phosphoribosyltransferase (HPRT) deficiency or a combination thereof.

More specifically, the condition herein is gout.

In the above method(s) for using the compounds of the disclosure, a compound of formula (I) or a pharmaceutically acceptable salt thereof may be administered to a system comprising cells or tissues, or to a subject including a mammalian subject such as a human or animal subject.

Certain Terminology

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there is a plurality of definitions for terms herein, those in this section prevail.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting. Likewise, use of the term "comprising" as well as other forms, such as "comprise", "comprises", and "comprised" is not limiting.

Definition of standard chemistry terms may be found in reference works, including Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

Where substituent groups are specified by their conventional chemical formulas, written from left to right, they equally encompass the chemically identical substituents that would result from writing the structure from right to left. As a non-limiting example, $CH_2O$ is equivalent to $OCH_2$.

As used herein, the term "optionally substituted" means unsubstituted or substituted. The term "substituted" means that a hydrogen atom is removed and replaced by a substituent. It is to be understood that substitution at a given atom is limited by valency. Throughout the definitions, the term "$C_{i-j}$" indicates a range which includes the endpoints, wherein i and j are integers and indicate the number of carbons. Examples include $C_{1-4}$, $C_{1-10}$, $C_{3-10}$, and the like.

The term "alkyl" refers to both branched and straight-chain saturated aliphatic hydrocarbon groups having the specified number of carbon atoms. Unless otherwise specified, "alkyl" refers to $C_1$-$C_6$ alkyl. For example, $C_1$-$C_6$, as in "$C_{1-6}$ alkyl" is defined to include groups having 1, 2, 3, 4, 5, or 6 carbons in a linear or branched arrangement. For example, "$C_{1-8}$ alkyl" includes but is not limited to methyl, ethyl, n-propyl, i-propyl, n-butyl, t-butyl, i-butyl, pentyl, hexyl, heptyl, and octyl.

The term "cycloalkyl" as used herein, means a monocyclic or bridged hydrocarbon ring system. The monocyclic cycloalkyl is a carbocyclic ring system containing three to ten carbon atoms, zero heteroatoms and zero double bonds. Examples of monocyclic ring systems include cyclopropyl, cyclobutyl, cyclopentyl, cyclohexyl, cycloheptyl, and cyclooctyl. The monocyclic ring may contain one or two alkylene bridges, each consisting of one, two, or three carbon atoms, each linking two non-adjacent carbon atoms of the ring system. Representative examples of such bridged cycloalkyl ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane, tricyclo[3.3.1.0³’⁷]nonane, and tricyclo[3.3.1.1³’⁷]decane (adamantane). The monocyclic and bridged cycloalkyl can be attached to the parent molecular moiety through any substitutable atom contained within the ring system.

The term "alkenyl" refers to a non-aromatic hydrocarbon radical, straight, branched or cyclic, containing from 2 to 10 carbon atoms and at least one carbon to carbon double bond. In some embodiments, one carbon to carbon double bond is present, and up to four non-aromatic carbon-carbon double bonds may be present. Thus, "$C_{2-6}$ alkenyl" means an alkenyl radical having from 2 to 6 carbon atoms. Alkenyl groups include but are not limited to ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. In some embodiments, up to three carbon-carbon triple bonds may be present. Thus, "$C_{2-6}$ alkynyl" means an alkynyl radical having from 2 to 6 carbon atoms. Alkynyl groups include but are not limited to ethynyl, propynyl, butynyl, and 3-methylbutynyl. The straight, branched or cyclic portion of the alkynyl group may contain triple bonds and may be substituted if a substituted alkynyl group is indicated.

The term "halogen" (or "halo") refers to fluorine, chlorine, bromine and iodine.

The term "alkoxy", employed alone or in combination with other terms, refers to an alkyl radical that is single bonded to an oxygen atom. The attachment point of an alkoxy radical to a molecule is through the oxygen atom. An alkoxy radical may be depicted as —O-alkyl. The term "$C_{1-10}$ alkoxy" refers to an alkoxy radical containing from one to ten carbon atoms, having straight or branched moieties. Alkoxy groups, includes but is not limited to, methoxy, ethoxy, propoxy, isopropoxy, butoxy, hexyloxy, and the like.

The term "cycloalkoxy", employed alone or in combination with other terms, refers to cycloalkyl radical that is single bonded to an oxygen atom. The attachment point of a cycloalkoxy radical to a molecule is through the oxygen atom. A cycloalkoxy radical may be depicted as —O-cycloalkyl. "$C_{3-10}$ cycloalkoxy" refers to a cycloalkoxy radical containing from three to ten carbon atoms. Cycloalkoxy groups, includes but is not limited to, cyclopropoxy, cyclobutoxy, cyclohexyloxy, and the like.

The term "alkylthio", employed alone or in combination with other terms, refers to an alkyl radical that is single bonded to a sulfur atom. The attachment point of an alkylthio radical to a molecule is through the sulfur atom. An alkylthio radical may be depicted as —S-alkyl. The term "$C_{1-10}$ alkylthio" refers to an alkylthio radical containing from one to ten carbon atoms, having straight or branched moieties. Alkylthio groups, includes but is not limited to, methylthio, ethylthio, propylthio, isopropylthio, butylthio, hexylthio, and the like.

The term "cycloalkylthio", employed alone or in combination with other terms, refers to cycloalkyl radical that is single bonded to a sulfur atom. The attachment point of a cycloalkylthio radical to a molecule is through the sulfur atom. A cycloalkylthio radical may be depicted as —S-cycloalkyl. "$C_{3-10}$ cycloalkylthio" refers to a cycloalkylthio radical containing from three to ten carbon atoms. Cycloalkylthio groups, includes but is not limited to, cyclopropylthio, cyclobutylthio, cyclohexylthio, and the like.

The term "alkylamino", employed alone or in combination with other terms, refers to an alkyl radical that is single bonded to a nitrogen atom. The attachment point of an alkylamino radical to a molecule is through the nitrogen atom. An alkylamino radical may be depicted as —NH(alkyl). The term "$C_{1-10}$ alkylamino" refers to an alkylamino radical containing from one to ten carbon atoms, having straight or branched moieties. Alkylamino groups, includes but is not limited to, methylamino, ethylamino, propylamino, isopropylamino, butylamino, hexylamoino, and the like.

The term "cycloalkylamino", employed alone or in combination with other terms, refers to cycloalkyl radical that is single bonded to a nitrogen atom. The attachment point of a cycloalkylamino radical to a molecule is through the nitrogen atom. A cycloalkylamino radical may be depicted as —NH(cycloalkyl). "$C_{3-10}$ cycloalkylamino" refers to a cycloalkylamino radical containing from three to ten carbon atoms. Cycloalkylamino groups, includes but is not limited to, cyclopropylamino, cyclobutylamino, cyclohexylamino, and the like.

The term "di(alkyl)amino", employed alone or in combination with other terms, refers to two alkyl radicals that are single bonded to a nitrogen atom. The attachment point of an di(alkyl)amino radical to a molecule is through the nitrogen atom. A di(alkyl)amino radical may be depicted as —N(alkyl)$_2$. The term "di($C_{1-10}$ alkyl)amino" refers to a di($C_{1-10}$ alkyl)amino radical wherein the alkyl radicals each independently contains from one to ten carbon atoms, having straight or branched moieties.

The term "aryl" encompasses: 5- and 6-membered carbocyclic aromatic rings, for example, benzene; bicyclic ring systems wherein at least one ring is carbocyclic and aromatic, for example, naphthalene, indane, and 1, 2, 3, 4-tetrahydroquinoline; and tricyclic ring systems wherein at least one ring is carbocyclic and aromatic, for example, fluorene. In cases where the aryl substituent is bicyclic or tricyclic and at least one ring is non-aromatic, it is understood that attachment is via the aromatic ring.

For example, aryl includes 5- and 6-membered carbocyclic aromatic rings fused to a 5- to 7-membered heterocyclic ring containing one or more heteroatoms selected from N, O, and S, provided that the point of attachment is at the carbocyclic aromatic ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings are fused with a heterocyclic aromatic ring, the resulting ring system is heteroaryl, not aryl, as defined herein.

The term "heteroaryl" refers to
  5- to 8-membered aromatic, monocyclic rings containing one or more, for example, from 1 to 4, or, in some embodiments, from 1 to 3, heteroatoms selected from N, O, and S, with the remaining ring atoms being carbon;
  8- to 12-membered bicyclic rings containing one or more, for example, from 1 to 4, or, in some embodiments, from 1 to 3, heteroatoms selected from N, O, and S, with the remaining ring atoms being carbon and wherein at least one heteroatom is present in an aromatic ring; and 11- to 14-membered tricyclic rings containing one or more, for example, from 1 to 4, or in some embodiments, from 1 to 3, heteroatoms selected from N, O, and S, with the remaining ring atoms being carbon and wherein at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 1-pyrazolyl, 2,3-pyrazolyl, 2,4-imidazolinyl, isoxazolyl, oxazolyl, thiazolyl, thiadiazolyl, tetrazolyl, thienyl, benzothienyl, furyl, benzofuryl, benzoimidazolinyl, indolinyl, pyridizinyl, triazolyl, quinolinyl, pyrazolyl, and 5,6,7,8-tetrahydroisoquinoline.

Further heteroaryl groups include, but are not limited to, pyrrolyl, isothiazolyl, triazinyl, pyrazinyl, pyridazinyl, indolyl, benzotriazolyl, quinoxalinyl, and isoquinolinyl. As with the definition of heterocycle below, "heteroaryl" is also understood to include the N-oxide derivative of any nitrogen-containing heteroaryl.

Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

In cases where the heteroaryl substituent is bicyclic or tricyclic and at least one ring is non-aromatic or contains no heteroatoms, it is understood that attachment is via the aromatic ring or via the heteroatom containing ring, respectively.

The term "heterocycle" (and variations thereof such as "heterocyclic", or "heterocyclyl") broadly refers to a single aliphatic ring, usually with 3 to 12 ring atoms, containing at least 2 carbon atoms in addition to one or more, preferably one to three heteroatoms independently selected from oxygen, sulfur, and nitrogen, as well as combinations comprising at least one of the foregoing heteroatoms. Alternatively, a heterocycle as defined above may be multicyclic ring system (e.g. bicyclic) in which two or more rings may be fused or bridged or spiro together, wherein at least one such ring contains one or more heteroatoms independently selected from oxygen, sulfur, and nitrogen. "Heterocycle" also refers to 5- to 7-membered heterocyclic ring containing one or more heteroatoms selected from N, O, and S fused with 5- and 6-membered carbocyclic aromatic ring, provided that the point of attachment is at the heterocyclic ring. The rings may be saturated or have one or more double bonds (i.e. partially unsaturated). The heterocycle can be substituted by oxo. The nitrogen and sulfur heteroatoms in the heterocycle rings may optionally be oxidized and the nitrogen atoms may optionally be quarternized. The heterocycle is connected to the parent molecular moiety through any substitutable carbon or any substitutable heteroatom contained within the rings, provided that attachment results in the creation of a stable structure. When the heterocyclic ring has substituents, it is understood that the substituents may be attached to any atom in the ring, whether a heteroatom or a carbon atom, provided that a stable chemical structure results. Heterocycle does not overlap with heteroaryl.

Suitable heterocycles include, but are not limited to (as numbered from the linkage position assigned priority 1), 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, and 2,5-piperazinyl. Morpholinyl groups are also contemplated, including 2-morpholinyl and 3-morpholinyl (numbered wherein the oxygen is assigned priority 1). Substituted heterocycle also includes ring systems substituted with one or more oxo moieties, such as piperidinyl N-oxide, morpholinyl-N-oxide, 1-oxo-1-thiomorpholinyl and 1,1-dioxo-1-thiomorpholinyl. Bicyclic heterocycles include, but are not limited to,

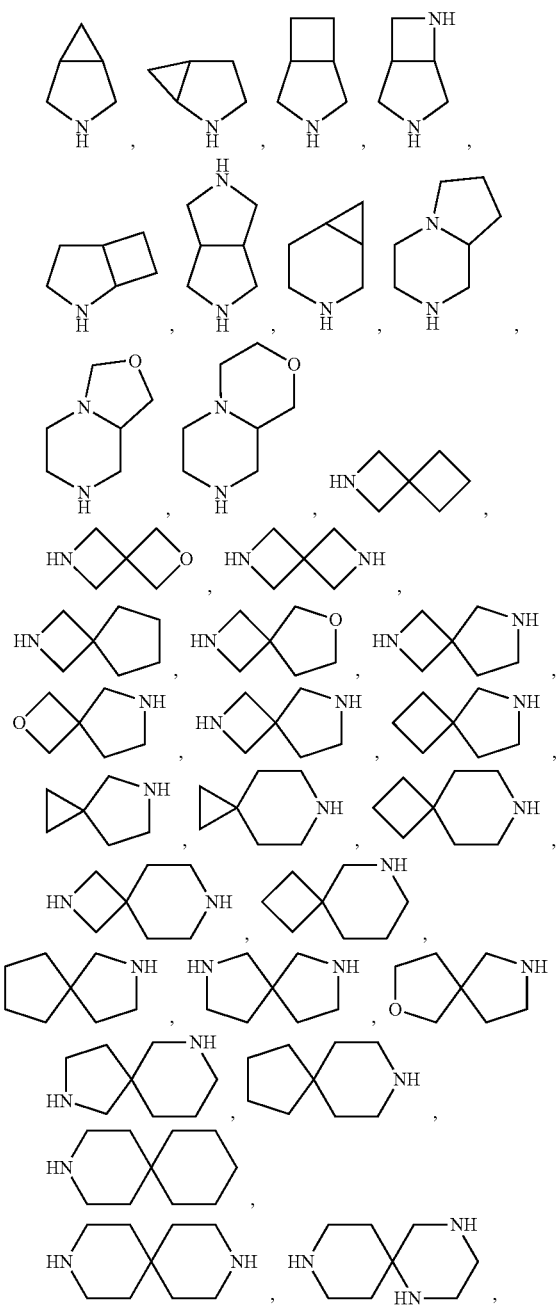

-continued

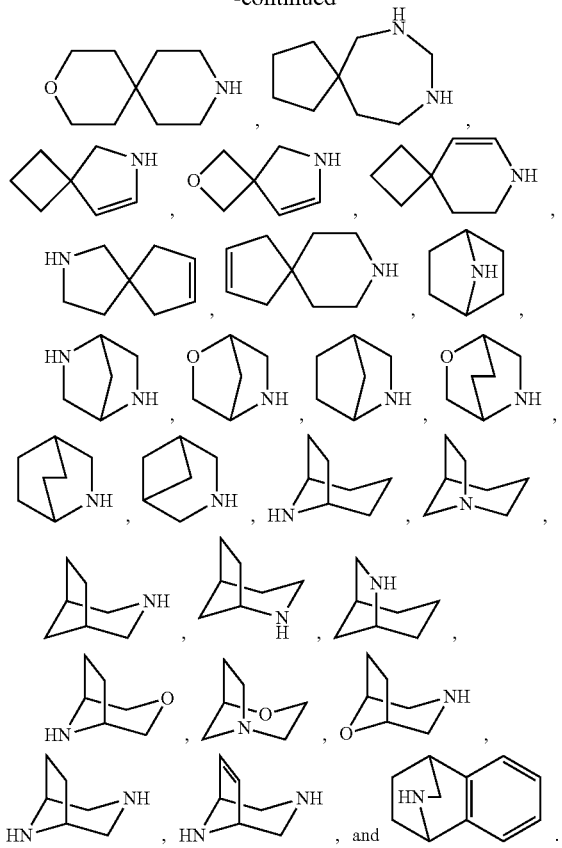

As used herein, "aryl-alkyl" refers to an alkyl moiety substituted by an aryl group. Example aryl-alkyl groups include benzyl, phenethyl, and naphthylmethyl groups. In some embodiments, aryl-alkyl groups have from 7 to 20 or 7 to 11 carbon atoms. When used in the phrase "aryl-$C_{1-4}$ alkyl", the term "$C_{1-4}$" refers to the alkyl portion of the moiety and does not describe the number of atoms in the aryl portion of the moiety.

As used herein, "heterocyclyl-alkyl" refers to alkyl substituted by heterocyclyl. When used in the phrase "heterocyclyl-$C_{1-4}$alkyl", the term "$C_{1-4}$" refers to the alkyl portion of the moiety and does not describe the number of atoms in the heterocyclyl portion of the moiety.

As used herein, "cycloalkyl-alkyl" refers to alkyl substituted by cycloalkyl. When used in the phrase "$C_{3-10}$ cycloalkyl-alkyl", the term "$C_{3-10}$" refers to the cycloalkyl portion of the moiety and does not describe the number of atoms in the alkyl portion of the moiety, and the term "$C_{1-4}$" refers to the alkyl portion of the moiety and does not describe the number of atoms in the cycloalkyl portion of the moiety.

As used herein, "heteroaryl-alkyl" refers to alkyl substituted by heteroaryl. When used in the phrase "heteroaryl-$C_{1-4}$ alkyl", the term "$C_{1-4}$" refers to the alkyl portion of the moiety and does not describe the number of atoms in the heteroaryl portion of the moiety.

For avoidance of doubt, reference, for example, to substitution of alkyl, cycloalkyl, heterocyclyl, aryl, and/or heteroaryl refers to substitution of each of those groups individually as well as to substitutions of combinations of those groups. That is, if $R^1$ is aryl-$C_{1-4}$ alkyl, the aryl portion may be unsubstituted or substituted with at least one substituent, such as one, two, three, or four substituents, independently selected from $R^X$ and the alkyl portion may also be unsubstituted or substituted with at least one substituent, such as one, two, three, or four substituents, independently selected from $R^X$.

The term "pharmaceutically acceptable salts" refers to salts prepared from pharmaceutically acceptable non-toxic bases or acids including inorganic or organic bases and inorganic or organic acids. Salts derived from inorganic bases may be selected, for example, from aluminum, ammonium, calcium, copper, ferric, ferrous, lithium, magnesium, manganic, manganous, potassium, sodium, and zinc salts. Further, for example, the pharmaceutically acceptable salts derived from inorganic bases may be selected from ammonium, calcium, magnesium, potassium, and sodium salts. Salts in the solid form may exist in one or more crystal structures, and may also be in the form of hydrates. Salts derived from pharmaceutically acceptable organic non-toxic bases may be selected, for example, from salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, and tripropylamine, tromethamine.

When the compound disclosed herein is basic, salts may be prepared using a pharmaceutically acceptable non-toxic acid, selected from inorganic and organic acids. Such acid may be selected, for example, from acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluenesulfonic acids. In some embodiments, such acid may be selected, for example, from citric, hydrobromic, hydrochloric, maleic, phosphoric, sulfuric, fumaric, and tartaric acids.

The terms "administration of" and or "administering" a compound or a pharmaceutically acceptable salt should be understood to mean providing a compound or a pharmaceutically acceptable salt thereof to the individual in recognized need of treatment.

The term "effective amount" means the amount of the a compound or a pharmaceutically acceptable salt that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to a pharmaceutical composition is intended to encompass a product comprising the active ingredient (s), and the inert ingredient (s) that make up the carrier, as well as any product which results, directly or indirectly, from combination, complexation or aggregation of any two or more of the ingredients, or from dissociation of one or more of the ingredients, or from other types of reactions or interactions of one or more of the ingredients.

The term "pharmaceutically acceptable" it is meant compatible with the other ingredients of the formulation and not unacceptably deleterious to the recipient thereof.

The term "subject" as used herein in reference to individuals suffering from a disorder, a condition, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat", "treating" or "treatment," and other grammatical equivalents as used herein, include alleviating, abating or ameliorating a disease or condition, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The term "protecting group" or "Pg" refers to a substituent that can be commonly employed to block or protect a certain functionality while reacting other functional groups on the compound. For example, an "amino-protecting group" is a substituent attached to an amino group that blocks or protects the amino functionality in the compound. Suitable amino-protecting groups include but are not limited to acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include but are not limited to acetyl and silyl. A "carboxy-protecting group" refers to a substituent of the carboxy group that blocks or protects the carboxy functionality. Common carboxy-protecting groups include —CH$_2$CH$_2$SO$_2$Ph, cyanoethyl, 2-(trimethylsilyl)ethyl, 2-(trimethylsilyl)ethoxymethyl, 2-(p-toluenesulfonyl)ethyl, 2-(p-nitrophenylsulfenyl) ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The term "NH protecting group" as used herein includes, but not limited to, trichloroethoxycarbonyl, tribromoethoxycarbonyl, benzyloxycarbonyl, para-nitrobenzylcarbonyl, ortho-bromobenzyloxycarbonyl, chloroacetyl, dichloroacetyl, trichloroacetyl, trifluoroacetyl, phenylacetyl, formyl, acetyl, benzoyl, tert-amyloxycarbonyl, tert-butoxycarbonyl, para-methoxybenzyloxycarbonyl, 3,4-dimethoxybenzyloxycarbonyl, 4-(phenylazo)-benzyloxycarbonyl, 2-furfuryloxycarbonyl, diphenylmethoxycarbonyl, 1,1-dimethyl-propoxy-carbonyl, isopropoxycarbonyl, phthaloyl, succinyl, alanyl, leucyl, 1-adamantyloxycarbonyl, 8-quinolyloxycarbonyl, benzyl, diphenylmethyl, triphenylmethyl, 2-nitrophenylthio, methanesulfonyl, para-toluenesulfonyl, N,N-dimethylaminomethylene, benzylidene, 2-hydroxybenzylidene, 2-hydroxy-5-chlorobenzylidene, 2-hydroxy-1-naphthylmethylene, 3-hydroxy-4-pyridylmethylene, cyclohexylidene, 2-ethoxycarbonylcyclohexylidene, 2-ethoxycarbonylcyclopentylidene, 2-acetylcyclohexylidene, 3,3-dimethyl-5-oxycyclo-hexylidene, diphenylphosphoryl, dibenzylphosphoryl, 5-methyl-2-oxo-2H-1,3-dioxol-4-yl-methyl, trimethylsilyl, triethylsilyl, and triphenylsilyl.

The term "C(O)OH protecting group" as used herein includes, but not limited to, methyl, ethyl, n-propyl, isopropyl, 1,1-dimethylpropyl, n-butyl, tert-butyl, phenyl, naphthyl, benzyl, diphenylmethyl, triphenylmethyl, para-nitrobenzyl, para-methoxybenzyl, bis(para-methoxyphenyl) methyl, acetylmethyl, benzoylmethyl, para-nitrobenzoylmethyl, para-bromobenzoylmethyl, para-methanesulfonylbenzoylmethyl, 2-tetrahydropyranyl, 2-tetrahydrofuranyl, 2,2,2-trichloro-ethyl, 2-(trimethylsilyl) ethyl, acetoxymethyl, propionyloxymethyl, pivaloyloxymethyl, phthalimidomethyl, succinimidomethyl, cyclopropyl, cyclobutyl, cyclopentyl, cyclohexyl, methoxymethyl, methoxyethoxymethyl, 2-(trimethylsilyl)ethoxymethyl, benzyloxymethyl, methylthiomethyl, 2-methylthioethyl, phenylthiomethyl, 1,1-dimethyl-2-propenyl, 3-methyl-3-butenyl, allyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

The term "OH or SH protecting group" as used herein includes, but not limited to, benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl) ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, benzoyl, methyl, tert-butyl, 2,2,2-trichloroethyl, 2-trimethyl silylethyl, 1,1-dimethyl-2-propenyl, 3-methyl-3-butenyl, allyl, benzyl (phenylmethyl), para-methoxybenzyl, 3,4-dimethoxybenzyl, diphenylmethyl, triphenylmethyl, tetrahydrofuryl, tetrahydropyranyl, tetrahydrothiopyranyl, methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl, methanesulfonyl, para-toluenesulfonyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl are designated as being of cis or trans configuration.

Furthermore, the invention contemplates the various isomers and mixtures thereof resulting from the disposal of substituents around an adamantane ring system. Two substituents around a single ring within an adamantane ring system are designated as being of Z or E relative configuration. For examples, see C. D. Jones, M. Kaselj, R. N. Salvatore, W. J. le Noble J. Org. Chem. 1998, 63, 2758-2760.

Compounds of this invention may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85-90%, more preferably an excess of about 95-99%, and still more preferably an excess greater than about 99%. Accordingly, this invention includes racemic mixtures, relative and absolute stereoisomers, and mixtures of relative and absolute stereoisomers.

Isotope Enriched or Labeled Compounds

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, nitrogen, phosphorous, sulfur, fluorine, chlorine, and iodine include, but are not limited to, $^{2}H$, $^{3}H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

In another embodiment, the isotope-labeled compounds contain deuterium ($^{2}H$), tritium ($^{3}H$) or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuterated acid such as $D_2SO_4/D_2O$. In addition to the above, relevant procedures and intermediates are disclosed, for instance, in Lizondo, J et al, Drugs Fut, 21(11), 1116 (1996); Brickner, S J et al., J Med Chem, 39(3), 673 (1996); Mallesham, B et al, Org Lett, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of URAT1 inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al, J. Labelled Comp. Radiopharmaceut., 36(10):927-932 (1995); Kushner et al., Can. J. Physiol. Pharmacol, 77, 79-88 (1999).

In addition, non-radio active isotope containing drugs, such as deuterated drugs called "heavy drugs" can be used for the treatment of diseases and conditions related to URAT1 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-isotopic compound.

1. A compound of formula (I):

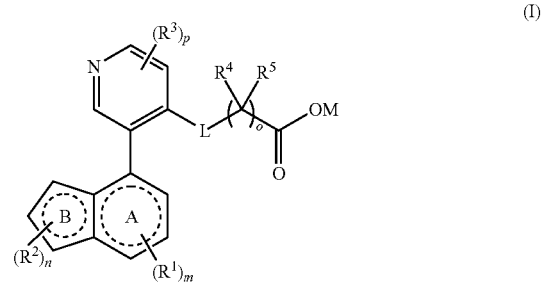

(I)

or a pharmaceutically acceptable salt thereof,
wherein:
A-B is an indolizine system, which is selected from:

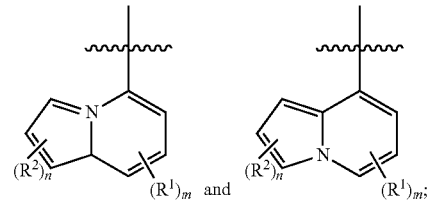

L is selected from $NR^{X}$, O and S;
each $R^1$ is independently selected from hydrogen, hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, —CN, —NO$_2$, —NR$^{A1}$R$^{B1}$, —OR$^{A1}$, —S(O)$_r$R$^{A1}$, —S(O)$_2$OR$^{A1}$, —OS(O)$_2$R$^{A1}$, —P(O)R$^{A1}$R$^{B1}$, —P(O)(OR$^{A1}$)(OR$^{B1}$), —C(O)R$^{A1}$, —C(O)OR$^{A1}$, —OC(O)R$^{A1}$, —C(O)NR$^{A1}$R$^{B1}$, NR$^{A1}$C(O)R$^{B1}$, —OC(O)NR$^{A1}$R$^{B1}$, —NR$^{A1}$C(O)OR$^{B1}$, —NR$^{A1}$C(O)NR$^{A1}$R$^{B1}$, —NR$^{A1}$C(S)NR$^{A1}$R$^{B1}$, —S(O)$_r$NR$^{A1}$R$^{B1}$, —NR$^{A1}$S(O)$_r$R$^{B1}$, —NR$^{A1}$S(O)$_2$NR$^{A1}$R$^{B1}$, —S(O)(=NR$^{E1}$)R$^{B1}$, —N=S(O)R$^{A1}$R$^{B1}$, —NR$^{A1}$S(O)(=NR$^{E1}$)R$^{B1}$, —S(O)(=NR$^{E1}$)NR$^{A1}$R$^{B1}$, —NR$^{A1}$S(O)(=NR$^{E1}$)NR$^{A1}$R$^{B1}$, —C(=NR$^{E1}$)R$^{A1}$, —C(=N—OR$^{B1}$)R$^{A1}$, —C(=NR$^{E1}$)NR$^{A1}$R$^{B1}$, —NR$^{A1}$C(=NR$^{E1}$)R$^{B1}$, and —NR$^{A1}$C(=NR$^{E1}$)NR$^{A1}$R$^{B1}$, wherein alkyl, alkenyl, alkynyl, cycloalkyl, heterocyclyl, aryl and heteroaryl are each unsubstituted or substituted with at least one substituent, such as one, two, three, or four substituents, independently selected from R$^X$;

each R$^2$ is independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, —CN, —NO$_2$, —NR$^{A2}$R$^{B2}$, —OR$^{A2}$, —S(O)$_r$R$^{A2}$, —S(O)$_2$OR$^{A2}$, —OS(O)$_2$R$^{A2}$, —P(O)R$^{A2}$R$^{B2}$, —P(O)(OR$^{A2}$)(OR$^{B2}$), —C(O)R$^{A2}$, —C(O)OR$^{A2}$, —OC(O)R$^{A2}$, —C(O)NR$^{A2}$R$^{B2}$, NR$^{A2}$C(O)R$^{B2}$, —OC(O)NR$^{A2}$R$^{B2}$, —NR$^{A2}$C(O)OR$^{B2}$, —NR$^{A2}$C(O)NR$^{A2}$R$^{B2}$, —NR$^{A2}$C(S)NR$^{A2}$R$^{B2}$, —S(O)$_r$NR$^{A2}$R$^{B2}$, NR$^{A2}$S(O)$_r$R$^{B2}$, —NR$^{A2}$S(O)$_2$R$^{A2}$R$^{B2}$, S(O)(=NR$^{E2}$)R$^{B2}$, —N=S(O)R$^{A2}$R$^{B2}$, —NR$^{A2}$S(O)(=NR$^{E2}$)R$^{B2}$, S(O)(=NR$^{E2}$)NR$^{A2}$R$^{B2}$, —NR$^{A2}$S(O)(=NR$^{E2}$)NR$^{A2}$R$^{B2}$, —C(=NR$^{E2}$)R$^{A2}$, —C(=N—OR$^{B2}$)R$^{A2}$, —C(=NR$^{E2}$)NR$^{A2}$R$^{B2}$, —NR$^{A2}$C(=NR$^{E2}$)R$^{B2}$, and —NR$^{A2}$C(=NR$^{E2}$)NR$^{A2}$R$^{B2}$, wherein alkyl, alkenyl, alkynyl, cycloalkyl, heterocyclyl, aryl and heteroaryl are each unsubstituted or substituted with at least one substituent, such as one, two, three, or four substituents, independently selected from R$^X$;

each R$^3$ is independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, —CN, —NO$_2$, —NR$^{A3}$R$^{B3}$, —OR$^{A3}$, —S(O)$_r$R$^{A3}$, —S(O)$_2$OR$^{A3}$, —OS(O)$_2$R$^{A3}$, —P(O)R$^{A3}$R$^{B3}$, —P(O)(OR$^{A3}$)(OR$^{B3}$), —C(O)R$^{A3}$, —C(O)OR$^{A3}$, —OC(O)R$^{A3}$, —C(O)NR$^{A3}$R$^{B3}$, —NR$^{A3}$C(O)R$^{B3}$, —OC(O)NR$^{A3}$R$^{B3}$, —NR$^{A3}$C(O)OR$^{B3}$, NR$^{A3}$C(O)NR$^{A3}$R$^{B3}$, —NR$^{A3}$C(S)NR$^{A3}$R$^{B3}$, —S(O)$_r$NR$^{A3}$R$^{B3}$, NR$^{A3}$S(O)$_r$R$^{B3}$, NR$^{A3}$S(O)$_2$NR$^{A3}$R$^{B3}$, —S(O)(=NR$^{E3}$)R$^{B3}$, —N=S(O)R$^{A3}$R$^{B3}$, —NR$^{A3}$S(O)(=NR$^{E3}$)R$^{B3}$, —S(O)(=NR$^{E3}$)NR$^{A3}$R$^{B3}$, —NR$^{A3}$S(O)(=NR$^{E3}$)NR$^{A3}$R$^{B3}$, —C(=NR$^{E3}$)R$^{A3}$, —C(=N—OR$^{B3}$)R$^{A3}$, C(=NR$^{E3}$)NR$^{A3}$R$^{B3}$, NR$^{A3}$C(=NR$^{E3}$)R$^{B3}$, and —NR$^{A3}$C(=NR$^{E3}$)NR$^{A3}$R$^{B3}$, wherein alkyl, alkenyl, alkynyl, cycloalkyl, heterocyclyl, aryl and heteroaryl are each unsubstituted or substituted with at least one substituent, such as one, two, three, or four substituents, independently selected from R$^X$;

each R$^4$ and R$^5$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, wherein the said alkyl, cycloalkyl and heterocyclyl is unsubstituted or substituted with at least one substituent, such as one, two, three, or four substituents, independently selected from R$^X$;

or R$^4$ and R$^5$ together with the carbon atom to which they are attached form a ring of 3 to 7 members containing 0, 1, or 2 heteroatoms independently selected from oxygen, sulfur and nitrogen, and optionally substituted with 1, 2 or 3 R$^X$ groups;

each R$^{A1}$, R$^{A2}$, R$^{A3}$, R$^{B1}$, R$^{B2}$ and R$^{B3}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three, or four substituents, independently selected from R$^X$;

or each "R$^{A1}$ and R$^{B1}$", "R$^{A2}$ and R$^{B2}$", or "R$^{A3}$ and R$^{B3}$" together with the atom(s) to which they are attached form a heterocyclic ring of 4 to 12 members containing 0, 1, or 2 additional heteroatoms independently selected from oxygen, sulfur, nitrogen and phosphorus, and optionally substituted with 1, 2 or 3 R$^X$ groups;

each R$^{E1}$, R$^{E2}$ and R$^{E3}$ are independently selected from hydrogen, $C_{1-10}$ alkyl, CN, NO$_2$, OR$^{a1}$, SR$^{a1}$, —S(O)$_r$R$^{a1}$, —S(O)$_r$NR$^{a1}$R$^{b1}$, —C(O)R$^{a1}$, —C(O)OR$^{a1}$, and —C(O)NR$^{a1}$R$^{b1}$; each R$^X$ is independently selected from $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, halogen, —CN, —NO$_2$, —(CR$^{c1}$R$^{d1}$)$_t$NR$^{a1}$R$^{b1}$, —(CR$^{c1}$R$^{d1}$)$_t$OR$^{b1}$, —(CR$^{c1}$R$^{d1}$)$_t$S(O)$_r$R$^{b1}$, —(CR$^{c1}$R$^{d1}$)$_t$S(O)$_2$OR$^{b1}$, —(CR$^{c1}$R$^{d1}$)$_t$OS(O)$_2$R$^{b1}$, —(CR$^{c1}$R$^{d1}$)$_t$P(O)R$^{a1}$R$^{b1}$, —(CR$^{c1}$R$^{d1}$)$_t$P(O)(OR$^{a1}$)(OR$^{b1}$), —(CR$^{c1}$R$^{d1}$)$_t$C(O)R$^{a1}$, —(CR$^{c1}$R$^{d1}$)$_t$C(O)OR$^{b1}$, —(CR$^{c1}$R$^{d1}$)$_t$OC(O)R$^{b1}$, —(CR$^{c1}$R$^{d1}$)$_t$C(O)NR$^{a1}$R$^{b1}$, —(CR$^{c1}$R$^{d1}$)$_t$NR$^{a1}$C(O)R$^{b1}$, —(CR$^{c1}$R$^{d1}$)$_t$OC(O)NR$^{a1}$R$^{b1}$, —(CR$^{c1}$R$^{d1}$)$_t$NR$^{a1}$C(O)OR$^{b1}$, —(CR$^{c1}$R$^{d1}$)$_t$NR$^{a1}$C(O)R$^{b1}$, —(CR$^{c1}$R$^{d1}$)$_t$NR$^{a1}$C(S)NR$^{a1}$R$^{b1}$, —(CR$^{c1}$R$^{d1}$)$_t$S(O)$_r$NR$^{a1}$R$^{b1}$, —(CR$^{c1}$R$^{d1}$)$_t$NR$^{a1}$S(O)$_r$R$^{b1}$, —(CR$^{c1}$R$^{d1}$)$_t$NR$^{a1}$S(O)$_2$NR$^{a1}$R$^{b1}$, —(CR$^{c1}$R$^{d1}$)$_t$S(O)(=NR$^{e1}$)R$^{b1}$, —(CR$^{c1}$R$^{d1}$)$_t$N=S(O)R$^{a1}$R$^{b1}$, —(CR$^{c1}$R$^{d1}$)$_t$NR$^{a1}$S(O)(=NR$^{e1}$)R$^{b1}$, —(CR$^{c1}$R$^{d1}$)$_t$S(O)(=NR$^{e1}$)NR$^{a1}$R$^{b1}$, —(CR$^{c1}$R$^{d1}$)$_t$NR$^{a1}$S(O)(=NR$^{e1}$)NR$^{a1}$R$^{b1}$, —(CR$^{c1}$R$^{d1}$)$_t$C(=NR$^{e1}$)R$^{a1}$, —(CR$^{c1}$R$^{d1}$)$_t$C(=N—OR$^{b1}$)R$^{a1}$, —(CR$^{c1}$R$^{d1}$)$_t$C(=NR$^{e1}$)NR$^{a1}$R$^{b1}$, —(CR$^{c1}$R$^{d1}$)$_t$NR$^{a1}$C(=NR)R$^{b1}$, and —(CR$^{c1}$R$^{d1}$)$_t$NR$^{a1}$C(=NR)NR$^{e1}$R$^{a1}$R$^{b1}$, wherein alkyl, alkenyl, alkynyl, cycloalkyl, heterocyclyl, aryl and heteroaryl are each unsubstituted or substituted with at least one substituent, such as one, two, three, or four substituents, independently selected from R$^Y$;

each R$^{a1}$ and each R$^{b1}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three, or four substituents, independently selected from R$^Y$;

or R$^{a1}$ and R$^{b1}$ together with the atom(s) to which they are attached form a heterocyclic ring of 4 to 12 members containing 0, 1, or 2 additional heteroatoms independently selected from oxygen, sulfur, nitrogen and phosphorus, and optionally substituted with 1, 2, or 3 R$^Y$ groups; each R$^{c1}$ and each R$^{d1}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three, or four substituents, independently selected from R$^Y$;

or $R^{c1}$ and $R^{d1}$ together with the carbon atom(s) to which they are attached form a ring of 3 to 12 members containing 0, 1, or 2 heteroatoms independently selected from oxygen, sulfur and nitrogen, and optionally substituted with 1, 2, or 3 $R^Y$ groups;

each $R^{e1}$ is independently selected from hydrogen, $C_{1-10}$ alkyl, $C_{3-10}$ cycloalkyl, $C_{3-10}$ cycloalkyl-$C_{1-4}$ alkyl, CN, $NO_2$, $OR^{a2}$, $SR^{a2}$, —S(O)$_r$$R^{a2}$, —S(O)$_r$$NR^{a2}R^{b2}$, —C(O)$R^{a2}$, —C(O)O$R^{a2}$, and —C(O)N$R^{a2}R^{b2}$;

$R^Y$ is independently selected from $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, halogen, —CN, —$NO_2$, —(C$R^{c2}R^{d2}$)$_t$N$R^{a2}R^{b2}$, —(C$R^{c2}R^{d2}$)$_t$O$R^{b2}$, —(C$R^{c2}R^{d2}$)$_t$S(O)$_r$$R^{b2}$, —(C$R^{c2}R^{d2}$)$_t$S(O)$_2$O$R^{b2}$, —(C$R^{c2}R^{d2}$)$_t$OS(O)$_2$$R^{b2}$, —(C$R^{c2}R^{d2}$)$_t$P(O)$R^{a2}R^{b2}$, —(C$R^{c2}R^{d2}$)$_t$P(O)(O$R^{a2}$)(O$R^{b2}$), —(C$R^{c2}R^{d2}$)$_t$C(O)$R^{a2}$, —(C$R^{c2}R^{d2}$)$_t$C(O)O$R^{b2}$, —(C$R^{c2}R^{d2}$)$_t$OC(O)$R^{b2}$, —(C$R^{c2}R^{d2}$)$_t$C(O)N$R^{a2}R^{b2}$, —(C$R^{c2}R^{d2}$)$_t$N$R^{a2}$C(O)$R^{b2}$, —(C$R^{c2}R^{d2}$)$_t$OC(O)N$R^{a2}R^{b2}$, —(C$R^{c2}R^{d2}$)$_t$N$R^{a2}$C(O)O$R^{b2}$, —(C$R^{c2}R^{d2}$)$_t$N$R^{a2}$C(O)N$R^{a2}R^{b2}$, —(C$R^{c2}R^{d2}$)$_t$N$R^{a2}$C(S)N$R^{a2}R^{b2}$, —(C$R^{c2}R^{d2}$)$_t$S(O)$_r$N$R^{a2}R^{b2}$, —(C$R^{c2}R^{d2}$)$_t$N$R^{a2}$S(O)$_r$$R^{b2}$, —(C$R^{c2}R^{d2}$)$_t$N$R^{a2}$S(O)$_2$N$R^{a2}R^{b2}$, —(C$R^{c2}R^{d2}$)$_t$S(O)(=N$R^{e2}$)$R^{b2}$, —(C$R^{c2}R^{d2}$)$_t$N=S(O)$R^{a2}R^{b2}$, —(C$R^{c2}R^{d2}$)$_t$N$R^{a2}$S(O)(=N$R^{e2}$)$R^{b2}$, —(C$R^{c2}R^{d2}$)$_t$S(O)(=N$R^{e2}$)N$R^{a2}R^{b2}$, —(C$R^{c2}R^{d2}$)$_t$N$R^{a2}$S(O)(=$R^{e2}$)N$R^{a2}R^{b2}$, (C$R^{c2}R^{d2}$)$_t$C(=N$R^{e2}$)$R^{a2}$, —(C$R^{c2}R^{d2}$)$_t$C(=N—O$R^{b2}$)$R^{a2}$, —(C$R^{c2}R^{d2}$)$_t$C(=N$R^{e2}$)N$R^{a2}R^{b2}$, —(C$R^{c2}R^{d2}$)$_t$N$R^{a2}$C(=N$R^{e2}$)$R^{b2}$, and —(C$R^{c2}R^{d2}$)$_t$N$R^{a2}$C(=N$R^{e2}$)N$R^{a2}R^{b2}$, wherein alkyl, alkenyl, alkynyl, cycloalkyl, heterocyclyl, aryl and heteroaryl are each unsubstituted or substituted with at least one substituent, such as one, two, three, or four substituents, independently selected from OH, CN, amino, halogen, $C_{1-10}$ alkyl, $C_{2-10}$ alkenyl, $C_{2-10}$ alkynyl, $C_{3-10}$ cycloalkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino and di($C_{1-10}$ alkyl)amino;

each $R^{a2}$ and each $R^{b2}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$alkylthio, $C_{3-10}$ cycloalkylthio, $C_{1-10}$ alkylamino, $C_{3-10}$ cycloalkylamino, di($C_{1-10}$ alkyl)amino, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, such as one, two, three, or four substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$alkylamino, $C_{3-10}$ cycloalkylamino and di($C_{1-10}$ alkyl)amino;

or $R^{a2}$ and $R^{b2}$ together with the atom(s) to which they are attached form a heterocyclic ring of 4 to 12 members containing 0, 1, or 2 additional heteroatoms independently selected from oxygen, sulfur, nitrogen and phosphorus, and optionally substituted with 1 or 2 substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$alkylamino, $C_{3-10}$ cycloalkylamino and di($C_{1-10}$ alkyl)amino;

each $R^{c2}$ and each $R^{d2}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl) amino, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, such as one, two, three, or four substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

or $R^{c2}$ and $R^{d2}$ together with the carbon atom(s) to which they are attached form a ring of 3 to 12 members containing 0, 1, or 2 heteroatoms independently selected from oxygen, sulfur and nitrogen, and optionally substituted with 1 or 2 substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{e2}$ is independently selected from hydrogen, CN, $NO_2$, $C_{1-10}$ alkyl, $C_{3-10}$ cycloalkyl, $C_{3-10}$ cycloalkyl-$C_{1-4}$ alkyl, $C_{1-10}$ alkoxy, $C_{3-10}$ cycloalkoxy, —C(O)$C_{1-4}$ alkyl, —C(O)$C_{3-10}$ cycloalkyl, —C(O)O$C_{1-4}$ alkyl, —C(O)O$C_{3-10}$ cycloalkyl, —C(O)$NH_2$, —C(O)NH($C_{1-4}$ alkyl), —C(O)N($C_{1-4}$ alkyl)$_2$, —C(O)NH($C_{3-10}$ cycloalkyl), —C(O)N($C_{3-10}$ cycloalkyl)$_2$, —S(O)$_2$$C_{1-4}$ alkyl, —S(O)$_2$$C_{3-10}$ cycloalkyl, —S(O)$_2$$NH_2$, —S(O)$_2$NH($C_{1-4}$ alkyl), —S(O)$_2$N($C_{1-4}$ alkyl)$_2$, —S(O)$_2$NH($C_{3-10}$ cycloalkyl) and —S(O)$_2$N($C_{3-10}$ cycloalkyl)$_2$;

M is hydrogen, $C_{1-4}$ alkyl or a pharmaceutically acceptable cation;

m is independently selected from 0, 1, 2 and 3;
n is independently selected from 0, 1, 2, and 3;
o is selected from 1, 2, and 3;
p is independently selected from 0, 1, 2 and 3;
each r is independently selected from 0, 1 and 2;
each t is independently selected from 0, 1, 2, 3 and 4.

2. A compound of 1 or a pharmaceutically acceptable salt thereof, wherein A-B is.

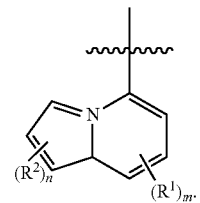

3. A compound of 1 or a pharmaceutically acceptable salt thereof, wherein A-B is.

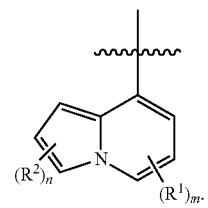

4. A compound of any one of 1 to 3 or a pharmaceutically acceptable salt thereof, wherein L is selected from O and S.

5. A compound of 4 or a pharmaceutically acceptable salt thereof, wherein L is S.

6. A compound of any one of 1 to 5 or a pharmaceutically acceptable salt thereof, wherein $R^4$ and $R^5$ are independently selected from $C_{1-10}$ alkyl, and optionally substituted with 1, 2 or 3 $R^X$ groups, or $R^4$ and $R^5$ together with the carbon atom to which they are attached form a ring of 3 to 7 members containing 0, 1, or 2 heteroatoms independently selected from oxygen, sulfur and nitrogen, and optionally substituted with 1, 2 or 3 $R^X$ groups.

7. A compound of 6 or a pharmaceutically acceptable salt thereof, wherein $R^4$ and $R^5$ together with the carbon atom to which they are attached form cyclopropyl, cyclobutyl, cyclopentyl or cyclohexyl, and optionally substituted with 1, 2 or 3 $R^X$ groups.

8. A compound of 7 or a pharmaceutically acceptable salt thereof, wherein $R^4$ and $R^5$ together with the carbon atom to which they are attached form cyclobutyl, and optionally substituted with 1, 2 or 3 halogen, $C_{1-10}$ alkyl, OH, or $C_{1-10}$ alkoxy.

9. A compound of 8 or a pharmaceutically acceptable salt thereof, wherein $R^4$ and $R^5$ together with the carbon atom to which they are attached form cyclobutyl, and optionally substituted with 1, 2 or 3 F, methyl, OH, or $OCH_3$.

10. A compound of 6 or a pharmaceutically acceptable salt thereof, wherein $R^4$ and $R^5$ are methyl, and optionally substituted with 1, 2 or 3 $R^X$ groups.

11. A compound of 10 or a pharmaceutically acceptable salt thereof, wherein $R^4$ and $R^5$ are methyl, and optionally substituted with 1, 2 or 3 OH, $OCH_3$ or F.

12. A compound of any one of 1 to 11 or a pharmaceutically acceptable salt thereof, wherein $R^1$ is CN and m is 1.

13. A compound of any one of 1 to 12 or a pharmaceutically acceptable salt thereof, wherein each $R^2$ is independently selected from hydrogen, halogen, CN, $C_{1-10}$ alkyl, $C_{3-10}$ cycloalkyl, and $-(CR^{C1}R^{D1})_nS(O)_rR^{A1}$ and n is 1 or 2.

14. A compound of 13 or a pharmaceutically acceptable salt thereof, wherein each $R^2$ is independently selected from hydrogen, fluorine, chlorine, bromine, methyl, $CF_3$, CN and $SO_2CH_3$.

15. A compound of any one of 1 to 14 or a pharmaceutically acceptable salt thereof, wherein $R^3$ is hydrogen.

16. A compound of any one of 1 to 15 or a pharmaceutically acceptable salt thereof, wherein M is selected from hydrogen, $C_{1-4}$ alkyl, and a pharmaceutically acceptable cation. Preferably the pharmaceutically acceptable cation is $Na^+$, $Li^+$, $K^+$, $Ca^{2+}$, $Mg^{2+}$, $NH^{4+}$, tetramethylammonium, tetraethylammonium, methylamino, dimethylamino, trimethylamine or triethylamino.

17. A compound of 16 or a pharmaceutically acceptable salt thereof, wherein M is hydrogen.

18. A compound, selected from
1-((3-(8-cyanoindolizin-5-yl)pyridin-4-yl)thio)cyclobutane-1-carboxylic acid,
2-((3-(8-cyanoindolizin-5-yl)pyridin-4-yl)thio)-2-methylpropanoic acid,
2-((3-(3-chloro-8-cyanoindolizin-5-yl)pyridin-4-yl)thio)-2-methylpropanoic acid,
2-((3-(1-chloro-8-cyanoindolizin-5-yl)pyridin-4-yl)thio)-2-methylpropanoic acid,
1-((3-(8-cyano-2-methylindolizin-5-yl)pyridin-4-yl)thio)cyclobutane-1-carboxylic acid,
2-((3-(8-cyano-2-methylindolizin-5-yl)pyridin-4-yl)thio)-2-methylpropanoic acid,
1-((3-(8-cyano-2-(trifluoromethyl)indolizin-5-yl)pyridin-4-yl)thio)cyclobutane-1-carboxylic acid,
1-((3-(5-cyanoindolizin-8-yl)pyridin-4-yl)thio)cyclobutane-1-carboxylic acid,
2-((3-(5-cyanoindolizin-8-yl)pyridin-4-yl)thio)-2-methylpropanoic acid,
1-((3-(3-chloro-5-cyanoindolizin-8-yl)pyridin-4-yl)thio)cyclobutane-1-carboxylic acid,
1-((3-(2-chloro-5-cyanoindolizin-8-yl)pyridin-4-yl)thio)cyclobutane-1-carboxylic acid,
1-((3-(5-cyano-2-fluoroindolizin-8-yl)pyridin-4-yl)thio)cyclobutane-1-carboxylic acid,
1-((3-(2-chloro-8-cyanoindolizin-5-yl)pyridin-4-yl)thio)cyclobutane-1-carboxylic acid,
2-((3-(2-chloro-8-cyanoindolizin-5-yl)pyridin-4-yl)thio)-2-methylpropanoic acid,
1-((3-(2-bromo-8-cyanoindolizin-5-yl)pyridin-4-yl)thio)cyclobutane-1-carboxylic acid,
2-((3-(2-bromo-8-cyanoindolizin-5-yl)pyridin-4-yl)thio)-2-methylpropanoic acid,
1-((3-(2,8-dicyanoindolizin-5-yl)pyridin-4-yl)thio)cyclobutane-1-carboxylic acid,
2-((3-(2,8-dicyanoindolizin-5-yl)pyridin-4-yl)thio)-2-methylpropanoic acid,
1-((3-(8-cyano-2-(methylsulfonyl)indolizin-5-yl)pyridin-4-yl)thio)cyclobutane-1-carboxylic acid,
1-((3-(8-cyano-3-fluoroindolizin-5-yl)pyridin-4-yl)thio)cyclobutane-1-carboxylic acid,
1-((3-(8-cyano-1-fluoroindolizin-5-yl)pyridin-4-yl)thio)cyclobutane-1-carboxylic acid,
1-((3-(8-cyano-1,3-difluoroindolizin-5-yl)pyridin-4-yl)thio)cyclobutane-1-carboxylic acid,
1-((3-(3-chloro-8-cyanoindolizin-5-yl)pyridin-4-yl)thio)cyclobutane-1-carboxylic acid,
1-((3-(1-chloro-8-cyanoindolizin-5-yl)pyridin-4-yl)thio)cyclobutane-1-carboxylic acid,
1-((3-(8-cyanoindolizin-5-yl)pyridin-4-yl)thio)-3-hydroxycyclobutane-1-carboxylic acid,
1-((3-(8-cyanoindolizin-5-yl)pyridin-4-yl)thio)-3-hydroxy-3-methylcyclobutane-1-carboxylic acid,
1-((3-(8-cyanoindolizin-5-yl)pyridin-4-yl)thio)-3-methoxycyclobutane-1-carboxylic acid,
1-((3-(8-cyanoindolizin-5-yl)pyridin-4-yl)thio)-3-fluorocyclobutane-1-carboxylic acid,
1-((3-(8-cyanoindolizin-5-yl)pyridin-4-yl)thio)-3,3-difluorocyclobutane-1-carboxylic acid,
2-((3-(8-cyanoindolizin-5-yl)pyridin-4-yl)thio)-3-hydroxy-2-methylpropanoic acid,
2-((3-(8-cyanoindolizin-5-yl)pyridin-4-yl)thio)-3-methoxy-2-methylpropanoic acid,
2-((3-(8-cyanoindolizin-5-yl)pyridin-4-yl)thio)-3-fluoro-2-methylpropanoic acid,
2-((3-(8-cyanoindolizin-5-yl)pyridin-4-yl)thio)-3,3-difluoro-2-methylpropanoic acid,
2-((3-(8-cyanoindolizin-5-yl)pyridin-4-yl)thio)-3,3,3-trifluoro-2-methylpropanoic acid,
or pharmaceutically acceptable salts thereof.

In another of its aspects, provided is a pharmaceutical composition comprising a compound disclosed herein, or a pharmaceutically acceptable salts thereof.

In yet another of its aspects, provided is a kit comprising a compound disclosed herein, or a pharmaceutically acceptable salts thereof; and instructions which comprise one or more forms of information selected from the group consisting of indicating a disease state for which the composition is to be administered, storage information for the composition, dosing information and instructions regarding how to administer the composition. In one particular variation, the kit comprises the compound in a multiple dose form.

In still another of its aspects, there is provided an article of manufacture comprising a compound disclosed herein, or a pharmaceutically acceptable salts thereof; and packaging materials. In one variation, the packaging material comprises a container for housing the compound. In one particular variation, the container comprises a label indicating one or more members of the group consisting of a disease state for which the compound is to be administered, storage information, dosing information and/or instructions regarding how to administer the compound. In another variation, the article of manufacture comprises the compound in a multiple dose form.

In a further of its aspects, there is provided a therapeutic method comprising administering a compound disclosed herein, or a pharmaceutically acceptable salts thereof to a subject.

In another of its aspects, there is provided a method of inhibiting URAT1 comprising contacting the URAT1 with a compound disclosed herein, or a pharmaceutically acceptable salts thereof.

In yet another of its aspects, there is provided a method of inhibiting URAT1 comprising causing a compound disclosed herein, or a pharmaceutically acceptable salts thereof, to be present in a subject in order to inhibit the URAT1 in vivo.

In a further of its aspects, there is provided a method of inhibiting URAT1 comprising administering a first compound to a subject that is converted in vivo to a second compound wherein the second compound inhibits the URAT1 in vivo, the second compound being a compound disclosed herein, or a pharmaceutically acceptable salts thereof.

In another of its aspects, there is provided a method of treating a disease state for which URAT1 possesses activity that contributes to the pathology and/or symptomology of the disease state, the method comprising causing a compound disclosed herein, or a pharmaceutically acceptable salts thereof, to be present in a subject in a therapeutically effective amount for the disease state.

In a further of its aspects, there is provided a method of treating a disease state for which URAT1 possesses activity that contributes to the pathology and/or symptomology of the disease state, the method comprising administering a first compound to a subject that is converted in vivo to a second compound wherein the second compound inhibits the PI3K in vivo. It is noted that the compounds of the present invention may be the first or second compounds.

In one variation of each of the above methods the disease state is selected from the group consisting of hyperuricaemia, gout, a recurrent gout attach, tophaceous gout, arthritis, gouty arthritis, inflammatory arthritis, joint inflammation, deposition of urate crystals in the joint, kidney disease, kidney stones, kidney failure, urolithiasis, hypertension, a cardiovascular disease, coronary heart disease, Lesch-Nyhan syndrome, Kelley-Seegmiller syndrome, urolithiasis, plumbism, hyperparathyroidism, psoriasis, sarcoidosis, and hypoxanthine-guanine phosphoribosyltransferase (HPRT) deficiency or a combination thereof.

In another of its aspects, there is provided a method of treating a disease state characterized by abnormal tissue or organ levels of uric acid for which activity of URAT1 contributes to the pathology and/or symptomology of the disease state including but not limited to, for example, goat, hyperuricaemia.

In still another of its aspects, the present invention relates to the use of a compound disclosed herein as a medicament. In yet another of its aspects, the present invention relates to the use of a compound disclosed herein, or a pharmaceutically acceptable salts thereof, in the manufacture of a medicament for inhibiting URAT1.

In a further of its aspects, the present invention relates to the use of a compound disclosed herein, or a pharmaceutically acceptable salts thereof, in the manufacture of a medicament for treating a condition characterized by abnormal tissue or organ levels of uric acid for which a URAT1 possesses activity that contributes to the pathology and/or symptomology of the disease state.

Administration and Pharmaceutical Compositions

In general, compounds of the disclosure will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors known to those of ordinary skill in the art. For example, for the treatment of neoplastic diseases and immune system disorders, the required dosage will also vary depending on the mode of administration, the particular condition to be treated and the effect desired.

In general, satisfactory results are indicated to be obtained systemically at daily dosages of from about 0.001 to about 100 mg/kg per body weight, or particularly, from about 0.03 to 2.5 mg/kg per body weight. An indicated daily dosage in the larger mammal, e.g. humans, may be in the range from about 0.5 mg to about 2000 mg, or more particularly, from about 0.5 mg to about 1000 mg, conveniently administered, for example, in divided doses up to four times a day or in retard form. Suitable unit dosage forms for oral administration comprise from ca. 1 to 50 mg active ingredient.

Compounds of the disclosure may be administered as pharmaceutical compositions by any conventional route; for example, enterally, e.g., orally, e.g., in the form of tablets or capsules; parenterally, e.g., in the form of injectable solutions or suspensions; or topically, e.g., in the form of lotions, gels, ointments or creams, or in a nasal or suppository form.

Pharmaceutical compositions comprising a compound of the present disclosure in free form or in a pharmaceutically acceptable salt form in association with at least one pharmaceutically acceptable carrier or diluent may be manufactured in a conventional manner by mixing, granulating, coating, dissolving or lyophilizing processes. For example, pharmaceutical compositions comprising a compound of the disclosure in association with at least one pharmaceutical acceptable carrier or diluent may be manufactured in conventional manner by mixing with a pharmaceutically acceptable carrier or diluent. Unit dosage forms for oral administration contain, for example, from about 0.1 mg to about 1000 mg of active substance.

In one embodiment, the pharmaceutical compositions are solutions of the active ingredient, including suspensions or dispersions, such as isotonic aqueous solutions. In the case of lyophilized compositions comprising the active ingredient alone or together with a carrier such as mannitol, dispersions or suspensions can be made up before use. The pharmaceutical compositions may be sterilized and/or contain adjuvants, such as preserving, stabilizing, wetting or emulsifying agents, solution promoters, salts for regulating the osmotic pressure and/or buffers. Suitable preservatives include but are not limited to antioxidants such as ascorbic acid, or microbicides, such as sorbic acid or benzoic acid.

The solutions or suspensions may further comprise viscosity-increasing agents, including but not limited to, sodium carboxymethylcellulose, carboxymethylcellulose, dextran, polyvinylpyrrolidone, gelatins, or solubilizers, e.g. Tween 80 (polyoxyethylene(20)sorbitan mono-oleate).

Suspensions in oil may comprise as the oil component the vegetable, synthetic, or semi-synthetic oils customary for injection purposes. Examples include liquid fatty acid esters that contain as the acid component a long-chained fatty acid having from 8 to 22 carbon atoms, or in some embodiments, from 12 to 22 carbon atoms. Suitable liquid fatty acid esters include but are not limited to lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid and linoleic acid, and if desired, may contain antioxidants, for example vitamin E, 3-carotene or 3,5-di-tert-butyl-hydroxytoluene. The alcohol component of these fatty acid esters may have six carbon atoms and may be monovalent or polyvalent, for example a mono-, di- or trivalent, alcohol. Suitable alcohol components include but are not limited to methanol, ethanol, propanol, butanol or pentanol or isomers thereof; glycol and glycerol.

Other suitable fatty acid esters include but are not limited ethyl-oleate, isopropyl myristate, isopropyl palmitate, LABRAFIL® M 2375, (polyoxyethylene glycerol), LABRAFIL® M 1944 CS (unsaturated polyglycolized glycerides prepared by alcoholysis of apricot kernel oil and comprising glycerides and polyethylene glycol ester), LABRASOL™ (saturated polyglycolized glycerides prepared by alcoholysis of TCM and comprising glycerides and polyethylene glycol ester; all available from GaKefosse, France), and/or MIGLYOL® 812 (triglyceride of saturated fatty acids of chain length C8 to C12 from Hills AG, Germany), and vegetable oils such as cottonseed oil, almond oil, olive oil, castor oil, sesame oil, soybean oil, or groundnut oil.

Pharmaceutical compositions for oral administration may be obtained, for example, by combining the active ingredient with one or more solid carriers, and if desired, granulating a resulting mixture, and processing the mixture or granules by the inclusion of additional excipients, to form tablets or tablet cores.

Suitable carriers as used herein, refers to relatively nontoxic chemical compounds or agents that facilitate the incorporation of a compound into cells or tissues, which include but are not limited to fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the abovementioned starches, carboxymethyl starch, crosslinked polyvinylpyrrolidone, alginic acid or a salt thereof, such as sodium alginate. Additional excipients include flow conditioners and lubricants, for example silicic acid, talc, stearic acid or salts thereof, such as magnesium or calcium stearate, and/or polyethylene glycol, or derivatives thereof.

Tablet cores may be provided with suitable, optionally enteric, coatings through the use of, inter alia, concentrated sugar solutions which may comprise gum arable, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or tablet coatings, for example for identification purposes or to indicate different doses of active ingredient.

Pharmaceutical compositions for oral administration may also include hard capsules comprising gelatin or soft-sealed capsules comprising gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient may be dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories comprising a combination of the active ingredient and a suppository base. Suitable suppository bases are, for example, natural or synthetic triglycerides, paraffin hydrocarbons, polyethylene glycols or higher alkanols.

Pharmaceutical compositions suitable for parenteral administration may comprise aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers. The active ingredient, optionally together with excipients, can also be in the form of a lyophilizate and can be made into a solution before parenteral administration by the addition of suitable solvents. Solutions such as are used, for example, for parenteral administration can also be employed as infusion solutions. The manufacture of injectable preparations is usually carried out under sterile conditions, as is the filling, for example, into ampoules or vials, and the sealing of the containers.

The disclosure also provides for a pharmaceutical combinations, e.g. a kit, comprising a) a first agent which is a compound disclosed herein, in free form or in pharmaceutically acceptable salt form, and b) at least one co-agent. The kit can comprise instructions for its administration.

Combination Therapies

The compounds or pharmaceutical acceptable salts of the disclosure may be administered as the sole therapy, or together with other therapeutic agent or agents.

For example, the therapeutic effectiveness of one of the compounds described herein may be enhanced by administration of an adjuvant (i.e. by itself the adjuvant may only have minimal therapeutic benefit, but in combination with another therapeutic agent, the overall therapeutic benefit to the individual is enhanced). Or, by way of example only, the benefit experienced by an individual may be increased by administering one of the compounds described herein with another therapeutic agent that also has therapeutic benefit. By way of example only, in a treatment for gout involving administration of one of the compounds described herein, increased therapeutic benefit may result by also providing the individual with another therapeutic agent for gout. Or, by way of example only, if one of the side effects experienced by an individual upon receiving one of the compounds described herein is nausea, then it may be appropriate to administer an anti-nausea agent in combination with the compound. Or, the additional therapy or therapies include, but are not limited to physiotherapy, psychotherapy, radiation therapy, application of compresses to a diseased area, rest, altered diet, and the like. Regardless of the disease, disorder or condition being treated, the overall benefit experienced by the individual may be additive of the two therapies or the individual may experience a synergistic benefit.

In the instances where the compounds described herein are administered in combination with other therapeutic agents, the compounds described herein may be administered in the same pharmaceutical composition as other therapeutic agents, or because of different physical and chemical characteristics, be administered by a different route. For example, the compounds described herein may be administered orally to generate and maintain good blood levels thereof, while the other therapeutic agent may be administered intravenously. Thus the compounds described herein may be administered concurrently, sequentially or dosed separately to other therapeutic agents.

For example, the compounds or pharmaceutical acceptable salts of the disclosure may be used in accordance with the disclosure in combination with pharmaceutical compositions effective in various diseases as described above. The one or more additional therapeutic agents may be selected from any of the agents or types of agent such as, a xanthine oxidase inhibitor (e.g. allopurinol, febuxostat or thiopurine); a xanthine oxidoreductase inhibitor (e.g. topiroxostat); a purine nucleoside phosphorylase (PNP) inhibitor (e.g. ulodesine); a uricase (e.g. pegloticase or rasburicase); a uricosuric agent, such as an agent that inhibits one or more transporters responsible for reabsorption of uric acid back into the blood, for example uric acid transporter inhibitors, such as another URAT1 inhibitor (e.g. benzbromarone, URC-102 or RDEA3170), a glucose transporter (GLUT) inhibitor, such as a GLUT-9 inhibitor, an organic anion transporter (OAT) inhibitor, such as an OAT-4 inhibitor, a solute carrier family 2 (facilitated glucose transporter), member 9 (SLC2A9) inhibitor, or an agent which inhibits one or more of the above transporters, such as benziodarone, isobromindione, probenecid, sulfinpyrazone, arhalofenate, tranilast, lesinurad or KUX-1151; an agent that otherwise exerts blood uric acid lowering effects, such as amlodipine, atorvastatin, fenofibrate or indomethacin; an anti-inflammatory drug such as nonsteroidal anti-inflammatory drugs (NSAIDs) (e.g. celecoxib), adrenocorticotropic hormone (ACTH), a glucocorticoid, colchicine, steroids, an interleukin 1 inhibitor (e.g. rilonacept) or an agent that modulates inflammation signaling cascades (e.g. an IRAK4 inhibitor); or an agent that reduces pain, such as acetaminophen, an ion channel modulator (e.g. an inhibitor of Nav1.7, TRPV1 or TRPM2).

In some embodiments, the additional agent is, an androgen, a COX-2 inhibitor, a PPAR agonist, naproxen, sevelamer, sibutramine, troglitazone, pioglitazone, another uric acid lowering agent, losartan, fibric acid, salicylate, vitamin C, or combinations thereof.

EXAMPLES

Various methods may be developed for synthesizing a compound of formula (I) or a pharmaceutically acceptable salt thereof. Representative methods for synthesizing a compound of formula (I) or a pharmaceutically acceptable salt thereof are provided in the Examples. It is noted, however, that a compound of formula (I) or a pharmaceutically acceptable salt thereof may also be synthesized by other synthetic routes that others may devise.

It will be readily recognized that certain compounds of formula (I) have atoms with linkages to other atoms that confer a particular stereochemistry to the compound (e.g., chiral centers). It is recognized that synthesis of a compound of formula (I) or a pharmaceutically acceptable salt thereof may result in the creation of mixtures of different stereoisomers (enantiomers, diastereomers). Unless a particular stereochemistry is specified, recitation of a compound is intended to encompass all of the different possible stereoisomers.

A compound of formula (I) can also be prepared as a pharmaceutically acceptable acid addition salt by, for example, reacting the free base form of a compound with a pharmaceutically acceptable inorganic or organic acid. Alternatively, a pharmaceutically acceptable base addition salt of a compound of formula (I) can be prepared by, for example, reacting the free acid form of a compound with a pharmaceutically acceptable inorganic or organic base. Inorganic and organic acids and bases suitable for the preparation of the pharmaceutically acceptable salts of compounds of formula (I) are set forth in the definitions section of this Application. Alternatively, the salt forms of the compounds of formula (I) can be prepared using salts of the starting materials or intermediates.

The free acid or free base forms of the compounds of formula (I) can be prepared from the corresponding base addition salt or acid addition salt form. For example, a compound of formula (I) in an acid addition salt form can be converted to the corresponding free base thereof by treating with a suitable base (e.g., ammonium hydroxide solution, sodium hydroxide, and the like). A compound of formula (I) in a base addition salt form can be converted to the corresponding free acid thereof by, for example, treating with a suitable acid (e.g., hydrochloric acid, etc).

The N-oxides of a compound of formula (I) or a pharmaceutically acceptable salt thereof can be prepared by methods known to those of ordinary skill in the art. For example, N-oxides can be prepared by treating an unoxidized form of the compound of formula (I) with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0 to 80° C. Alternatively, the N-oxides of the compounds of formula (I) can be prepared from the N-oxide of an appropriate starting material.

Compounds of formula (I) in an unoxidized form can be prepared from N-oxides of compounds of formula (I) by, for example, treating with a reducing agent (e.g., sulfur, sulfur dioxide, triphenyl phosphine, lithium borohydride, sodium borohydride, phosphorus trichloride, tribromide, and the like) in an suitable inert organic solvent (e.g., acetonitrile, ethanol, aqueous dioxane, and the like) at 0 to 80° C.

Protected derivatives of the compounds of formula (I) can be made by methods known to those of ordinary skill in the art. A detailed description of the techniques applicable to the creation of protecting groups and their removal can be found in T. W. Greene, Protecting Groups in Organic Synthesis, 3rd edition, John Wiley & Sons, Inc. 1999.

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. For example, the following abbreviations may be used in the examples and throughout the specification: g (grams); mg (milligrams); L (liters); mL (milliliters); μL (microliters); psi (pounds per square inch); M (molar); mM (millimolar); i.v. (intravenous); Hz (Hertz); MHz (megahertz); mol (moles); mmol (millimoles); RT (room temperature); min (minutes); h (hours); mp (melting point); TLC (thin layer chromatography); Rt (retention time); RP (reverse phase); MeOH (methanol); i-PrOH (isopropanol); TEA (triethylamine); TFA (trifluoroacetic acid); TFAA (trifluoroacetic anhydride); THF (tetrahydrofuran); DMSO (dimethyl sulfoxide); EtOAc (ethyl acetate); DME (1,2-dimethoxyethane); DCM (dichloromethane); DCE (dichloroethane); DMF (N,N-dimethylformamide); DMPU (N,N-dimethylpropyleneurea); CDI (1,1-carbonyldiimidazole); IBCF (isobutyl chloroformate); HOAc (acetic acid); HOSu (N-hydroxysuccinimide); HOBT (1-hydroxybenzotriazole); $Et_2O$ (diethyl ether); EDCI (1-(3-dimethylaminopropyl)-3-ethylcarbodiimide hydrochloride); BOC (tert-butyloxycarbonyl); FMOC (9-fluorenylmethoxycarbonyl); DCC (dicyclohexylcarbodiimide); CBZ (benzyloxycarbonyl); Ac (acetyl); atm (atmosphere); TMSE (2-(trimethylsilyl)ethyl); TMS (trimethylsilyl); TIPS (triisopropylsilyl); TBS (t-butyldimethylsilyl); DMAP (4-dimethylaminopyridine); Me (methyl); OMe (methoxy); Et (ethyl); tBu (tert-butyl); HPLC (high pressure liquid chomatography); BOP (bis(2-oxo-3-oxazolidinyl)phosphinic chloride); TBAF (tetra-n-butylammonium fluoride); m-CPBA (meta-chloroperbenzoic acid).

References to ether or $Et_2O$ are to diethyl ether; brine refers to a saturated aqueous solution of NaCl. Unless otherwise indicated, all temperatures are expressed in ° C. (degrees Centigrade). All reactions were conducted under an inert atmosphere at RT unless otherwise noted.

$^1$H NMR spectra were recorded on a Varian Mercury Plus 400. Chemical shifts are expressed in parts per million (ppm). Coupling constants are in units of hertz (Hz). Splitting patterns describe apparent multiplicities and are designated as s (singlet), d (doublet), t (triplet), q (quartet), m (multiplet), and br (broad).

Low-resolution mass spectra (MS) and compound purity data were acquired on a Shimadzu LC/MS single quadrapole system equipped with electrospray ionization (ESI) source, UV detector (220 and 254 nm), and evaporative light scattering detector (ELSD). Thin-layer chromatography was performed on 0.25 mm Superchemgroup silica gel plates (60F-254), visualized with UV light, 5% ethanolic phosphomolybdic acid, ninhydrin, or p-anisaldehyde solution. Flash column chromatography was performed on silica gel (200-300 mesh, Branch of Qingdao Haiyang Chemical Co., Ltd).

Synthetic Schemes

A compound of formula I or a pharmaceutically acceptable salt thereof may be synthesized according to a variety of reaction schemes. Some illustrative schemes are provided below and in the examples. Other reaction schemes could be readily devised by those skilled in the art in view of the present disclosure.

In the reactions described hereinafter it may be necessary to protect reactive functional groups, for example hydroxyl, amino, imino, thio or carboxyl groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Synthetic methods for preparing the compounds of the present disclosure are illustrated in the following Schemes and Examples. Starting materials are commercially available or may be made according to procedures known in the art or as illustrated herein.

The intermediates shown in the following schemes are either known in the literature or may be prepared by a variety of methods familiar to those skilled in the art.

As an illustration, one of the synthetic approach of the compounds of formula I of the present disclosure is outlined in Scheme 1. As shown in the Scheme, the compounds of formula I can be disassembled into the intermediates II to VI, which are either known in the literature or may be prepared by a variety of methods familiar to those skilled in the art. Coupling of bicyclic heteroaryl intermediates of formula V with pyridine intermediates of formula VI using transitional metal catalyzed coupling conditions such as Suzuki reaction or other coupling conditions known in the literature provides intermediates of formula IV. Conversion of intermediates of formula IV to intermediates of formula III can be readily achieved using methods known in the literature. Coupling of intermediates of formula III with intermediates of formula II provides compound of formula I through nucleophilic substitution reactions.

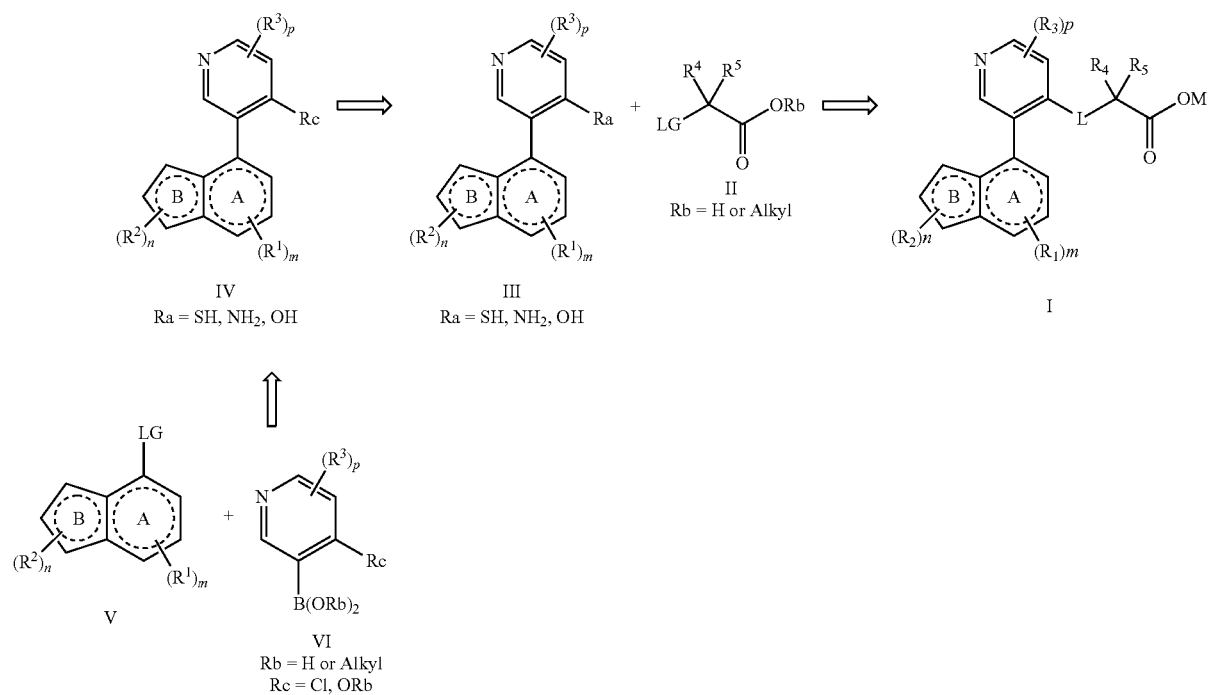

Scheme 1

As an illustration of the preparation of compounds of formula I, one synthetic route of compounds of formula Ia is shown in Scheme 2. Starting from 2-hydroxyl pyridine Ia-A, which is either commercially available or known in the literature, pyridone Ia-B can be readily prepared through N-alkylation or multi-step transformations known in the literature. Treatment of pyridone Ia-B with a base such as NaOEt in a protic solvent such as EtOH gives bicyclic heteroaryl Ia-C. Conversion of the hydroxyl group in Ia-C into such a leaving group as Cl or Br using the standard halogenation method leads to intermediates of formula Ia-D. The cross coupling between halide Ia-D and boronic acid A, which can be carried out under typical Suzuki coupling conditions such as the one shown in the Scheme 2, gives tricyclic intermediate Ia-E. Sequential transformation of the methoxy group of intermediate Ia-E into a thio group and subsequent alkylation of the resulting thio group with bromo acid B leads to compounds of formula Ia.

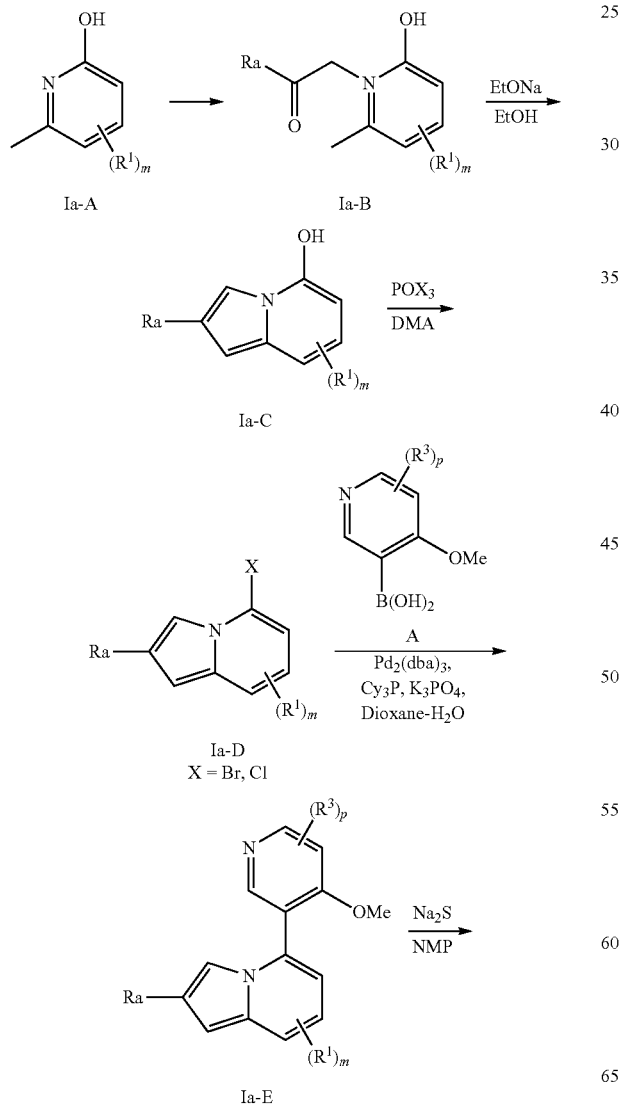

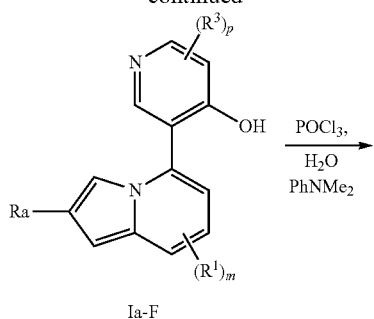

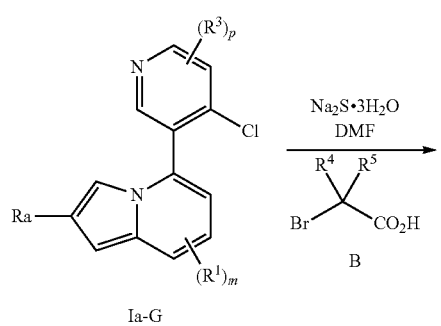

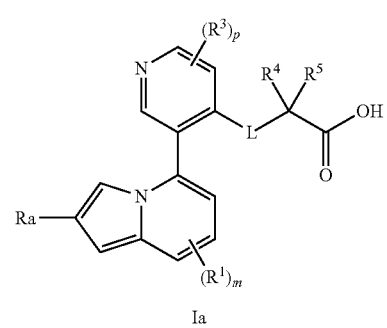

Ra in each compound is independly selected from $R^2$ provided that a stable chemical structure results As a further illustration of the preparation of compounds of formula I, one synthetic route of compounds of Ib is shown in Scheme 3. Alkylation of 2-Acyl pyrrole Ib-A with 2-bromoacetonitrile in a polar solvent such as DMF in the presence of a base such as NaH leads to intermediate Ib-B. Lewis acid catalyzed condensation of ketone Ib-B with orthoester or orthoester synthetic equivalents, which is represented by formula C, provides cyclization precursor of formula Ib-C. Bicyclic heteroaryl compound of formula Ib-D can be prepared from the intramolecular cyclization of Ib-C which can be effected in the presence a base such as LiHMDS in a polar solvent such as THF. Conversion of the hydroxyl group in Ib-D into OTf group results in compounds of formula Ib-E. Coupling of intermediate Ib-E with boronic acid B under typical Suzuki coupling conditions provides compounds of formula Ib-F. Compounds of formula Ib can be obtained through a sequence of transformation of the chloride of intermediate Ib-F into thio group, alkylation of the thio group with bromo ester B and hydrolysis of the ester into an acid group.

Scheme 3

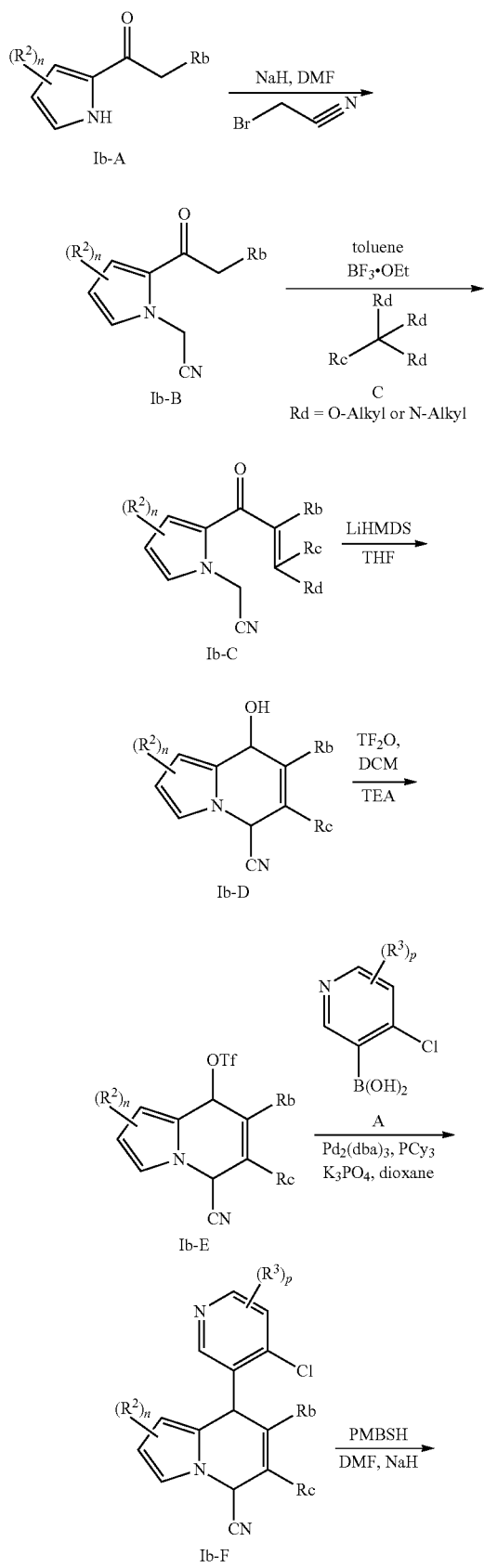

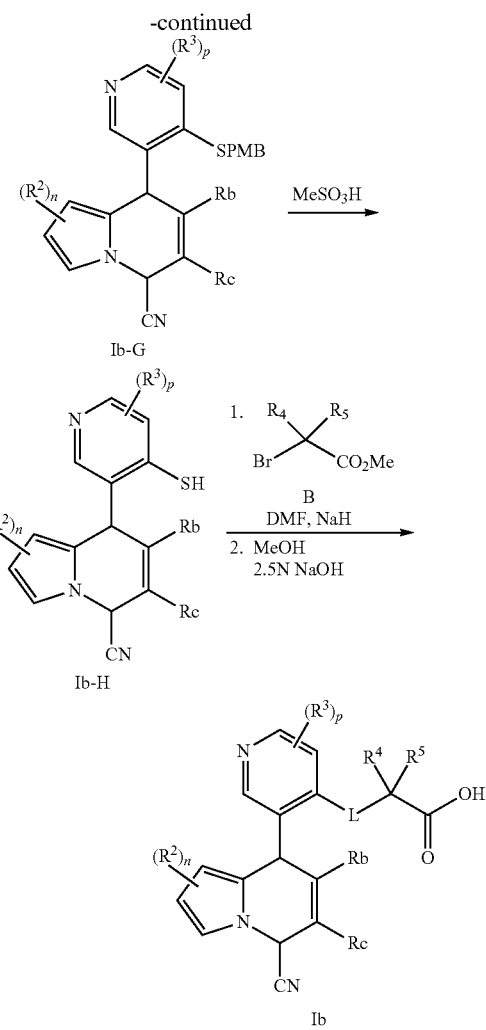

Rb, Rc is indepently selected from R¹ provided that a stable chemical structure results In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Preparation of Intermediates

Intermediate A 2-methyl-6-oxo-1,6-dihydropyridine-3-carbonitrile
(A)

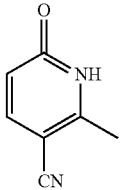

2-methyl-6-oxo-1,6-dihydropyridine-3-carbonitrile (A) was prepared according to the method described in *Synthesis*, 1991, 894. MS-ESI (m/z): 135 [M+1]⁺.

Intermediate B (4-((2,4-Dimethoxybenzyl)oxy)pyridin-3-yl) boronic acid (B)

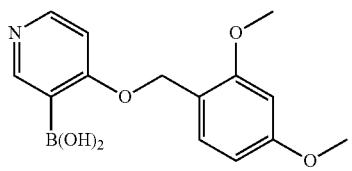

3-bromo-4-((2,4-dimethoxybenzyl)oxy)pyridine (B-1)

To a solution of 3-bromo-4-chloropyridine (5.00 g, 26.00 mmol) in DMF (60 mL) was added (2,4-dimethoxyphenyl) methanol (4.80 g, 28.60 mmol) followed by NaH (1.20 g, 30.0 mmol) in four portions. The mixture was stirred at r.t. for 20 min and then heated at 80° C. for 1 h. The mixture was cooled to r.t., diluted with water and extracted with EtOAc. The extracts were washed with brine and dried over Na₂SO₄. Solvent was evaporated and the residue was purified by chromatography on silica gel, eluting with 20-50% EtOAc in hexanes to give 3-bromo-4-((2,4-dimethoxybenzyl)oxy) pyridine (B-1).

(4-((2,4-dimethoxybenzyl)oxy)pyridin-3-yl) boronic acid (B)

To a solution of 3-bromo-4-((2,4-dimethoxybenzyl)oxy) pyridine (B-1) (1.62 g, 5.00 mmol) in THF (20 mL) at −20° C. was added i-PrMgCl (2.0 M in THF, 3.75 mL, 7.50 mmol). The mixture was stirred at r.t. for 1 h and then was cooled to −20° C. again. (i-PrO)₃B (3.57 g, 19.0 mmol) was added. The mixture was stirred at r.t. for 3 h. The mixture was diluted with saturated aqueous NH₄Cl (15 mL) and extracted with THF. The extracts were washed with brine and dried over Na₂SO₄. Solvent was evaporated. The residue solid was treated with 1:2 MeOH-EtOAc (40 mL), the solid was removed by filtration. The filtrates was evaporated to give (4-((2,4-dimethoxybenzyl)oxy)pyridin-3-yl)boronic acid (B). MS-ESI (m/z): 140 [M+1-DMB]⁺.

Intermediate C 1-bromocyclobutane-1-carboxylic acid (C)

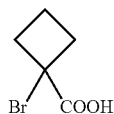

1-bromocyclobutanecarboxylic acid (C) was prepared according to the method described in WO2012/73138.

Intermediate D methyl 1-bromocyclobutane-1-carboxylate (D)

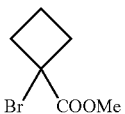

To a solution of 1-bromocyclobutanecarboxylic acid (C) (17.40 g, 97.75 mmol) in MeOH (120 mL) was added concentrated H₂SO₄ (2 mL) dropwise at r.t. After addition, the mixture was warmed to 65° C. for 2 h. The reaction was cooled to r.t. and added H₂O (250 ml), extracted with PE/EtOAc (1:1) (2×150 mL), combine the organic layer, washed with H₂O (200 ml), brine (250 mL), dried over Na₂SO₄ and concentrated to give the crude product of methyl 1-bromocyclobutane-1-carboxylate (D), which was used for next step directly.

Example 1

1-((3-(8-Cyanoindolizin-5-yl)pyridin-4-yl)thio)cyclobutane-1-carboxylic acid (1)

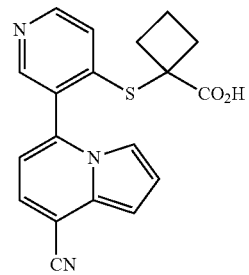

1-allyl-2-methyl-6-oxo-1,6-dihydropyridine-3-carbonitrile (1b)

To a solution of 2-methyl-6-oxo-1,6-dihydropyridine-3-carbonitrile (A) (4.02 g, 30.0 mmol) in DMF (90 mL) at r.t. was added NaH (60%, 1.44 g, 36.0 mmol). The mixture was stirred at r.t. for 20 min, and allyl bromide (3.99 g, 33.0 mmol) was added dropwise. The mixture was stirred at r.t. for 16 h. The reaction was diluted with water (300 mL), extracted with EtOAc. The extracts were washed with brine and dried over Na₂SO₄. The solvent was evaporated, the residue was purified by column chromatography on silica gel, eluting with 20-50% EtOAc in hexanes to give 1-allyl-2-methyl-6-oxo-1,6-dihydropyridine-3-carbonitrile (1b). MS-ESI (m/z): 175 [M+1]⁺.

2-methyl-6-oxo-1-(2-oxoethyl)-1,6-dihydropyridine-3-carbonitrile (1c)

To a solution of 1-allyl-2-methyl-6-oxo-1,6-dihydropyridine-3-carbonitrile (1b) (1.74 g, 10.0 mmol) in 3:1 dioxane-water (100 mL) at r.t. was added 2,6-lutidine (2.14 g, 20.0 mmol), OsO₄ (4% in water, 1.23 mL, 0.20 mmol) and NaIO₄

(8.56 g, 40.0 mmol). The mixture was stirred at r.t. for 23 h. The solid was removed by filtration through silica gel and Na₂SO₄, and washed with EtOAc. The solvents were evaporated, and the residue was purified by column chromatography on silica gel, eluting with 30-90% EtOAc in hexanes to give 2-methyl-6-oxo-1-(2-oxoethyl)-1,6-dihydropyridine-3-carbonitrile (1c). MS-ESI (m/z): 177 [M+1]⁺.

5-hydroxyindolizine-8-carbonitrile (1d)

To a solution of 2-methyl-6-oxo-1-(2-oxoethyl)-1,6-dihydropyridine-3-carbonitrile (1c) (620 mg, 3.52 mmol) in absolute ethanol (10 mL) at r.t. was added a solution of EtONa in ethanol (1.0 M, 5.0 mL). The mixture was stirred at r.t. for 1 h. The solution was acidified with 3 N HCl to pH=5~6. Solvents were evaporated and the residue was purified by column chromatography on silica gel, eluting with 30-50% EtOAc in DCM to give 5-hydroxyindolizine-8-carbonitrile (1d). MS-ESI (m/z): 159 [M+1]⁺.

5-chloroindolizine-8-carbonitrile (1e)

To a solution of 5-hydroxyindolizine-8-carbonitrile (1d) (230 mg, 1.46 mmol) in POCl₃ (5 mL) at r.t. was added N,N-dimethylaniline (352 mg, 2.91 mmol) and water (79 mg, 4.4 mmol). The mixture was heated at 100° C. for 2 h. The mixture was cooled to r.t. and slowly added to ice water (30 mL). The mixture was extracted with EtOAc. The extracts were washed with brine and dried over Na₂SO₄. Solvent was evaporated and the residue was purified by column chromatography on silica gel, eluting with 5-8% EtOAc in hexanes to give 5-chloroindolizine-8-carbonitrile (1e). MS-ESI (m/z): 177/179-3:1 [M+1]⁺.

5-(4-((3,4-dimethoxybenzyl)oxy)pyridin-3-yl)indolizine-8-carbonitrile (1f)

To a solution of 5-chloroindolizine-8-carbonitrile (1e) (215 mg, 1.23 mmol) in dioxane-H₂O (20:1, 5 mL) at r.t. was added (4-((2,4-dimethoxybenzyl)oxy)pyridin-3-yl)boronic acid (intermediate B) (711 mg, 2.46 mmol), Pd(PPh₃)₄ (142 mg, 0.123 mmol), and K₂CO₃ (424 mg, 3.07 mmol). The mixture was heated at 100° C. under N₂ for 22 h. The mixture was cooled to r.t. and diluted with water (30 mL). The mixture was extracted with EtOAc. The extracts were washed with brine and dried over Na₂SO₄. Solvent was evaporated and the residue was purified by column chromatography on silica gel, eluting with 20-70% EtOAc in hexanes to give 5-(4-((3,4-dimethoxybenzyl)oxy)pyridin-3-yl)indolizine-8-carbonitrile (1f). MS-ESI (m/z): 386 [M+1]⁺.

5-(4-hydroxypyridin-3-yl)indolizine-8-carbonitrile (1g)

To a solution of 5-(4-((3,4-dimethoxybenzyl)oxy)pyridin-3-yl)indolizine-8-carbonitrile (1f) (150 mg, 0.39 mmol) in DCM (5 mL) at r.t. was added TFA (2 mL). The mixture was stirred at r.t. for 2 h. Solvents were evaporated and the residue was purified by column chromatography on silica gel, eluting with 5-8% MeOH in DCM to give 5-(4-hydroxypyridin-3-yl)indolizine-8-carbonitrile (1g). MS-ESI (m/z): 236 [M+1]⁺.

5-(4-chloropyridin-3-yl)indolizine-8-carbonitrile (1h)

To a solution of 5-(4-hydroxypyridin-3-yl)indolizine-8-carbonitrile (1g) (80 mg, 0.34 mmol) in POCl₃ (2 mL) at r.t. was added N,N-dimethylaniline (82 mg, 0.68 mmol) and water (18 mg, 1.0 mmol). The mixture was heated at 100° C. for 2 h. The mixture was cooled to r.t. and slowly added to ice water (30 mL). The mixture was extracted with EtOAc. The extracts were washed with brine and dried over Na₂SO₄. Solvent was evaporated and the residue was purified by column chromatography on silica gel, eluting with 20-50% EtOAc in hexanes to give 5-(4-chloropyridin-3-yl)indolizine-8-carbonitrile (1h). MS-ESI (m/z): 254/256-3:1 [M+1]⁺.

1-((3-(8-cyanoindolizin-5-yl)pyridin-4-yl)thio)cyclobutane-1-carboxylic acid (1)

To a solution of 5-(4-chloropyridin-3-yl)indolizine-8-carbonitrile (1h) (11.0 mg, 0.043 mmol) in DMF (0.2 mL) was added Na₂S.2.9H₂O (11.3 mg, 0.086 mmol). The mixture was heated at 90° C. for 30 min. After cooling to r.t., intermediate C (33 mg, 0.21 mmol) was added to above reaction. The mixture was heated at 60° C. for 30 min. The mixture was cooled to r.t. and diluted with water (3 mL), acidified with 1 N HCl to pH=3~4. The mixture was extracted with EtOAc. The extracts were washed with brine and dried over Na₂SO₄. Solvent was evaporated and the residue was purified by column chromatography on silica gel, eluting with 5% MeOH in DCM to give 1-((3-(8-cyanoindolizin-5-yl)pyridin-4-yl)thio)cyclobutane-1-carboxylic acid (1). MS-ESI (m/z): 350 [M+1]⁺.

Example 2

2-((3-(8-cyanoindolizin-5-yl)pyridin-4-yl)thio)-2-methylpropanoic acid (2)

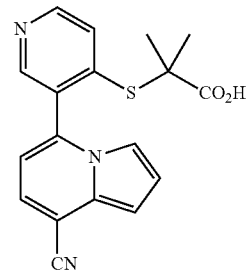

2 ethyl 2-((3-(8-cyanoindolizin-5-yl)pyridin-4-yl)thio)-2-methylpropanoate (2a)

To a solution of 5-(4-chloropyridin-3-yl)indolizine-8-carbonitrile (1h) (12.2 mg, 0.048 mmol) in DMF (0.2 mL) was added Na₂S.2.9H₂O (16.4 mg, 0.126 mmol). The mixture was heated at 100° C. for 25 min. After cooling to r.t., ethyl 2-bromo-2-methylpropanoate (51 mg, 0.26 mmol) was added to above reaction. The mixture was heated at 60° C. for 30 min. The mixture was cooled to r.t. and diluted with water (3 mL) and extracted with EtOAc. The extracts were washed with brine and dried over Na₂SO₄. Solvent was evaporated and the residue was purified by column chromatography on silica gel, eluting with 35% EtOAc in hexanes to give ethyl 2-((3-(8-cyanoindolizin-5-yl)pyridin-4-yl)thio)-2-methylpropanoate (2a). MS-ESI (m/z): 366 [M+1]⁺.

2-((3-(8-cyanoindolizin-5-yl)pyridin-4-yl)thio)-2-methylpropanoic acid (2)

To a solution of ethyl 2-((3-(8-cyanoindolizin-5-yl)pyridin-4-yl)thio)-2-methylpropanoate (2a) (6.5 mg, 0.018 mmol) in MeOH (0.3 mL) was added 2.5 N NaOH in water (0.3 mL). The mixture was stirred at r.t. for 1 h. 3 N HCl was added to pH=3~4. Solvents were evaporated and the residue was purified by column chromatography on silica gel, eluting with 5% MeOH in DCM to give 2-((3-(8-cyanoindolizin-5-yl)pyridin-4-yl)thio)-2-methylpropanoic acid (2). MS-ESI (m/z): 338 [M+1]$^+$.

Example 3

2-((3-(3-chloro-8-cyanoindolizin-5-yl)pyridin-4-yl)thio)-2-methylpropanoic acid

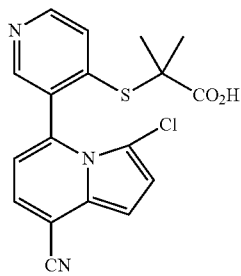

3 ethyl 2-((3-(3-chloro-8-cyanoindolizin-5-yl)pyridin-4-yl)thio)-2-methylpropanoate (3a) and ethyl 2-((3-(1-chloro-8-cyanoindolizin-5-yl)pyridin-4-yl)thio)-2-methylpropanoate (4a)

To a solution of ethyl 2-((3-(8-cyanoindolizin-5-yl)pyridin-4-yl)thio)-2-methylpropanoate (2a) (5.2 mg, 0.014 mmol) in 5:1 CH$_3$CN-MeOH (0.3 mL) was NCS (3.8 mg, 0.028 mmol). The mixture was stirred at r.t. for 4 h. The mixture was diluted with 5% NaHSO$_3$ (5 mL) and extracted with EtOAc. Solvents were evaporated and the residue was purified by column chromatography on silica gel, eluting with 20-40% EtOAc in hexanes to give ethyl 2-((3-(3-chloro-8-cyanoindolizin-5-yl)pyridin-4-yl)thio)-2-methylpropanoate (3a) and ethyl 2-((3-(1-chloro-8-cyanoindolizin-5-yl)pyridin-4-yl)thio)-2-methylpropanoate (4a). 3a, MS-ESI (m/z): 400.4/402.4, 3:1, [M+1]$^+$. 4a, MS-ESI (m/z): 400/402, 3:1, [M+1]$^+$.

2-((3-(3-chloro-8-cyanoindolizin-5-yl)pyridin-4-yl)thio)-2-methylpropanoic acid To a solution of ethyl 2-((3-(3-chloro-8-cyanoindolizin-5-yl)pyridin-4-yl)thio)-2-methylpropanoate (3a) (3.5 mg, 0.0088 mmol) in MeOH (0.2 mL) was added 2.5 N NaOH in water (0.1 mL). The mixture was stirred at r.t. for 1 h. 3 N HCl was added to pH=3~4. Solvents were evaporated and the residue was purified by column chromatography on silica gel, eluting with 5% MeOH in DCM to give 2-((3-(3-chloro-8-cyanoindolizin-5-yl)pyridin-4-yl)thio)-2-methylpropanoic acid (3). MS-ESI (m/z): 372/374, 3:1, [M+1]$^+$.

Example 4

2-((3-(1-chloro-8-cyanoindolizin-5-yl)pyridin-4-yl)thio)-2-methylpropanoic acid (4)

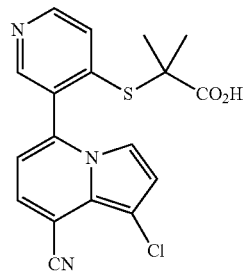

4

To a solution of ethyl 2-((3-(1-chloro-8-cyanoindolizin-5-yl)pyridin-4-yl)thio)-2-methylpropanoate (4a) (1.5 mg, 0.0038 mmol) in MeOH (0.1 mL) was added 2.5 N NaOH in water (0.1 mL). The mixture was stirred at r.t. for 1 h, and the mixture was adjusted to pH=3~4 using 3 N HCl. Solvents were evaporated and the residue was purified by column chromatography on silica gel, eluting with 5% MeOH in DCM to give 2-((3-(1-chloro-8-cyanoindolizin-5-yl)pyridin-4-yl)thio)-2-methylpropanoic acid (4). MS-ESI (m/z): 372/374, 3:1, [M+1]$^+$.

Example 5

1-((3-(8-cyano-2-methylindolizin-5-yl)pyridin-4-yl)thio)cyclobutane-1-carboxylic acid (5)

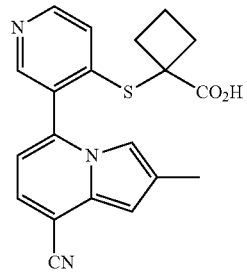

5

2-methyl-6-oxo-1-(2-oxopropyl)-1,6-dihydropyridine-3-carbonitrile (5a)

To a mixture of 2-methyl-6-oxo-1,6-dihydropyridine-3-carbonitrile (A) (1.100 g, 8.21 mmol) and KI (1.36 g, 8.21 mmol) in DMF (25 mL) at r.t. was added NaH (60%, 394 mg, 9.85 mmol). The mixture was stirred at r.t. for 20 min, 1-chloropropan-2-one (1.52 g, 16.4 mmol) was added dropwise. The mixture was stirred at r.t. for 1 h. The reaction was diluted with water (150 mL), extracted with EtOAc. The extracts were dried over Na$_2$SO$_4$. The solvent was evaporated, the residue was purified by column chromatography on silica gel, eluting with 20-50% EtOAc in DCM to give 2-methyl-6-oxo-1-(2-oxopropyl)-1,6-dihydropyridine-3-carbonitrile (5a). MS-ESI (m/z): 191 [M+1]$^+$.

5-hydroxy-2-methylindolizine-8-carbonitrile (5b)

To a solution of 2-methyl-6-oxo-1-(2-oxopropyl)-1,6-dihydropyridine-3-carbonitrile (5a) (325 mg, 1.71 mmol) in absolute ethanol (3.5 mL) at r.t. was added a solution of EtONa in ethanol (1.0 M, 3.5 mL). The mixture was stirred at r.t. for 1 h. The solution was acidified with 3 N HCl to pH=4~5. Solvents were evaporated and the residue was purified by column chromatography on silica gel, eluting with 50-70% EtOAc in hexanes to give product of 5b (192 mg, 65%) as pale yellow solid. MS-ESI (m/z): 173 [M+1]$^+$.

5-chloro-2-methylindolizine-8-carbonitrile (5c)

To a solution of 5-hydroxy-2-methylindolizine-8-carbonitrile (5b) (192 mg, 1.12 mmol) in POCl$_3$ (3.5 mL) at r.t. was added N,N-dimethylaniline (270 mg, 2.23 mmol) and water (18 mg, 1.0 mmol). The mixture was heated at 100° C. for 3 h. The mixture was cooled to rt and slowly added to ice water (30 mL). The mixture was extracted with EtOAc. The extracts were washed with brine and dried over Na$_2$SO$_4$. Solvent was evaporated and the residue was purified by column chromatography on silica gel, eluting with 5-8% EtOAc in hexanes to give 5-chloro-2-methylindolizine-8-carbonitrile (5c). MS-ESI (m/z): 191/193-3:1 [M+1]$^+$.

5-(4-methoxypyridin-3-yl)-2-methylindolizine-8-carbonitrile (5d)

To a solution of 5-chloro-2-methylindolizine-8-carbonitrile (5c) (111 mg, 0.583 mmol) in dioxane (1.5 mL) at r.t. was added (4-methoxypyridin-3-yl)boronic acid (120 mg, 0.699 mmol), Pd$_2$(dba)$_3$ (21.4 mg, 0.0233 mmol), PCy$_3$ (13.0 mg, 0.0466 mmol) and K$_3$PO$_4$ (1.27 M, 0.78 mL, 0.99 mmol). The mixture was heated at 100° C. under N$_2$ for 6 h. The mixture was cooled to r.t. and diluted with water (10 mL). The mixture was extracted with EtOAc. The extracts were washed with brine and dried over Na$_2$SO$_4$. Solvent was evaporated and the residue was purified by column chromatography on silica gel, eluting with 2-5% MeOH in DCM to give 5-(4-methoxypyridin-3-yl)-2-methylindolizine-8-carbonitrile (5d). MS-ESI (m/z): 264 [M+1]$^+$.

5-(4-hydroxypyridin-3-yl)-2-methylindolizine-8-carbonitrile (5e)

To a solution of 5-(4-methoxypyridin-3-yl)-2-methylindolizine-8-carbonitrile (5d) (130 mg, 0.494 mmol) in NMP (1.5 mL) was added Na$_2$S (193 mg, 2.47 mmol). The mixture was stirred at 145° C. for 4 h. The mixture was cooled to r.t., diluted with water, acidified with 3 N HCl to pH=4~5, and extracted with EtOAc and DCM. Solvents were evaporated and the residue was purified by column chromatography on silica gel, eluting with 2-10% MeOH in DCM to give 5-(4-hydroxypyridin-3-yl)-2-methylindolizine-8-carbonitrile (5e). MS-ESI (m/z): 250 [M+1]$^+$.

5-(4-chloropyridin-3-yl)-2-methylindolizine-8-carbonitrile (5f)

To a solution of 5-(4-hydroxypyridin-3-yl)-2-methylindolizine-8-carbonitrile (5e) (92 mg, 0.37 mmol) in POCl$_3$ (2 mL) at r.t. was added N,N-dimethylaniline (89 mg, 0.74 mmol) and water (30 mg, 1.7 mmol). The mixture was heated at 100° C. for 1.5 h. The mixture was cooled to r.t. and slowly added to ice cold aqueous NaHCO$_3$ (30 mL). The mixture was extracted with EtOAc. The extracts were washed with brine and dried over Na$_2$SO$_4$. Solvent was evaporated and the residue was purified by column chromatography on silica gel, eluting with 40% EtOAc in hexanes to give 5-(4-chloropyridin-3-yl)-2-methylindolizine-8-carbonitrile (5f). MS-ESI (m/z): 268/270-3:1 [M+1]$^+$.

1-((3-(8-cyano-2-methylindolizin-5-yl)pyridin-4-yl)thio)cyclobutane-1-carboxylic acid (5)

To a solution of 5-(4-chloropyridin-3-yl)-2-methylindolizine-8-carbonitrile (5f) (16.3 mg, 0.061 mmol) in DMF (0.2 mL) was added Na$_2$S.2.9H$_2$O (15.8 mg, 0.122 mmol). The mixture was heated at 95° C. for 30 min. After cooling to r.t., 1-bromocyclobutanecarboxylic acid (intermediate C) (40 mg, 0.22 mmol) was added to above reaction. The mixture was heated at 70° C. for 2 h. The mixture was cooled to r.t. and diluted with water (3 mL), acidified with 1 N HCl to pH=3~4. The mixture was extracted with EtOAc. The extracts were washed with brine and dried over Na$_2$SO$_4$. Solvent was evaporated and the residue was purified by column chromatography on silica gel, eluting with 5% MeOH in DCM to give 1-((3-(8-cyano-2-methylindolizin-5-yl)pyridin-4-yl)thio)cyclobutane-1-carboxylic acid (5). MS-ESI (m/z): 364 [M+1]$^+$.

Example 6

2-((3-(8-Cyano-2-methylindolizin-5-yl)pyridin-4-yl)thio)-2-methylpropanoic acid (6)

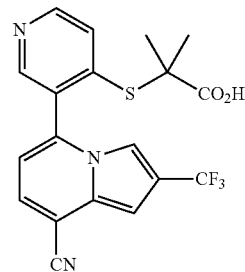

6 ethyl 2-((3-(8-cyano-2-methylindolizin-5-yl)pyridin-4-yl)thio)-2-methylpropanoate (6a)

To a solution of 5-(4-chloropyridin-3-yl)-2-methylindolizine-8-carbonitrile (5f) (14.6 mg, 0.055 mmol) in DMF (0.2 mL) was added Na$_2$S.2.9H$_2$O (17.7 mg, 0.136 mmol). The mixture was heated at 100° C. for 30 min. After cooling to r.t., ethyl 2-bromo-2-methylpropanoate (53 mg, 0.27 mmol) was added to above reaction. The mixture was heated at 60° C. for 30 min. The mixture was cooled to r.t. and diluted with water (3 mL) and extracted with EtOAc. The extracts were washed with brine and dried over Na$_2$SO$_4$. Solvent was evaporated and the residue was purified by column chromatography on silica gel, eluting with 30% EtOAc in hexanes to give ethyl 2-((3-(8-cyano-2-methylindolizin-5-yl)pyridin-4-yl)thio)-2-methylpropanoate (6a). MS-ESI (m/z): 380 [M+1]$^+$.

2-((3-(8-cyano-2-methylindolizin-5-yl)pyridin-4-yl)thio)-2-methylpropanoic acid To a solution of ethyl 2-((3-(8-cyano-2-methylindolizin-5-yl)pyridin-4-yl)thio)-2-methylpropanoate (6a) (16.5 mg, 0.044 mmol) in MeOH (0.6 mL) was added 2.5 N NaOH in water (0.3 mL). The mixture was stirred at r.t. for 1 h. 3 N HCl was added to pH=3~4. Solvents were evaporated and the residue was purified by column chromatography on silica gel, eluting with 5% MeOH in DCM to give 2-((3-(8-cyano-2-methylindolizin-5-yl)pyridin-4-yl)thio)-2-methylpropanoic acid (6). MS-ESI (m/z): 352 [M+1]⁺.

Example 7

1-((3-(8-cyano-2-(trifluoromethyl)indolizin-5-yl)pyridin-4-yl)thio)cyclobutane-1-carboxylic acid (7)

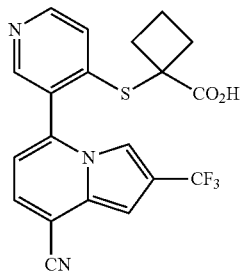

7

2-(5-cyano-6-methyl-2-oxopyridin-1(2H)-yl)acetic acid (7a)

To a solution of 2-methyl-6-oxo-1-(2-oxoethyl)-1,6-dihydropyridine-3-carbonitrile (1c) (910 mg, 5.17 mmol) in DMF (25 mL) was added oxone (3.08 g, 5.00 mmol). The mixture was stirred at r.t. for 1 h. Additional 1.70 g (2.76 mmol) of oxone was added. The mixture was stirred at r.t. for an additional 4 h. The mixture was diluted with water (125 mL), extracted with EtOAc and 20:1 DCM-MeOH. Solvents were evaporated and the residue was purified by column chromatography on silica gel, eluting with 10-30% MeOH in DCM to give 2-(5-cyano-6-methyl-2-oxopyridin-1(2H)-yl)acetic acid (7a). MS-ESI (m/z): 193 [M+1]⁺.

2-methyl-6-oxo-1-(3,3,3-trifluoro-2-oxopropyl)-1,6-dihydropyridine-3-carbonitrile (7b)

To a solution of 2-(5-cyano-6-methyl-2-oxopyridin-1(2H)-yl)acetic acid (7a) (870 mg, 4.53 mmol) in toluene (20 mL) was added pyridine (2.2 mL) and TFAA (2.1 mL). The mixture was stirred at r.t. for 1 h and then heated at 90° C. for 4 h. After being cooled to r.t., the mixture was diluted with brine (150 mL), extracted with EtOAc. The extracts were washed with 0.5 N HCl and brine. Solvents were evaporated and the residue was purified by column chromatography on silica gel, eluting with 30-80% EtOAc in hexanes to give 2-methyl-6-oxo-1-(3,3,3-trifluoro-2-oxopropyl)-1,6-dihydropyridine-3-carbonitrile (7b).

5-hydroxy-2-(trifluoromethyl)indolizine-8-carbonitrile (7c)

To a solution of 2-methyl-6-oxo-1-(3,3,3-trifluoro-2-oxopropyl)-1,6-dihydropyridine-3-carbonitrile (7b) (925 mg, 3.79 mmol) in absolute ethanol (20 mL) at r.t. was added a solution of EtONa in ethanol (1.0 M, 5.7 mL). The mixture was heated at 80° C. for 2 h. After cooling to r.t., the solution was acidified with 3 N HCl to pH=3~4. Solvents were evaporated and the residue was purified by column chromatography on silica gel, eluting with 50% EtOAc in DCM to give 5-hydroxy-2-(trifluoromethyl)indolizine-8-carbonitrile (7c). MS-ESI (m/z): 225 [M−1]⁺.

5-chloro-2-(trifluoromethyl)indolizine-8-carbonitrile (7d)

To a solution of 5-hydroxy-2-(trifluoromethyl)indolizine-8-carbonitrile (7c) (375 mg, 1.66 mmol) in POCl₃ (5 mL) at r.t. was added N,N-dimethylaniline (401 mg, 3.32 mmol) and water (86 mg, 4.78 mmol). The mixture was heated at 100° C. for 4 h. The mixture was cooled to r.t. and slowly added to ice cold aqueous NaHCO₃ (100 mL). The mixture was extracted with EtOAc. The extracts were washed with brine and dried over Na₂SO₄. Solvent was evaporated and the residue was purified by column chromatography on silica gel, eluting with 5% EtOAc in hexanes to give 5-chloro-2-(trifluoromethyl)indolizine-8-carbonitrile (7d), which did not show MS signal.

5-(4-methoxypyridin-3-yl)-2-(trifluoromethyl)indolizine-8-carbonitrile (7e)

To a solution of 5-chloro-2-(trifluoromethyl)indolizine-8-carbonitrile (7d) (154 mg, 0.630 mmol) in dioxane (2.5 mL) at r.t. was added (4-methoxypyridin-3-yl)boronic acid (129 mg, 0.756 mmol), Pd₂(dba)₃ (23.0 mg, 0.025 mmol), PCy₃ (14.0 mg, 0.0504 mmol) and K₃PO₄ (1.27 M, 0.84 mL, 1.07 mmol). The mixture was heated at 100° C. under N₂ for 3 h. The mixture was cooled to r.t. and diluted with water (10 mL). The mixture was extracted with EtOAc. The extracts were washed with brine and dried over Na₂SO₄. Solvents were evaporated and the residue was purified by column chromatography on silica gel, eluting with 50-70% EtOAc in hexanes to give 5-(4-methoxypyridin-3-yl)-2-(trifluoromethyl)indolizine-8-carbonitrile (7e). MS-ESI (m/z): 318 [M+1]⁺.

5-(4-hydroxypyridin-3-yl)-2-(trifluoromethyl)indolizine-8-carbonitrile (7f)

To a solution of 5-(4-methoxypyridin-3-yl)-2-(trifluoromethyl)indolizine-8-carbonitrile (7e) (148 mg, 0.467 mmol) in NMP (2.5 mL) was added Na₂S (146 mg, 1.87 mmol). The mixture was heated at 145° C. for 4 h. After cooling to r.t., the mixture was diluted with water and acidified with 3 N HCl to pH=5~6, extracted with 10:1 DCM-MeOH. Solvents were evaporated and the residue was purified by column chromatography on silica gel, eluting with 5-10% MeOH in DCM to give 5-(4-hydroxypyridin-3-yl)-2-(trifluoromethyl)indolizine-8-carbonitrile (7f). MS-ESI (m/z): 304 [M+1]⁺.

5-(4-chloropyridin-3-yl)-2-(trifluoromethyl)indolizine-8-carbonitrile (7g)

To a solution of 5-(4-hydroxypyridin-3-yl)-2-(trifluoromethyl)indolizine-8-carbonitrile (7f) (130 mg, 0.429 mmol) in POCl₃ (1.5 mL) at r.t. was added N,N-dimethylaniline (104 mg, 0.86 mmol) and water (23.5 mg, 1.31 mmol). The mixture was heated at 100° C. for 2 h. The mixture was cooled to r.t. and slowly added to ice cold aqueous NaHCO₃ (10 mL). The mixture was extracted with EtOAc. The extracts were washed with brine and dried over Na₂SO₄. Solvent was evaporated and the residue was purified by column chromatography on silica gel, eluting with 30-50%

EtOAc in hexanes to give 5-(4-chloropyridin-3-yl)-2-(trifluoromethyl)-indolizine-8-carbonitrile (7g). MS-ESI (m/z): 322/324-3:1, [M+1]⁺.

methyl 1-((3-(8-cyano-2-(trifluoromethyl)indolizin-5-yl)pyridin-4-yl)thio)-cyclobutane-1-carboxylate (7h)

To a solution of 5-(4-chloropyridin-3-yl)-2-(trifluoromethyl)indolizine-8-carbonitrile (7g) (77.8 mg, 0.244 mmol) in DMF (1 mL) was added Na$_2$S (38.1 mg, 0.488 mmol). The mixture was heated at 90° C. for 30 min. After cooling to r.t., methyl 1-bromocyclobutane-1-carboxylate (intermediate D) (141 mg, 0.732 mmol) was added to above reaction. The mixture was heated at 60° C. for 2 h. The mixture was cooled to r.t., diluted with water (3 mL) and extracted with EtOAc. The extracts were washed with brine and dried over Na$_2$SO$_4$. Solvent was evaporated and the residue was purified by column chromatography on silica gel, eluting with 30-50% EtOAc in hexanes to give methyl 1-((3-(8-cyano-2-(trifluoromethyl)indolizin-5-yl)pyridin-4-yl)thio)cyclobutane-1-carboxylate (7h). MS-ESI (m/z): 432 [M+1]⁺.

1-((3-(8-cyano-2-(trifluoromethyl)indolizin-5-yl)pyridin-4-yl)thio)-cyclobutane-1-carboxylic acid (7)

To a solution of methyl 1-((3-(8-cyano-2-(trifluoromethyl)indolizin-5-yl)pyridin-4-yl)thio)cyclobutane-1-carboxylate (7h) (32.6 mg, 0.0756 mmol) in MeOH (1 mL) was added 2.5 N NaOH in water (1 mL). The mixture was stirred at r.t. for 1 h. 3 N HCl was added to pH=3~4. Solvents were evaporated and the residue was purified by column chromatography on silica gel, eluting with 5% MeOH in DCM to give 1-((3-(8-cyano-2-(trifluoromethyl)indolizin-5-yl)pyridin-4-yl)thio)-cyclobutane-1-carboxylic acid (7). MS-ESI (m/z): 418 [M+1]⁺.

Example 8

1-((3-(5-cyanoindolizin-8-yl)pyridin-4-yl)thio)cyclobutane-1-carboxylic acid (8)

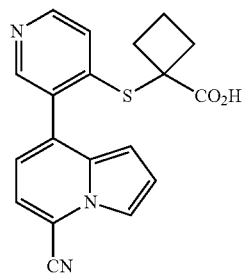

8

2-(2-acetyl-1H-pyrrol-1-yl)acetonitrile (8a)

To a solution of 1-(1H-pyrrol-2-yl)ethan-1-one (5.45 g, 50.0 mmol) in DMF (50 mL) at 0° C. was added NaH (60%, 2.20 g, 55.0 mmol). The mixture was stirred at 0° C. for 10 min, and then 2-bromoacetonitrile (12.00 g, 100.0 mmol) was added. The mixture was stirred at r.t for 15 h. The mixture was diluted with water (400 mL), extracted with EtOAc. Solvents were evaporated and the residue was crystallized from EtOAc-hexanes to give pure 2-(2-acetyl-1H-pyrrol-1-yl)acetonitrile (8a). The mother liquid was purified by column chromatography on silica gel, eluting with 10-30% EtOAc in hexanes to give more 2-(2-acetyl-1H-pyrrol-1-yl)acetonitrile (8a). MS-ESI (m/z): 149 [M+1]⁺.

(E)-2-(2-(3-(dimethylamino)acryloyl)-1H-pyrrol-1-yl)acetonitrile (8b)

To a solution of 2-(2-acetyl-1H-pyrrol-1-yl)acetonitrile (8a) (3.77 g, 25.5 mmol) in toluene (25 mL) was added DMF-DMA (4.55g, 38.2 mmol) followed by BF$_3$.OEt$_2$ (0.3 mL). The mixture was heated at 110° C. for 25 h. Solvents were evaporated and the residue was purified by column chromatography on silica gel, eluting with 30-60% EtOAc in hexanes to give (E)-2-(2-(3-(dimethylamino)acryloyl)-1H-pyrrol-1-yl)acetonitrile (8b). MS-ESI (m/z): 204 [M+1]⁺.

8-hydroxyindolizine-5-carbonitrile (8c)

To a solution of (E)-2-(2-(3-(dimethylamino)acryloyl)-1H-pyrrol-1-yl)-acetonitrile (8b) (2.73 g, 13.5 mmol) in THF (90 mL) at 0° C. was added a solution of LiHMDS in THF (1.0 M, 24.2 mL). The mixture was stirred at r.t. for 2 h. The mixture was diluted with water, acidified with 3 N HCl to pH=4~5, and extracted with EtOAc. Solvents were evaporated and the residue was purified by column chromatography on silica gel, eluting with 20-30% EtOAc in hexanes to give 8-hydroxyindolizine-5-carbonitrile (8c). MS-ESI (m/z): 157 [M−1]⁺.

5-cyanoindolizin-8-yl trifluoromethanesulfonate (8d)

To a solution of 8-hydroxyindolizine-5-carbonitrile (8c) (307 mg, 1.94 mmol) in DCM (10 mL) at 0° C. was added Tf$_2$O (658 mg, 2.33 mmol) followed by TEA (235 mg, 2.33 mmol). The mixture was stirred at rt for 1 h. The mixture was diluted with water and extracted with DCM. Solvent was evaporated and the residue was purified by column chromatography on silica gel, eluting with 3-5% EtOAc in hexanes to give 5-cyanoindolizin-8-yl trifluoromethanesulfonate (8d). MS-ESI (m/z): 291 [M+1]⁺.

8-(4-chloropyridin-3-yl)indolizine-5-carbonitrile (8e)

To a solution of 5-cyanoindolizin-8-yl trifluoromethanesulfonate (8d) (309 mg, 1.07 mmol) in dioxane (5 mL) at r.t. was added 4-chloro-3-(4,4,5,5-tetramethyl-1,3,2-dioxaborolan-2-yl)pyridine (323 mg, 1.17 mmol), Pd$_2$(dba)$_3$ (48.8 mg, 0.053 mmol), PCy$_3$ (29.8 mg, 0.107 mmol) and K$_3$PO$_4$ (1.27 M, 1.26 mL, 1.60 mmol). The mixture was heated at 100° C. under N$_2$ for 4 h. The mixture was cooled to r.t. and diluted with water (20 mL). The mixture was extracted with EtOAc. The extracts were washed with brine and dried over Na$_2$SO$_4$. Solvents were evaporated and the residue was purified by column chromatography on silica gel, eluting with 5-20% EtOAc in hexanes to give 8-(4-chloropyridin-3-yl)indolizine-5-carbonitrile (8e). MS-ESI (m/z): 254/256-3:1, [M+1]⁺.

8-(4-((4-methoxybenzyl)thio)pyridin-3-yl)indolizine-5-carbonitrile (8f)

To a solution of 8-(4-chloropyridin-3-yl)indolizine-5-carbonitrile (8e) (66.3 mg, 0.262 mmol) in DMF (1.5 mL) at 0°

C. was added (4-methoxyphenyl)methanethiol (60.4 mg, 0.392 mmol) followed by NaH (60%, 18.9 mg, 0.472 mmol). The mixture was stirred at r.t. for 1 h. The mixture was diluted with water (10 mL), extracted with EtOAc. Solvents were evaporated and the residue was purified by column chromatography on silica gel, eluting with 30-50% EtOAc in hexanes to give 8-(4-((4-methoxybenzyl)thio)pyridin-3-yl)indolizine-5-carbonitrile (8f). MS-ESI (m/z): 372, [M+1]+.

8-(4-mercaptopyridin-3-yl)indolizine-5-carbonitrile (8g)

A mixture of 8-(4-((4-methoxybenzyl)thio)pyridin-3-yl)indolizine-5-carbonitrile (8f) (31.3 mg, 0.084 mmol) and MeSO$_3$H (1 mL) was heated at 80° C. for 1.5 h. After cooled to r.t., the solution was diluted with NaHCO$_3$ to pH=6. The mixture was extracted with EtOAc. Solvents were evaporated and the residue was purified by column chromatography on silica gel, eluting with 5% MeOH in DCM to give 8-(4-mercaptopyridin-3-yl)indolizine-5-carbonitrile (8g). MS-ESI (m/z): 252 [M+1]+.

methyl 1-((3-(5-cyanoindolizin-8-yl)pyridin-4-yl)thio)cyclobutane-1-carboxylate (8h)

To a solution of 8-(4-mercaptopyridin-3-yl)indolizine-5-carbonitrile (8g) (24.1 mg, 0.096 mmol) in DMF (1 mL) at 0° C. was added methyl 1-bromocyclobutane-1-carboxylate (49.2 mg, 0.255 mmol) followed by NaH (60%, 6.0 mg, 0.15 mmol). The mixture was heated at 60° C. for 1 h. The mixture was diluted with water (5 mL), extracted with EtOAc. Solvents were evaporated and the residue was purified by column chromatography on silica gel, eluting with 30-50% EtOAc in hexanes to give methyl 1-((3-(5-cyanoindolizin-8-yl)pyridin-4-yl)thio)cyclobutane-1-carboxylate (8h). MS-ESI (m/z): 364, [M+1]+.

1-((3-(5-cyanoindolizin-8-yl)pyridin-4-yl)thio)cyclobutane-1-carboxylic acid (8)

To a solution of methyl 1-((3-(5-cyanoindolizin-8-yl)pyridin-4-yl)thio)cyclobutane-1-carboxylate (8h) (21.7 mg, 0.0598 mmol) in MeOH (1 mL) was added 2.5 N NaOH in water (1 mL). The mixture was stirred at r.t. for 1 h. The mixture was adjusted to pH=3~4 using 3 N HCl. Solvents were evaporated and the residue was purified by column chromatography on silica gel, eluting with 5-10% MeOH in DCM to give 1-((3-(5-cyanoindolizin-8-yl)pyridin-4-yl)thio)cyclobutane-1-carboxylic acid (8). MS-ESI (m/z): 350 [M+1]+.

Following essentially the same procedures described for Examples 8, Examples 9-12 listed in Table 1 were prepared from the appropriate starting materials which are either commercially available or known in the literature.

TABLE 1

| EXAMPLE | STRUCTURE | NAME | DATA |
| --- | --- | --- | --- |
| 9 | 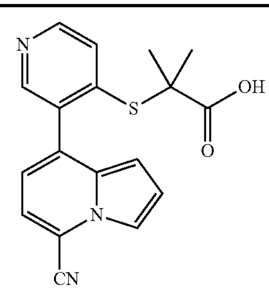 | 2-((3-(5-cyanoindolizin-8-yl)pyridin-4-yl)thio)-2-methylpropanoic acid | MS-ESI (m/z): 338 [M + 1]+ |
| 10 | 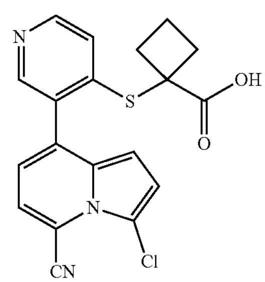 [SMILES: N#Cc1ccc(-c2cnccc2SC2(C(=O)O)CCC2)c2ccc(Cl)n12] | 1-((3-(3-chloro-5-cyanoindolizin-8-yl)pyridin-4-yl)thio)cyclobutane-1-carboxylic acid | MS-ESI (m/z): 384 [M + 1]+ |
| 11 | 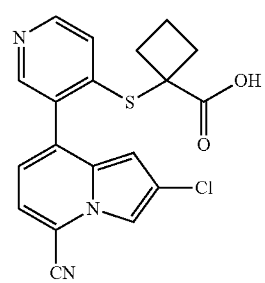 [SMILES: N#Cc1ccc(-c2cnccc2SC2(C(=O)O)CCC2)c2cc(Cl)cn12] | 1-((3-(2-chloro-5-cyanoindolizin-8-yl)pyridin-4-yl)thio)cyclobutane-1-carboxylic acid | MS-ESI (m/z): 384 [M + 1]+ |

TABLE 1-continued

| EXAMPLE | STRUCTURE | NAME | DATA |
|---|---|---|---|
| 12 | 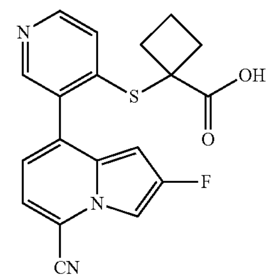 [SMILES: N#Cc1ccc(-c2cnccc2SC2(C(=O)O)CCC2)c2cc(F)cn12] | 1-((3-(5-cyano-2-fluoroindolizin-8-yl)pyridin-4-yl)thio)cyclobutane-1-carboxylic acid | MS-ESI (m/z): 368 [M + 1]+ |

Example 13

1-((3-(2-Chloro-8-cyanoindolizin-5-yl)pyridin-4-yl)thio)cyclobutane-1-carboxylic acid (13)

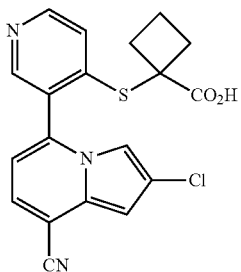

Ethyl 2-(5-bromo-6-methyl-2-oxopyridin-1(2H)-yl)acetate (13a)

To a suspension of 5-bromo-6-methylpyridin-2(1H)-one (18.80 g, 100 mmol) in dry THF (200 mL) at 0° C. was added NaH (60%, 4.80 g, 120 mmol). After being stirred at this temperature for 10 min., ethyl 2-bromoacetate (20.04 g, 120 mmol) was added dropwise. Then the mixture was heated at 50° C. for 6 h. The mixture was cooled to r.t., diluted with water (400 mL) and extracted with EtOAc (2×200 mL). The extracts were washed with brine (400 mL), dried over Na₂SO₄ and concentrated to give the crude product. This was crystallized from EtOAc-hexanes to give ethyl 2-(5-bromo-6-methyl-2-oxopyridin-1(2H)-yl)acetate (13a) as white needles (19.54 g). The mother liquid was purified by silica gel chromatography, eluted with 5-30% EtOAc in hexanes to give further product of ethyl 2-(5-bromo-6-methyl-2-oxopyridin-1(2H)-yl)acetate (13a). MS-ESI (m/z): 274/276 [1:1, M+1]+.

Ethyl 2-(5-cyano-6-methyl-2-oxopyridin-1(2H)-yl)acetate (13b)

To a suspension of ethyl 2-(5-bromo-6-methyl-2-oxopyridin-1(2H)-yl)acetate (13a, 15.44 g, 56.4 mmol) in dry N-methylpyrrolidinone (280 mL) was added CuCN (15.15 g, 169 mmol). After being filled nitrogen, the mixture was heated at reflux for 3 h. Most of the NMP was removed by evaporation under high vacuum. The residue was cooled to r.t., diluted with EtOAc (400 mL) and water (200 mL). The solid was removed by filtration through a layer of celite and washed with EtOAc. The layers were separated. The aq. was extracted with EtOAc (100 mL). The combined organic solution was washed with brine (200 mL), dried over Na₂SO₄ and concentrated to give the crude product. This was crystallized from EtOAc-hexanes to give ethyl 2-(5-cyano-6-methyl-2-oxopyridin-1(2H)-yl)acetate (13b). MS-ESI (m/z): 221 [M+1]+.

2,5-Dichloroindolizine-8-carbonitrile (13c)

To a solution of 2-(5-cyano-6-methyl-2-oxopyridin-1(2H)-yl)acetate (13b, 1.656 g, 7.53 mmol) in absolute ethanol (25 mL) at r.t. was added a solution of EtONa in ethanol (1.0 M, 11.3 mL). The mixture was stirred at heated at reflux for 1 h. The solution was cooled to r.t., acidified with 3 N HCl to pH=5~6. Solvents were evaporated to give solid. To this solid was added N,N-Dimethylaniline (911 mg, 7.53 mmol), H₂O (200 mg, 11.3 mmol) and POCl₃ (20 mL). The mixture was heated at 100° C. for 2 h. The mixture was cooled to r.t. and slowly added to ice water (30 mL). The mixture was extracted with EtOAc (2×). The extracts were washed with brine and dried over Na₂SO₄. Solvent was evaporated and the residue was purified by column on silica gel, eluting with 5-8% EtOAc in hexanes to give 2,5-dichloroindolizine-8-carbonitrile (13c). MS-ESI (m/z): 211/213 [3:2, M+1]+.

2-Chloro-5-(4-chloropyridin-3-yl)indolizine-8-carbonitrile (13d)

To a mixture of 2,5-dichloroindolizine-8-carbonitrile (13c, 500 mg, 2.37 mmol), 4-chloro-3-(4,4,5,5-tetramethyl-1,3,2-dioxaborolan-2-yl)pyridine hydrochloride (700 mg, 2.54 mmol), Pd₂(dba)₃ (152 mg, 0.166 mmol), and tricyclohexylphosphine (93 mg, 0.33 mmol) was added K₃PO₄ (1.27 M) in water (3.73 mL) and dioxane (15 mL). The mixture was heated at 95° C. under N₂ for 13 h. The mixture was cooled to r.t. and diluted with water (50 mL). The mixture was extracted with EtOAc (2×). The extracts were washed with brine and dried over Na₂SO₄. Solvent was evaporated and the residue was purified by column on silica gel, eluting with 5-30% EtOAc in hexanes to give 2-chloro-5-(4-chloropyridin-3-yl)indolizine-8-carbonitrile (13d). MS-ESI (m/z): 288/290 [3:2, M+1]+.

Methyl 1-((3-(2-chloro-8-cyanoindolizin-5-yl)pyridin-4-yl)thio)cyclobutane-1-carboxylate (13e)

To a solution of 2-chloro-5-(4-chloropyridin-3-yl)indolizine-8-carbonitrile (13d) (174 mg, 0.604 mmol) in DMF (2.8 mL) was added Na₂S (61.3 mg, 0.785 mmol). The mixture was heated at 90° C. for 1 h. After cooling to r.t., methyl 1-bromocyclobutane-1-carboxylate (intermediate D) (233 mg, 1.21 mmol) was added. The mixture was heated at 65°

C. for 2 h. The mixture was cooled to r.t. and diluted with water (30 mL), extracted with EtOAc (3×). The extracts were washed with brine and dried over $Na_2SO_4$. Solvent was evaporated and the residue was purified by column on silica gel, eluting with 30% EtOAc in hexanes to give methyl 1-((3-(2-chloro-8-cyanoindolizin-5-yl)pyridin-4-yl)thio)cyclobutane-1-carboxylate (13e). MS-ESI (m/z): 398/400 [3:1, M+1]$^+$.

1-((3-(2-Chloro-8-cyanoindolizin-5-yl)pyridin-4-yl)thio)cyclobutane-1-carboxylic acid (13)

To a solution of 1-((3-(2-chloro-8-cyanoindolizin-5-yl)pyridin-4-yl)thio)-cyclobutane-1-carboxylate (13e, 40.6 mg) in MeOH (1 mL) was added 1 N NaOH (0.3 mL). The mixture was stirred at r.t. for 2 h. The mixture was diluted with water (5 mL), washed with DCM (2 mL). The aqueous solution was acidified with 1 N HCl to pH=2~3, extracted with DCM (2×5 mL). The extracts were dried over $Na_2SO_4$, solvent was evaporated to give 1-((3-(2-chloro-8-cyanoindolizin-5-yl)pyridin-4-yl)thio)cyclobutane-1-carboxylic acid (13). MS-ESI (m/z): 384/386 [3:1, M+1]$^+$.

Following essentially the same approach as described for Examples 13, Examples 14-19 listed in Table 2 were prepared by using appropriate starting materials and making necessary functional group manipulations when needed.

TABLE 2

| EXAMPLE | STRUCTURE | NAME | DATA |
|---|---|---|---|
| 14 | 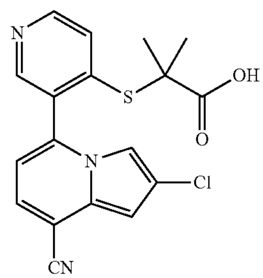 [SMILES: CC(C)(Sc1ccncc1-c1ccc(C#N)c2cc(Cl)cn12)C(=O)O] | 2-((3-(2-chloro-8-cyanoindolizin-5-yl)pyridin-4-yl)thio)-2-methylpropanoic acid | MS-ESI (m/z): 372/374 [3:1, M + 1]$^+$ |
| 15 | 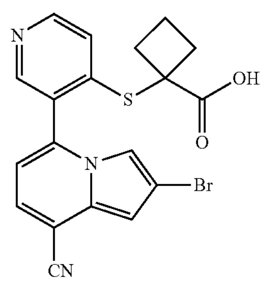 [SMILES: N#Cc1ccc(-c2cnccc2SC2(C(=O)O)CCC2)n2cc(Br)cc12] | 1-((3-(2-bromo-8-cyanoindolizin-5-yl)pyridin-4-yl)thio)cyclobutane-1-carboxylic acid | MS-ESI (m/z): 428/430 [1:1, M + 1]$^+$ |
| 16 | 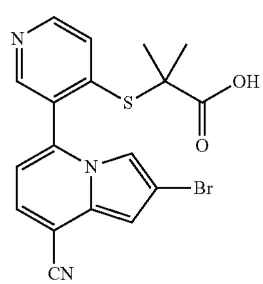 [SMILES: CC(C)(Sc1ccncc1-c1ccc(C#N)c2cc(Br)cn12)C(=O)O] | 2-((3-(2-bromo-8-cyanoindolizin-5-yl)pyridin-4-yl)thio)-2-methylpropanoic acid | MS-ESI (m/z): 416/418 [1:1, M + 1]$^+$ |
| 17 | 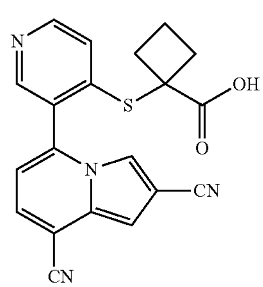 [SMILES: N#Cc1cc2c(C#N)ccc(-c3cnccc3SC3(C(=O)O)CCC3)n2c1] | 1-((3-(2,8-dicyanoindolizin-5-yl)pyridin-4-yl)thio)cyclobutane-1-carboxylic acid | MS-ESI (m/z): 375 [M + 1]$^+$ |

TABLE 2-continued

| EXAMPLE | STRUCTURE | NAME | DATA |
|---|---|---|---|
| 18 | 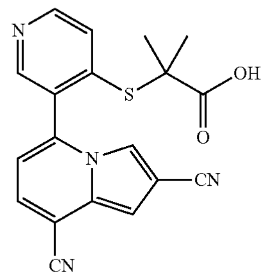 [SMILES: CC(C)(Sc1ccncc1-c1ccc(C#N)c2cc(C#N)cn12)C(=O)O] | 2-((3-(2,8-dicyanoindolizin-5-yl)pyridin-4-yl)thio)-2-methylpropanoic acid | MS-ESI (m/z): 363 [M + 1]+ |
| 19 | 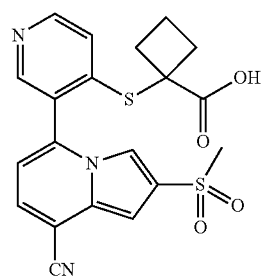 [SMILES: CS(=O)(=O)c1cc2c(C#N)ccc(-c3cnccc3SC3(C(=O)O)CCC3)n2c1] | 1-((3-(8-cyano-2-(methylsulfonyl)indolizin-5-yl)pyridin-4-yl)thio)cyclobutane-1-carboxylic acid | MS-ESI (m/z): 428 [M + 1]+ |

Example 20

1-((3-(8-Cyano-3-fluoroindolizin-5-yl)pyridin-4-yl)thio)cyclobutane-1-carboxylic acid (20)

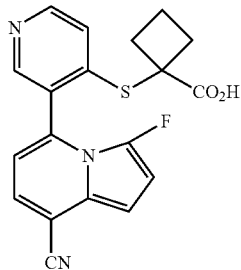

Methyl 1-((3-(8-cyano-3-fluoroindolizin-5-yl)pyridin-4-yl)thio)cyclobutane-1-carboxylate (20b), methyl 1-((3-(8-cyano-1-fluoroindolizin-5-yl)pyridin-4-yl)thio)cyclobutane-1-carboxylate (21a), and methyl 1-((3-(8-cyano-1,3-difluoroindolizin-5-yl)pyridin-4-yl)thio)cyclobutane-1-carboxylate (22a)

To a solution of methyl 1-((3-(8-cyanoindolizin-5-yl)pyridin-4-yl)thio)cyclobutane-1-carboxylate (20a, 44.3 mg, 0.122 mmol) in acetonitrile (1.3 mL) at 0° C. was added Select-F (51.8 mg, 0.146 mmol). After being stirred at this temperature for 1 h, the mixture was diluted with saturated aqueous NaHCO$_3$ (15 mL) and extracted with EtOAc (2×10 mL). The extracts were washed with brine (10 mL), dried over Na$_2$SO$_4$ and concentrated. The residue was separated by column on silica gel, eluted with 30-60% EtOAc in hexanes to give methyl 1-((3-(8-cyano-3-fluoroindolizin-5-yl)pyridin-4-yl)thio)cyclobutane-1-carboxylate (20b, MS-ESI (m/z): 382 [M+1]+), methyl 1-((3-(8-cyano-1-fluoroindolizin-5-yl)pyridin-4-yl)thio)cyclobutane-1-carboxylate (21a, MS-ESI (m/z): 382 [M+1]+), and methyl 1-((3-(8-cyano-1,3-difluoroindolizin-5-yl)pyridin-4-yl)thio)cyclobutane-1-carboxylate (22a, MS-ESI (m/z): 400 [M+1]+).

1-((3-(8-Cyano-3-fluoroindolizin-5-yl)pyridin-4-yl)thio)cyclobutane-1-carboxylic acid (20)

To a solution of methyl 1-((3-(8-cyano-3-fluoroindolizin-5-yl)pyridin-4-yl)thio)cyclobutane-1-carboxylate (20b, 12.6 mg) in MeOH (0.3 mL) was added 2.5 N NaOH (0.1 mL). The mixture was stirred at r.t. for 2 h. The mixture was diluted with water (3 mL), washed with DCM (2 mL). The aqueous solution was acidified with 1 N HCl to pH=2~3, extracted with DCM (2×3 mL). The extracts were dried over Na$_2$SO$_4$, solvent was evaporated to give 1-((3-(8-cyano-3-fluoroindolizin-5-yl)pyridin-4-yl)thio)cyclobutane-1-carboxylic acid (20). MS-ESI (m/z): 368 [M+1]+.

Example 21

1-((3-(8-Cyano-1 fluoroindolizin-5-yl)pyridin-4-yl)thio)cyclobutane-1-carboxylic acid (21)

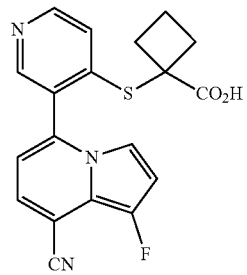

To a solution of methyl 1-((3-(8-cyano-1-fluoroindolizin-5-yl)pyridin-4-yl)thio)-cyclobutane-1-carboxylate (21a, 7.7 mg) in MeOH (0.3 mL) was added 2.5 N NaOH (0.1 mL). The mixture was stirred at r.t. for 2 h. The mixture was diluted with water (3 mL), washed with DCM (2 mL). The aqueous solution was acidified with 1 N HCl to pH=2~3, extracted with DCM (2×3 mL). The extracts were dried over Na$_2$SO$_4$, solvent was evaporated to give 1-((3-(8-cyano-1-fluoroindolizin-5-yl)pyridin-4-yl)thio)cyclobutane-1-carboxylic acid (21). MS-ESI (m/z): 368 [M+1]+.

Example 22

1-((3-(8-Cyano-1,3-difluoroindolizin-5-yl)pyridin-4-yl)thio)cyclobutane-1-carboxylic acid (22)

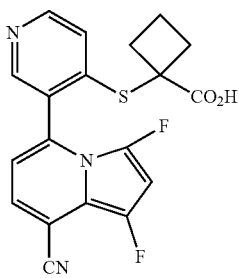

To a solution of methyl 1-((3-(8-cyano-1,3-difluoroindolizin-5-yl)pyridin-4-yl)thio)cyclobutane-1-carboxylate (22a, 4.0 mg) in MeOH (0.2 mL) was added 2.5 N NaOH (0.1 mL). The mixture was stirred at r.t. for 2 h. The mixture was diluted with water (3 mL), washed with DCM (2 mL). The aqueous solution was acidified with 1 N HCl to pH=2~3, extracted with DCM (2×3 mL). The extracts were dried over $Na_2SO_4$, solvent was evaporated to give 1-((3-(8-cyano-1,3-difluoroindolizin-5-yl)pyridin-4-yl)thio)cyclobutane-1-carboxylic acid (22). MS-ESI (m/z): 386 [M+1]$^+$.

Following essentially the same procedures described for Examples 1-7, Examples 23-35 listed in Table 3 were prepared by using the appropriate 2-bromo esters and making necessary functional group manipulations when needed.

TABLE 3

| EXAMPLE | STRUCTURE | NAME | DATA |
|---|---|---|---|
| 23 | 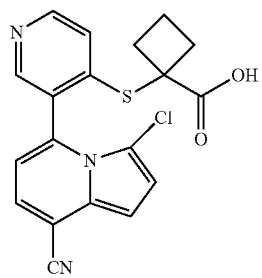 [SMILES: N#Cc1ccc(-c2cnccc2SC2(C(=O)O)CCC2)n2c(Cl)ccc12] | 1-((3-(3-chloro-8-cyanoindolizin-5-yl)pyridin-4-yl)thio)cyclobutane-1-carboxylic acid | MS-ESI (m/z): 384/386 [3:1, M + 1]$^+$ |
| 24 | 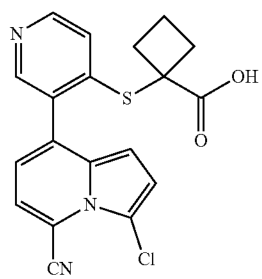 [SMILES: N#Cc1ccc(-c2cnccc2SC2(C(=O)O)CCC2)c2ccc(Cl)n12] | 1-((3-(1-chloro-8-cyanoindolizin-5-yl)pyridin-4-yl)thio)cyclobutane-1-carboxylic acid | MS-ESI (m/z): 384/386 [3:1, M + 1]$^+$ |
| 25 | 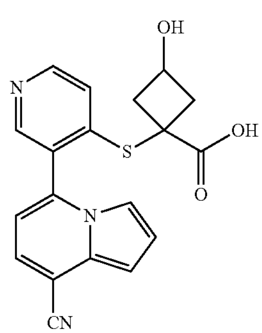 [SMILES: N#Cc1ccc(-c2cnccc2SC2(C(=O)O)CC(O)C2)n2cccc12] | 1-((3-(8-cyanoindolizin-5-yl)pyridin-4-yl)thio)-3-hydroxycyclobutane-1-carboxylic acid | MS-ESI (m/z): 366 [M + 1]$^+$ |

TABLE 3-continued

| EXAMPLE | STRUCTURE | NAME | DATA |
|---|---|---|---|
| 26 | 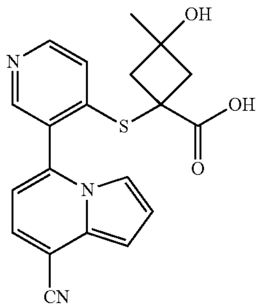 [SMILES: CC1(O)CC(Sc2ccncc2-c2ccc(C#N)c3cccn23)(C(=O)O)C1] | 1-((3-(8-cyanoindolizin-5-yl)pyridin-4-yl)thio)-3-hydroxy-3-methylcyclobutane-1-carboxylic acid | MS-ESI (m/z): 380 [M + 1]⁺ |
| 27 | 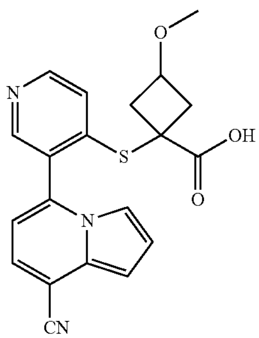 [SMILES: COC1CC(Sc2ccncc2-c2ccc(C#N)c3cccn23)(C(=O)O)C1] | 1-((3-(8-cyanoindolizin-5-yl)pyridin-4-yl)thio)-3-methoxycyclobutane-1-carboxylic acid | MS-ESI (m/z): 380 [M + 1]⁺ |
| 28 | 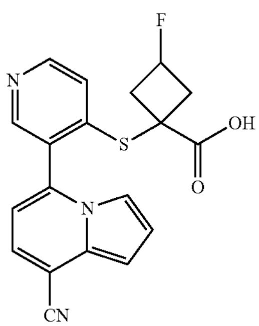 [SMILES: N#Cc1ccc(-c2cnccc2SC2(C(=O)O)CC(F)C2)n2cccc12] | 1-((3-(8-cyanoindolizin-5-yl)pyridin-4-yl)thio)-3-fluorocyclobutane-1-carboxylic acid | MS-ESI (m/z): 368 [M + 1]+ |
| 29 | 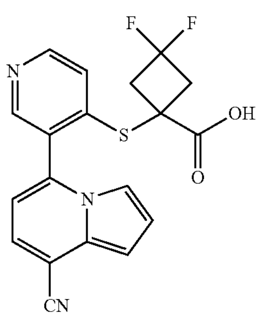 [SMILES: N#Cc1ccc(-c2cnccc2SC2(C(=O)O)CC(F)(F)C2)n2cccc12] | 1-((3-(8-cyanoindolizin-5-yl)pyridin-4-yl)thio)-3,3-difluorocyclobutane-1-carboxylic acid | MS-ESI (m/z): 386 [M + 1]+ |
| 30 | 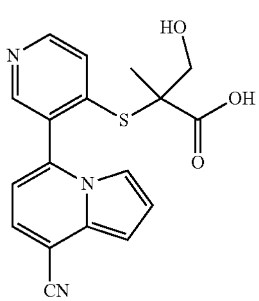 [SMILES: CC(CO)(Sc1ccncc1-c1ccc(C#N)c2cccn12)C(=O)O] | 2-((3-(8-cyanoindolizin-5-yl)pyridin-4-yl)thio)-3-hydroxy-2-methylpropanoic acid | MS-ESI (m/z): 354 [M + 1]⁺ |

TABLE 3-continued

| EXAMPLE | STRUCTURE | NAME | DATA |
| --- | --- | --- | --- |
| 31 | 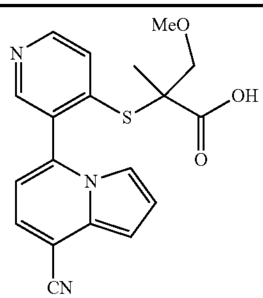 | 2-((3-(8-cyanoindolizin-5-yl)pyridin-4-yl)thio)-3-methoxy-2-methylpropanoic acid | MS-ESI (m/z): 368 [M + 1]$^+$ |
| 32 | 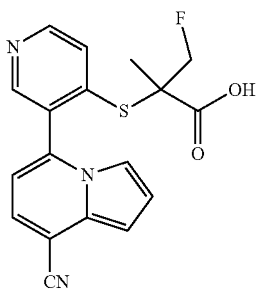 [SMILES: CC(CF)(Sc1ccncc1-c1ccc(C#N)c2cccn12)C(=O)O] | 2-((3-(8-cyanoindolizin-5-yl)pyridin-4-yl)thio)-3-fluoro-2-methylpropanoic acid | MS-ESI (m/z): 356 [M + 1]$^+$ |
| 33 | 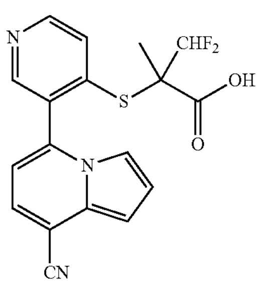 [SMILES: CC(Sc1ccncc1-c1ccc(C#N)c2cccn12)(C(=O)O)C(F)F] | 2-((3-(8-cyanoindolizin-5-yl)pyridin-4-yl)thio)-3,3-difluoro-2-methylpropanoic acid | MS-ESI (m/z): 374 [M + 1]$^+$ |
| 34 | 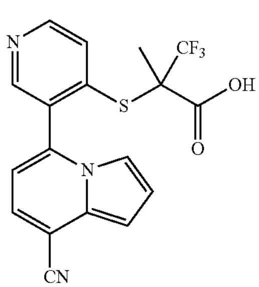 [SMILES: CC(Sc1ccncc1-c1ccc(C#N)c2cccn12)(C(=O)O)C(F)(F)F] | 2-((3-(8-cyanoindolizin-5-yl)pyridin-4-yl)thio)-3,3,3-trifluoro-2-methylpropanoic acid | MS-ESI (m/z): 392 [M + 1]$^+$ |

URAT1 In Vitro Inhibition Activity

The potency of the compounds of formula (I) as inhibitors of the URAT1 was determined as follow.

Cell Lines were generated in WuXi AppTec (HEK293-URAT-4: Stable cell line of HEK293 which was transfected with pcDNA3.1-URAT (Human SLC22A12 cDNA Clone, Abgent-DC07943). HEK293-PCDNA-5: Negative control cell of HEK293 which was transfected with pcDNA3.1 empty vector.

URAT1 In Vitro Inhibition Activity-Method A

Cells were seeded onto 24-well plates at the density of 2.0×10$^5$ cells per well. The cells were incubated at 37° C., 5% CO$_2$ overnight. After approximately 24 hours culture, cells were used for uptake experiments. The culture medium were removed from the wells and the cells were incubated in 0.4 ml/well of Hank's balanced salt solution (HBSS) for 10 min. HBSS was replaced with 0.18 ml/well fresh HBSS. Compounds were 5 folds serial diluted in DMSO, and then 25 folds diluted in HBSS. Compounds diluted with HBSS (10 μl) were added to relevant well of cell plates, and plates were incubated at 37° C., 5% CO$_2$ for 15 min. The final concentration of DMSO in the assay was 0.2%. 10 μl HBSS containing radioactively labeled Urate ($^{14}$C-uric acid) was added to each well. The final concentration of $^{14}$C-uric acid in the assay medium was 50 μM. After 10 min, the assay medium was immediately removed. The cells were washed quickly with 0.5 ml pre-chilled HBSS twice. 0.1 M NaOH (0.4 ml) was added to lyse the cells for at least 20 min. The cell lysate was collected to a scintillation vial, and scintillant (4 ml) was added and the radioactivity was counted by a liquid scintillation counter. Inhibiton % data were calculated using the formula $$\text{inhibition}\% = \frac{HC - CPD}{HC - LC} \times 100,$$

and analyzed using *Prism*5 software.

(*CN* 101679251)

CPD: Signal from a well containing a test compound
HC (high control): Average of signals from HEK293-URAT-4 cells
LC (low control): Average of signals from HEK293-PCDNA-5.

Select compounds prepared as described above were assayed according to the biological procedures described in Method A. The results are given in the Table 4.

TABLE 4

| Example | IC$_{50}$ (nM) |
|---|---|
| 1 | 30 |
| 2 | 66 |
| 3 | 282 |
| 4 | 68 |
| 5 | 110 |
| 7 | 44 |

URAT1 In Vitro Inhibition Activity-Method B

HEK293-URAT1 cell Lines were donated by Japan Fuji Biomedical Research Institute. Negative control cell of HEK293 (MOCK cells) which was transfected with pcDNA3.1 empty vector. HEK293-URAT1 cell lines and MOCK cell lines were cultured in complete growth medium consisting of DMEM supplemented with 10% FBS, penicillin and streptomycin.

Preparation of working solution: Each stock solutions was diluted to different concentrations (6, 20, 60, 200 and 600 μmol/L) with DMSO as 200× working solution, which was then diluted to 2×compound working solution with HBSS (Cl$^-$ free) buffer. Radiolabeled substrate $^{14}$C-Uric acid solution was diluted with HBSS (Cl$^-$ free) buffer to obtain 2× working solution which was mixed with an equal volume of 2× compound working solution to obtain the mixture of radiolabeled substrate and compound working solution.

HER293-URAT1 and MOCK cells were seeded onto 24-well plates at the density of 1.5×10$^6$ cells per well. The cells were incubated at 37° C., 5% CO$_2$ overnight. After cultured for approximately 2 to 3 days, cells were used for the experiments. The culture medium were removed from the wells, and cells were washed with HBSS (Cl$^-$ free) and incubated in 37° C. HBSS (Cl$^-$ free) for 10 min. HBSS was replaced with 500 μL of the mixture of radiolabeled substrate and compound working solution. The final concentration of $^{14}$C-Uric acid in the assay was 5.0 μmol/L. Plates were incubated at 37° C., 5% CO$_2$ for 2 min, and the reaction was stopped by the addition of pre-chilled HBSS (Cl$^-$ free) by washing three times. 400 μL NaOH (0.1 mmol/L) was added to lyse the cells and the cell lysate was collected to scintillation vials, and 3 ml scintillant (Aquasol-2, PerkinElmer) was added and after mixing completely, the radioactivity was counted by Tri-Carb 2910TR liquid scintillation counter. Each concentration of compounds, positive control and negative control were repeated in two wells (n=2). Inhibition % data were calculated using the formula:

Inhibition=[100×($U-U_0$)/($U_c-U_0$)]%, and analyzed using Prism5 software.

$U_0$: Average of signals of MOCK cells;
$U_c$: Average of signals of radiolabeled substrate. The half inhibition concentration of the tested compounds to URAT1 were analyzed using Prism 5 software.

Select compounds prepared as described above were assayed according to the biological procedures described Method B. The results are given in the Table 5.

TABLE 5

| Example | IC$_{50}$ (nM) |
|---|---|
| 8 | 55 |
| 10 | 424 |
| 11 | 828 |
| 12 | 271 |
| 13 | 26 |
| 14 | 30 |
| 15 | 29 |
| 17 | 45 |
| 19 | 332 |
| 20 | 34 |
| 21 | 85 |
| 23 | 89 |
| 24 | 34 |
| 31 | 504 |

Effect on Potassium Oxonate-Induced Hyperuricemia in Rats

Healthy male SD rats, weighing 250±20 g, were used. In the experiment, except for 10 rats as normal control group were orally administered with distilled water, the others were orally administered with yeast extract (20 g/kg, qd×5 days). One hour after last administration, all the rats were intraperitoneal injection with 250 mg/kg potassium oxonate while normal control group was treated with an equal volume of 0.5% CMC-Na (injection volume of 2 ml/kg). After one hour, rats were anesthetized with isoflurane and the serum uric acid was determined by uric acid test strip. All the rats were divided into groups by uric acid. The model control group and experimental groups was given orally administration 0.5% CMC-Na or compounds with a dose of 10 ml/kg-bw. Phosphotungstic acid precipitation method was used to detect serum uric acids in inner canthus blood at 0.5, 1, 2, 3, 4 h after administration, respectively. Substantially, observing the effects of compounds on serum uric acids levels and calculating each of groups' AUC and the inhibition of uric acid increased area by the equation as follows:

$$AUC(\%) = \frac{AUC_0 - AUC_1}{AUC_0 - AUC_2} \times 100\%$$

As shown in the equation, AUC$_0$ indicated the AUC of model control group, AUC$_1$ indicated the AUC of therapy group, AUC$_2$ indicated the AUC of normal control group.

Select compounds prepared as described above were assayed. The results are given in the table 6. The results show that the compounds of the invention are capable of decreasing the serum uric acid level of potassium oxonate-induced hyperuricemia in rats.

TABLE 6

Effect of compounds on serum uric acid levels (μmol/L)
in potassium oxonate-induced hyperuricemia in rats

| Example | Dosage (mg/kg) | Time after dosing (h) | | | | | |
|---|---|---|---|---|---|---|---|
| | | 0 | 0.5 | 1 | 2 | 3 | 4 |
| Test 1 | | | | | | | |
| Normal Control | — | 241.1 ± 43.5 | 237.5 ± 42.1 | 238.9 ± 45.7 | 242.5 ± 38.5 | 236.6 ± 33.1 | 222.1 ± 43.2 |
| Model Control | — | 403.3 ± 63.5## | 529.4 ± 81.1## | 564.5 ± 85.2## | 525.8 ± 104.1## | 440.6 ± 111.2## | 382.6 ± 116.7## |
| 1 | 5 | 389.6 ± 55.2 | 492.8 ± 82.4 | 506.0 ± 88.5 | 407.7 ± 100.7* | 343.2 ± 84.3* | 289.8 ± 77.8 |
| Test 2 | | | | | | | |
| Normal Control | — | 199.0 ± 24.2 | 206.6 ± 18.2 | 216.0 ± 21.1 | 217.1 ± 19.3 | 212.1 ± 16.6 | 211.2 ± 16.7 |
| Model Control | — | 368.4 ± 37.9## | 504.2 ± 47.1## | 551.9 ± 47.0## | 463.3 ± 56.1## | 389.4 ± 72.8## | 344.5 ± 76.5## |
| 7 | 5 | 364.1 ± 32.8 | 485.3 ± 79.3 | 510.0 ± 103.7 | 460.6 ± 87.4 | 381.3 ± 84.3 | 307.9 ± 71.0 |
| 13 | 5 | 373.8 ± 44.1 | 487.2 ± 46.9 | 523.6 ± 50.4 | 422.0 ± 54.1 | 341.4 ± 69.4 | 295.5 ± 47.2 |
| 14 | 5 | 360.2 ± 44.9 | 476.3 ± 53.4 | 489.5 ± 83.1 | 385.8 ± 68.2* | 337.2 ± 72.4 | 285.4 ± 47.7 |
| 15 | 5 | 363.8 ± 47.1 | 476.8 ± 61.7 | 496.3 ± 74.8 | 401.7 ± 52.9* | 331.3 ± 70.5 | 278.0 ± 46.0* |
| 16 | 5 | 366.9 ± 36.8 | 460.6 ± 46.5 | 491.9 ± 77.4 | 380.6 ± 47.4** | 293.9 ± 42.1** | 264.7 ± 38.8* |
| Test 3 | | | | | | | |
| Normal Control | — | 195.4 ± 28.6 | 207.2 ± 29.5 | 212.4 ± 32.6 | 217.6 ± 36.2 | 229.0 ± 61.0 | 211.0 ± 33.1 |
| Model Control | — | 362.2 ± 36.5## | 469.1 ± 53.8## | 481.5 ± 51.0## | 432.4 ± 40.5## | 397.7 ± 52.5## | 380.4 ± 60.9## |
| 8 | 5 | 360.3 ± 34.0 | 449.8 ± 39.8 | 483.9 ± 62.9 | 451.2 ± 58.9 | 393.9 ± 68.6 | 358.3 ± 68.2 |
| 9 | 5 | 342.1 ± 31.6 | 432.1 ± 43.2 | 450.8 ± 40.9 | 385.5 ± 52.2* | 347.1 ± 46.8* | 336.3 ± 59.1 |
| 17 | 5 | 352.3 ± 32.9 | 454.4 ± 39.8 | 458.1 ± 66.7 | 432.2 ± 67.6 | 403.0 ± 70.0 | 340.1 ± 56.0 |

*P < 0.05, compared with model control group;
**P < 0.01, compared with model control group;
P < 0.01, compared with normal control group.

What is claimed is:

1. A compound of formula (I):

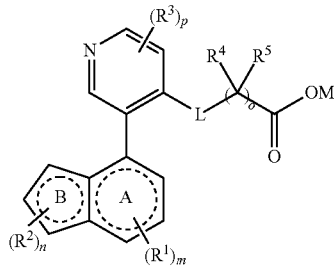

(I)

or a pharmaceutically acceptable salt thereof,
wherein:
A-B is a 6-5 membered fused indolizine ring system, which is:

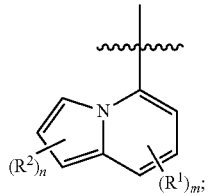

L is selected from $NR^X$, O and S;
each $R^1$ is independently selected from hydrogen, hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, —CN, —NO$_2$, —NR$^{A1}$R$^{B1}$, —OR$^{A1}$, —S(O)$_r$R$^{A1}$, —S(O)$_2$OR$^{A1}$, —OS(O)$_2$R$^{A1}$, —P(O)R$^{A1}$R$^{B1}$, —P(O)(OR$^{A1}$)(OR$^{B1}$), —C(O)R$^{A1}$, —C(O)OR$^{A1}$, —OC(O)R$^{A1}$, —C(O)NR$^{A1}$R$^{B1}$, —NR$^{A1}$C(O)R$^{B1}$, —OC(O)NR$^{A1}$R$^{B1}$, —NR$^{A1}$C(O)OR$^{B1}$, —NR$^{A1}$C(O)NR$^{A1}$R$^{B1}$, —NR$^{A1}$C(S)NR$^{A1}$R$^{B1}$, —S(O)$_r$NR$^{A1}$R$^{B1}$, —NR$^{A1}$S(O)$_r$R$^{B1}$, —NR$^{A1}$S(O)$_2$NR$^{A1}$R$^{B1}$, —S(O)(=NR$^{E1}$)R$^{B1}$, —N=S(O)R$^{A1}$R$^{B1}$, —NR$^{A1}$S(O)(=NR$^{E1}$)R$^{B1}$, —S(O)(=NR$^{E1}$)NR$^{A1}$R$^{B1}$, —NR$^{A1}$S(O)(=NR$^{E1}$)NR$^{A1}$R$^{B1}$, —C(=N$^{E1}$)R$^{A1}$, —C(=N—OR$^{B1}$)R$^{A1}$, —C(=N$^{E1}$R$^{A1}$R$^{B1}$, —NR$^{A1}$C(=NR$^{E1}$)R$^{B1}$, and —NR$^{A1}$C(=NR$^{E1}$)NR$^{A1}$R$^{B1}$, wherein alkyl, alkenyl, alkynyl, cycloalkyl, heterocyclyl, aryl and heteroaryl are each unsubstituted or substituted with at least one substituent, such as one, two, three, or four substituents, independently selected from $R^X$;

each $R^2$ is independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, —CN, —NO$_2$, —NR$^{A2}$R$^{B2}$, —OR$^{A2}$, —S(O)$_r$R$^{A2}$, —S(O)$_2$OR$^{A2}$, —OS(O)$_2$R$^{A2}$, —P(O)R$^{A2}$R$^{B2}$, —P(O)(OR$^{A2}$)(OR$^{B2}$), —C(O)R$^{A2}$, —C(O)OR$^{A2}$, —OC(O)R$^{A2}$, —C(O)NR$^{A2}$R$^{B2}$, —NR$^{A2}$C(O)R$^{B2}$—OC(O)NR$^{A2}$R$^{B2}$, —NR$^{A2}$C(O)OR$^{B2}$, —NR$^{A2}$C(O)NR$^{A2}$R$^{B2}$, —NR$^{A2}$C(S)NR$^{A2}$R$^{B2}$, —S(O)$_r$NR$^{A2}$R$^{B2}$, —NR$^{A2}$S(O)$_r$R$^{B2}$, —NR$^{A2}$S(O)$_2$NR$^{A2}$R$^{B2}$, —S(O)(=NR$^{E2}$)R$^{B2}$, —N=S(O)R$^{A2}$R$^{B2}$, —NR$^{A2}$S(O)(=NR$^{E2}$)R$^{B2}$, —S(O)(=NR$^{E2}$)NR$^{A2}$R$^{B2}$, —NR$^{A2}$S(O)(=NR$^{E2}$)NR$^{A2}$R$^{B2}$, —C(=NR$^{E2}$)R$^{A2}$, —C(=N—OR$^{B2}$)R$^{A2}$, —C(=NR$^{E2}$)R$^{A2}$R$^{B2}$, —NR$^{A2}$C(=NR$^{E2}$)R$^{B2}$ and —NR$^{A2}$C(=NR$^{E2}$)NR$^{A2}$R$^{B2}$ wherein alkyl, alkenyl, alkynyl, cycloalkyl, heterocyclyl, aryl and heteroaryl are each unsubstituted or substituted with at least one substituent, such as one, two, three, or four substituents, independently selected from R$^X$;

each R$^3$ is independently selected from hydrogen, halogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, heteroaryl-C$_{1-4}$ alkyl, —CN, —NO$_2$, —NR$^{A3}$R$^{B3}$, —OR$^{A3}$, —S(O)$_r$R$^{A3}$, —S(O)$_2$OR$^{A3}$, —OS(O)$_2$R$^{A3}$, —P(O)R$^{A3}$R$^{B3}$, —P(O)(OR$^{A3}$)(OR$^{B3}$), —C(O)R$^{A3}$, —C(O)OR$^{A3}$, —OC(O)R$^{A3}$, —C(O)NR$^{A3}$R$^{B3}$, —NR$^{A3}$C(O)R$^{B3}$, OC(O)NR$^{A3}$R$^{B3}$, —NR$^{A3}$C(O)OR$^{B3}$, —NR$^{A3}$C(O)NR$^{A3}$R$^{B3}$, —NR$^{A3}$C(S)NR$^{A3}$R$^{B3}$, —S(O)$_r$NR$^{A3}$R$^{B3}$, —NR$^{A3}$(O)$_r$R$^{B3}$, —NR$^{A3}$S(O)$_2$NR$^{A3}$R$^{B3}$, —S(O)(=NR$^{E3}$)R$^{B3}$, —N=S(O)R$^{A3}$R$^{B3}$, —NR$^{A3}$S(O)(=NR$^{E3}$)R$^{B3}$, —S(O)(=NR$^{E3}$)NR$^{A3}$R$^{B3}$, —NR$^{A3}$S(O)(=NR$^{E3}$)NR$^{A3}$R$^{B3}$, —C(=NR$^{E3}$)R$^{A3}$, —C(=N—OR$^{B3}$)R$^{A3}$, —C(=NR$^{E3}$)NR$^{A3}$R$^{B3}$, —NR$^{A3}$C(=NR$^{E3}$)R$^{B3}$, and —NR$^{A3}$C(=NR$^{E3}$)NR$^{A3}$R$^{B3}$, wherein alkyl, alkenyl, alkynyl, cycloalkyl, heterocyclyl, aryl and heteroaryl are each unsubstituted or substituted with at least one substituent, such as one, two, three, or four substituents, independently selected from R$^X$;

each R$^4$ and R$^5$ are independently selected from hydrogen, halogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, heteroaryl-C$_{1-4}$ alkyl, wherein the said alkyl, cycloalkyl and heterocyclyl is unsubstituted or substituted with at least one substituent, such as one, two, three, or four substituents, independently selected from R$^X$;

or R$^4$ and R$^5$ together with the carbon atom to which they are attached form a ring of 3 to 7 members containing 0, 1, or 2 heteroatoms independently selected from oxygen, sulfur and nitrogen, and optionally substituted with 1, 2 or 3 R$^X$ groups;

each R$^{A1}$, R$^{A2}$, R$^{A3}$, R$^{B1}$, R$^{B2}$ and R$^{B3}$ are independently selected from hydrogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, and heteroaryl-C$_{1-4}$ alkyl, wherein alkyl, alkenyl, alkynyl, cycloalkyl, heterocyclyl, aryl and heteroaryl are each unsubstituted or substituted with at least one substituent, such as one, two, three, or four substituents, independently selected from R$^X$;

or each "R$^{A1}$ and R$^{B1}$", "R$^{A2}$ and R$^{B2}$", or "R$^{A3}$ and R$^{B3}$" together with the atom(s) to which they are attached form a heterocyclic ring of 4 to 12 members containing 0, 1, or 2 additional heteroatoms independently selected from oxygen, sulfur, nitrogen and phosphorus, and optionally substituted with 1, 2 or 3 R$^X$ groups;

each R$^{E1}$, R$^{E2}$ and R$^{E3}$ are independently selected from hydrogen, C$_{1-10}$ alkyl, CN, NO$_2$, OR$^{a1}$, SR$^{a1}$, —S(O)$_r$R$^{a1}$, —S(O)$_r$NR$^{a1}$R$^{b1}$, —C(O)R$^{a1}$, —C(O)OR$^{a1}$, and —C(O)NR$^{a1}$R$^{b1}$;

each R$^X$ is independently selected from C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, heteroaryl-C$_{1-4}$ alkyl, halogen, —CN, —NO$_2$, —(CR$^{c1}$R$^{d1}$)$_t$NR$^{a1}$R$^{b1}$, —(CR$^{c1}$R$^{d1}$)$_t$OR$^{b1}$, —(CR$^{c1}$R$^{d1}$)$_t$S(O)$_r$R$^{b1}$, —(CR$^{c1}$R$^{d1}$)$_t$S(O)$_2$OR$^{b1}$, —(CR$^{c1}$R$^{d1}$)$_t$OS(O)$_2$R$^{b1}$, —(CR$^{c1}$R$^{d1}$)$_t$P(O)R$^{a1}$R$^{a1}$, —(CR$^{c1}$R$^{d1}$)$_t$P(O)(OR$^{a1}$)(OR$^{a1}$), —(CR$^{c1}$R$^{d1}$)$_t$C(O)R$^{a1}$, —(CR$^{c1}$R$^{d1}$)$_t$C(O)OR$^{b1}$, —(CR$^{c1}$R$^{d1}$)$_t$C(O)R$^{b1}$, —(CR$^{c1}$R$^{d1}$)$_t$C(O)NR$^{a1}$R$^{b1}$, —(CR$^{c1}$R$^{d1}$)$_t$NR$^{a1}$C(O)R$^{b1}$, —(CR$^{c1}$R$^{d1}$)$_t$OC(O)NR$^{a1}$R$^{b1}$, —(CR$^{c1}$R$^{d1}$)$_t$NR$^{a1}$C(O)OR$^{b1}$, —(CR$^{c1}$R$^{d1}$)$_t$NR$^{a1}$C(O)NR$^{a1}$R$^{b1}$, —(CR$^{c1}$R$^{d1}$)$_t$NR$^{a1}$C(S)NR$^{a1}$R$^{b1}$, —(CR$^{c1}$R$^{d1}$)$_t$S(O)$_r$NR$^{a1}$R$^{b1}$, —(CR$^{c1}$R$^{d1}$)$_t$NR$^{a1}$S(O)$_r$R$^{b1}$, —(CR$^{c1}$R$^{d1}$)$_t$NR$^{a1}$S(O)$_2$NR$^{a1}$R$^{b1}$, —(CR$^{c1}$R$^{d1}$)$_t$S(O)(=NR$^{e1}$)R$^{b1}$, —(CR$^{c1}$R$^{d1}$)N=S(O)R$^{a1}$R$^{b1}$, —(CR$^{c1}$R$^{d1}$)$_t$NR$^{a1}$S(O)(=NR$^{e1}$)R$^{b1}$, —(CR$^{c1}$R$^{d1}$)$_t$S(O)(=NR$^{e1}$)NR$^{a1}$R$^{b1}$, —(CR$^{c1}$R$^{d1}$)$_t$NR$^{a1}$S(O)(=NR$^{e1}$)NR$^{a1}$R$^{b1}$, —(CR$^{c1}$R$^{d1}$)$_t$C(=NR$^{e1}$)R$^{a1}$, —(CR$^{c1}$R$^{d1}$)$_t$C(=N—OR$^{b1}$)R$^{a1}$, —(CR$^{c1}$R$^{d1}$)$_t$C(=NR$^{e1}$)NR$^{a1}$R$^{b1}$, —(CR$^{c1}$R$^{d1}$)$_t$NR$^{a1}$C(=NR$^{e1}$)R$^{b1}$, and —(CR$^{c1}$R$^{d1}$)$_t$NR$^{a1}$C(=NR$^{e1}$)NR$^{a1}$R$^{b1}$, wherein alkyl, alkenyl, alkynyl, cycloalkyl, heterocyclyl, aryl and heteroaryl are each unsubstituted or substituted with at least one substituent, such as one, two, three, or four substituents, independently selected from R$^Y$;

each R$^{a1}$ and each R$^{b1}$ are independently selected from hydrogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, and heteroaryl-C$_{1-4}$ alkyl, wherein alkyl, alkenyl, alkynyl, cycloalkyl, heterocyclyl, aryl and heteroaryl are each unsubstituted or substituted with at least one substituent, such as one, two, three, or four substituents, independently selected from R$^Y$;

or R$^{a1}$ and R$^{b1}$ together with the atom(s) to which they are attached form a heterocyclic ring of 4 to 12 members containing 0, 1, or 2 additional heteroatoms independently selected from oxygen, sulfur, nitrogen and phosphorus, and optionally substituted with 1, 2, or 3 R$^Y$ groups;

each R$^{c1}$ and each R$^{d1}$ are independently selected from hydrogen, halogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, and heteroaryl-C$_{1-4}$ alkyl, wherein alkyl, alkenyl, alkynyl, cycloalkyl, heterocyclyl, aryl and heteroaryl are each unsubstituted or substituted with at least one substituent, such as one, two, three, or four substituents, independently selected from R$^Y$;

or R$^{c1}$ and R$^{d1}$ together with the carbon atom(s) to which they are attached form a ring of 3 to 12 members containing 0, 1, or 2 heteroatoms independently selected from oxygen, sulfur and nitrogen, and optionally substituted with 1, 2, or 3 R$^Y$ groups;

each R$^{e1}$ is independently selected from hydrogen, C$_{1-10}$ alkyl, C$_{3-10}$ cycloalkyl, C$_{3-10}$ cycloalkyl-C$_{1-4}$ alkyl, CN, NO$_2$, OR$^{a2}$, SR$^{a2}$, —S(O)$_r$R$^{a2}$, —S(O)$_r$NR$^{a2}$R$^{b2}$, —C(O)R$^{a2}$, —C(O)OR$^{a2}$, and —C(O)NR$^{a2}$R$^{b2}$;

R$^Y$ is independently selected from C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, heteroaryl-C$_{1-4}$ alkyl, halogen, —CN, —NO$_2$, —(CR$^{c2}$R$^{d2}$)$_t$NR$^{a2}$R$^{b2}$, —(CR$^{c2}$R$^{d2}$)$_t$OR$^{b2}$, —(CR$^{c2}$R$^{d2}$)$_t$S(O)$_r$R$^{b2}$, —(CR$^{c2}$R$^{d2}$)$_t$S(O)$_2$OR$^{b2}$, —(CR$^{c2}$R$^{d2}$)$_t$OS(O)$_2$R$^{b2}$, —(CR$^{c2}$R$^{d2}$)$_t$P(O)R$^{a2}$R$^{b2}$, —(CR$^{c2}$R$^{d2}$)$_t$P(O)(OR$^{a2}$)(OR$^{b2}$), (CR$^{c2}$R$^{d2}$)$_t$C(O)R$^{a2}$, —(CR$^{c2}$R$^{d2}$)$_t$C(O)OR$^{b2}$, —(CR$^{c2}$R$^{d2}$)$_t$OC(O)R$^{b2}$, —(CR$^{c2}$R$^{d2}$)$_t$C(O)NR$^{a1}$R$^{b2}$, —(CR$^{c2}$R$^{d2}$)$_t$NR$^{a2}$C(O)R$^{b2}$, (CR$^{c2}$R$^{d2}$)$_t$OC(O)NR$^{a2}$R$^{b2}$, —(CR$^{c2}$R$^{d2}$)$_t$NR$^{a2}$C(O)OR$^{b2}$, —(CR$^{c2}$R$^{d2}$)$_t$NR$^{a2}$C(O)NR$^{a2}$R$^{b2}$, (CR$^{c2}$R$^{d2}$)$_t$NR$^{a2}$C(S)NR$^{a2}$R$^{b2}$, —(CR$^{c2}$R$^{d2}$)$_t$S(O)$_r$NR$^{a2}$R$^{b2}$, (CR$^{c2}$R$^{d2}$)$_t$NR$^{a2}$S(O)$_r$ $R^{b2}$, $(CR^{c2}R^{d2})_t NR^{a2}S(O)_2 NR^{a2}R^{b2}$, $-(CR^{c2}R^{d2})_t S(O)(=NR^{e2})R^{b2}$, $-(CR^{c2}R^{d2})_t N=S(O)R^{a2}R^{b2}$, $-(CR^{c2}R^{d2})_t NR^{a2}S(O)(=NR^{e2})R^{b2}$, $-(CR^{c2}R^{d2})_t S(O)(=NR^{e2})NR^{a2}R^{b2}$, $-(CR^{c2}R^{d2})_t NR^{a2}S(O)(=NR^{e2})NR^{a2}R^{b2}$, $-(CR^{c2}R^{d2})_t C(=NR^{e2})R^{a2}$, $-(CR^{c2}R^{d2})_t C(=N-OR^{b2})R^{a2}$, $-(CR^{c2}R^{d2})_t C(=NR^{e2})NR^{a2}R^{b2}$, $-(CR^{c2}R^{d2})_t NR^{a2}C(=NR^{e2})R^{b2}$, and $-(CR^{c2}R^{d2})_t NR^{a2}C(=NR^{e2})NR^{a1}R^{b2}$, wherein alkyl, alkenyl, alkynyl, cycloalkyl, heterocyclyl, aryl and heteroaryl are each unsubstituted or substituted with at least one substituent, such as one, two, three, or four substituents, independently selected from OH, CN, amino, halogen, $C_{1-10}$ alkyl, $C_{2-10}$ alkenyl, $C_{2-10}$ alkynyl, $C_{3-10}$ cycloalkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino and di($C_{1-10}$ alkyl)amino;

each $R^{a2}$ and each $R^{b2}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl)amino, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, such as one, two, three, or four substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

or $R^{a2}$ and $R^{b2}$ together with the atom(s) to which they are attached form a heterocyclic ring of 4 to 12 members containing 0, 1, or 2 additional heteroatoms independently selected from oxygen, sulfur, nitrogen and phosphorus, and optionally substituted with 1 or 2 substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{c2}$ and each $R^{d2}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl)amino, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, such as one, two, three, or four substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

or $R^{c2}$ and $R^{d2}$ together with the carbon atom(s) to which they are attached form a ring of 3 to 12 members containing 0, 1, or 2 heteroatoms independently selected from oxygen, sulfur and nitrogen, and optionally substituted with 1 or 2 substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{e2}$ is independently selected from hydrogen, CN, $NO_2$, $C_{1-10}$ alkyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $-C(O)C_{1-4}$ alkyl, $-C(O)C_{3-10}$ cycloalkyl, $-C(O)OC_{1-4}$ alkyl, $-C(O)OC_{3-10}$ cycloalkyl, $-C(O)NH_2$, $-C(O)NH(C_{1-4}$ alkyl), $-C(O)N(C_{1-4}$ alkyl$)_2$, $-C(O)NH(C_{3-10}$ cycloalkyl), $-C(O)N(C_{3-10}$ cycloalkyl$)_2$, $-S(O)_2C_{1-4}$ alkyl, $-S(O)_2C_{3-10}$ cycloalkyl, $-S(O)_2NH_2$, $-S(O)_2NH(C_{1-4}$ alkyl), $-S(O)_2N(C_{1-4}$ alkyl$)_2$, $-S(O)_2NH(C_{3-10}$ cycloalkyl) and $-S(O)_2N(C_{3-10}$ cycloalkyl$)_2$;

M is hydrogen, $C_{1-4}$ alkyl or a pharmaceutically acceptable cation;

m is independently selected from 0, 1, 2 and 3;

n is independently selected from 0, 1, 2, and 3;

o is selected from 1, 2, and 3;

p is independently selected from 0, 1, 2 and 3;

each r is independently selected from 0, 1 and 2;

each t is independently selected from 0, 1, 2, 3 and 4.

2. The compound of claim 1 or a pharmaceutically acceptable salt thereof, wherein L is selected from O and S.

3. The compound of claim 2 or a pharmaceutically acceptable salt thereof, wherein L is S.

4. The compound of claim 1 or a pharmaceutically acceptable salt thereof, wherein $R^4$ and $R^5$ are independently selected from $C_{1-10}$ alkyl, and optionally substituted with 1, 2 or 3 $R^X$ groups, or $R^4$ and $R^5$ together with the carbon atom to which they are attached form a ring of 3 to 7 members containing 0, 1, or 2 heteroatoms independently selected from oxygen, sulfur and nitrogen, and optionally substituted with 1, 2 or 3 $R^X$ groups.

5. The compound of claim 1 or a pharmaceutically acceptable salt thereof, wherein $R^4$ and $R^5$ together with the carbon atom to which they are attached form cyclopropyl, cyclobutyl, cyclopentyl or cyclohexyl, and optionally substituted with 1, 2 or 3 $R^X$ groups.

6. The compound of claim 5 or a pharmaceutically acceptable salt thereof, wherein $R^4$ and $R^5$ together with the carbon atom to which they are attached form cyclobutyl, and optionally substituted with 1, 2 or 3 halogen, $C_{1-10}$ alkyl, OH, or $C_{1-10}$ alkoxy.

7. The compound of claim 6 or a pharmaceutically acceptable salt thereof, wherein $R^4$ and $R^5$ together with the carbon atom to which they are attached form cyclobutyl, and optionally substituted with 1, 2 or 3 F, methyl, OH, or $OCH_3$.

8. The compound of claim 4 or a pharmaceutically acceptable salt thereof, wherein $R^4$ and $R^5$ are methyl, and optionally substituted with 1, 2 or 3 $R^X$ groups.

9. The compound of claim 8 or a pharmaceutically acceptable salt thereof, wherein $R^4$ and $R^5$ are methyl, and optionally substituted with 1, 2 or 3 OH, $OCH_3$ and F.

10. The compound of claim 1 or a pharmaceutically acceptable salt thereof, wherein $R^1$ is CN.

11. The compound of claim 1 or a pharmaceutically acceptable salt thereof, wherein $R^2$ is selected from hydrogen, halogen, CN, $C_{1-10}$ alkyl, $C_{3-10}$ cycloalkyl, and $-(CR^{C1}R^{D1})_r S(O)_r R^{41}$.

12. The compound of claim 11 or a pharmaceutically acceptable salt thereof, wherein $R^2$ is selected from hydrogen, fluorine, chlorine, bromine, methyl, $CF_3$, CN and $SO_2CH_3$.

13. The compound of claim 1 or a pharmaceutically acceptable salt thereof, wherein $R^3$ is hydrogen.

14. The compound of claim 1 or a pharmaceutically acceptable salt thereof, wherein M is selected from hydrogen, $C_{1-4}$ alkyl, and a pharmaceutically acceptable cation.

15. The compound of claim 14 or a pharmaceutically acceptable salt thereof, wherein M is hydrogen.

16. The compound of claim 14 or a pharmaceutically acceptable salt thereof, wherein the pharmaceutically acceptable cation is $Na^+$, $Li^+$, $K^+$, $Ca^{2+}$, $Mg^{2+}$, $NH_4^+$, tetramethylammonium, tetraethylammonium, methylammonium, dimethylammonium, trimethylammonium, or triethylammonium.

17. The compound of claim 1, selected from
1-((3-(8-cyanoindolizin-5-yl)pyridin-4-yl)thio)cyclobutane-1-carboxylic acid,
2-((3-(8-cyanoindolizin-5-yl)pyridin-4-yl)thio)-2-methylpropanoic acid,
2-((3-(3-chloro-8-cyanoindolizin-5-yl)pyridin-4-yl)thio)-2-methylpropanoic acid,
2-((3-(1-chloro-8-cyanoindolizin-5-yl)pyridin-4-yl)thio)-2-methylpropanoic acid,
1-((3-(8-cyano-2-methylindolizin-5-yl)pyridin-4-yl)thio)cyclobutane-1-carboxylic acid,
2-((3-(8-cyano-2-methylindolizin-5-yl)pyridin-4-yl)thio)-2-methylpropanoic acid,
1-((3-(8-cyano-2-(trifluoromethyl)indolizin-5-yl)pyridin-4-yl)thio)cyclobutane-1-carboxylic acid,
1-((3-(2-chloro-8-cyanoindolizin-5-yl)pyridin-4-yl)thio)cyclobutane-1-carboxylic acid,
2-((3-(2-chloro-8-cyanoindolizin-5-yl)pyridin-4-yl)thio)-2-methylpropanoic acid,
1-((3-(2-bromo-8-cyanoindolizin-5-yl)pyridin-4-yl)thio)cyclobutane-1-carboxylic acid,
2-((3-(2-bromo-8-cyanoindolizin-5-yl)pyridin-4-yl)thio)-2-methylpropanoic acid,
1-((3-(2,8-dicyanoindolizin-5-yl)pyridin-4-yl)thio)cyclobutane-1-carboxylic acid,
2-((3-(2,8-dicyanoindolizin-5-yl)pyridin-4-yl)thio)-2-methylpropanoic acid,
1-((3-(8-cyano-2-(methylsulfonyl)indolizin-5-yl)pyridin-4-yl)thio)cyclobutane-1-carboxylic acid,
1-((3-(8-cyano-3-fluoroindolizin-5-yl)pyridin-4-yl)thio)cyclobutane-1-carboxylic acid,
1-((3-(8-cyano-1-fluoroindolizin-5-yl)pyridin-4-yl)thio)cyclobutane-1-carboxylic acid,
1-((3-(8-cyano-1,3-difluoroindolizin-5-yl)pyridin-4-yl)thio)cyclobutane-1-carboxylic acid,
1-((3-(3-chloro-8-cyanoindolizin-5-yl)pyridin-4-yl)thio)cyclobutane-1-carboxylic acid,
1-((3-(1-chloro-8-cyanoindolizin-5-yl)pyridin-4-yl)thio)cyclobutane-1-carboxylic acid,
1-((3-(8-cyanoindolizin-5-yl)pyridin-4-yl)thio)-3-hydroxycyclobutane-1-carboxylic acid,
1-((3-(8-cyanoindolizin-5-yl)pyridin-4-yl)thio)-3-hydroxy-3-methylcyclobutane-1-carboxylic acid,
1-((3-(8-cyanoindolizin-5-yl)pyridin-4-yl)thio)-3-methoxycyclobutane-1-carboxylic acid,
1-((3-(8-cyanoindolizin-5-yl)pyridin-4-yl)thio)-3-fluorocyclobutane-1-carboxylic acid,
1-((3-(8-cyanoindolizin-5-yl)pyridin-4-yl)thio)-3,3-difluorocyclobutane-1-carboxylic acid,
2-((3-(8-cyanoindolizin-5-yl)pyridin-4-yl)thio)-3-hydroxy-2-methylpropanoic acid,
2-((3-(8-cyanoindolizin-5-yl)pyridin-4-yl)thio)-3-methoxy-2-methylpropanoic acid,
2-((3-(8-cyanoindolizin-5-yl)pyridin-4-yl)thio)-3-fluoro-2-methylpropanoic acid,
2-((3-(8-cyanoindolizin-5-yl)pyridin-4-yl)thio)-3,3-difluoro-2-methylpropanoic acid,
2-((3-(8-cyanoindolizin-5-yl)pyridin-4-yl)thio)-3,3,3-trifluoro-2-methylpropanoic acid,
or pharmaceutically acceptable salts thereof.

18. A pharmaceutical composition, comprising a compound of claim 1 or a pharmaceutically acceptable salt thereof, and at least one pharmaceutically acceptable carrier.

19. A method for treating hyperuricemia or gout comprising administering to a subject in need thereof a therapeutically effective amount of a compound of claim 1 or a pharmaceutically acceptable salt thereof.

20. A method for treating hyperuricemia or gout comprising administering to a subject in need thereof a therapeutically effective amount of a compound of claim 17 or a pharmaceutically acceptable salt thereof.

* * * * *